United States Patent
Cai et al.

(10) Patent No.: US 9,428,756 B2
(45) Date of Patent: Aug. 30, 2016

(54) ZINC FINGER NUCLEASE-MEDIATED HOMOLOGOUS RECOMBINATION

(75) Inventors: Qihua Cai, Westfield, IN (US); Jeffrey C. Miller, San Leandro, CA (US); William M. Ainley, Carmel, IN (US); Robbi J. Garrison, Fillmore, IN (US); Joseph F. Petolino, Zionsville, IN (US); Beth C. Rubin-Wilson, Indianapolis, IN (US); Lisa L. Schulenberg, Pittsboro, IN (US); Andrew F. Worden, Fillmore, IN (US)

(73) Assignees: Dow AgroSciences LLC, Indianapolis, IN (US); Sangamo BioSciences, Inc., Richmond, CA (US)

(*) Notice: Subject to any disclaimer, the term of this patent is extended or adjusted under 35 U.S.C. 154(b) by 1335 days.

(21) Appl. No.: 12/376,871

(22) PCT Filed: Aug. 9, 2007

(86) PCT No.: PCT/US2007/017748
§ 371 (c)(1),
(2), (4) Date: Feb. 9, 2009

(87) PCT Pub. No.: WO2008/021207
PCT Pub. Date: Feb. 21, 2008

(65) Prior Publication Data
US 2010/0257638 A1   Oct. 7, 2010

Related U.S. Application Data

(60) Provisional application No. 60/837,147, filed on Aug. 11, 2006.

(51) Int. Cl.
*C12N 15/82* (2006.01)

(52) U.S. Cl.
CPC .................................. *C12N 15/8213* (2013.01)

(58) Field of Classification Search
USPC ............... 800/278, 287; 435/412, 415, 320.1
See application file for complete search history.

(56) References Cited

U.S. PATENT DOCUMENTS

| | | | |
|---|---|---|---|
| 5,789,538 A | 8/1998 | Rebar et al. | |
| 5,925,523 A | 7/1999 | Dove et al. | |
| 6,187,994 B1 * | 2/2001 | Baszczynski et al. | 800/278 |
| 6,200,759 B1 | 3/2001 | Dove et al. | |
| 6,410,248 B1 | 6/2002 | Greisman et al. | |
| 6,453,242 B1 | 9/2002 | Eisenberg et al. | |
| 6,528,313 B1 | 3/2003 | Le Mouellic et al. | |
| 6,534,261 B1 | 3/2003 | Cox, III et al. | |
| 6,794,136 B1 | 9/2004 | Eisenberg et al. | |
| 2005/0026157 A1 | 2/2005 | Baltimore et al. | |
| 2005/0064474 A1 | 3/2005 | Urnov et al. | |
| 2005/0208489 A1 | 9/2005 | Carroll et al. | |

FOREIGN PATENT DOCUMENTS

| | | |
|---|---|---|
| WO | WO 9519431 A1 | 7/1995 |
| WO | WO 9837186 A1 | 8/1998 |
| WO | WO 9853057 A1 | 11/1998 |
| WO | WO 0153480 A1 | 8/2001 |
| WO | WO 03080809 A3 | 2/2003 |
| WO | WO 2005014791 A3 | 2/2005 |
| WO | WO 2005084190 A3 | 9/2005 |

OTHER PUBLICATIONS

Bibikova et al., Stimulation of Homologous Recombination through Trageted Cleavage by Chimeric Nucleases, 2001 Mol. Cell. Biology 21:289-297.*
Wright et al. High-frequency homologous recombinaiton in plants mediated by zinc-finger nucleases, 2005, Plant Jopurnal 44:693-705.*
Bibikova et al. Stimulatiom of Homologous Recombination through Targeted Cleavage by Chirmeric Nucleases, 2001, Mol. Cell. Biology 21:289-297.*
Wright et al (2005, The Plant Journal 44:693-705).*
Pabo et al (2001, Annu. Rev. Biochem. 70:313-340).*
Wright et al (2005, The Plant Journal 44:693-705.*
Corrigan-Curay et al (2015, Molecular Therapy 23 (5): 796-806).*
Ramirez et al (2008, Nature Methods 5 (5): 374-375).*
Townsend et al (2009, Nature Letters 459 (May): 442-446).*
Beerli et al. (2002) Nature Biotechnol. 20:135-141.
Bibikova et al. (2001) Mol. Cell. Biol. 21:289-297.
Capecchi (1989) Science 244:1288-1292.
Choo et al. (2000) Curr. Opin. Struct. Biol. 10:411-416.
Choulika et al. (1995) Mol. Cell. Biol. 15:1968-1973.
Isalan et al. (2001) Nature Biotechnol. 19:656-660.
Johnson et al. (2001) Biochem. Soc. Trans. 29:196-201.
Pabo et al. (2001) Ann. Rev. Biochem. 70:313-340.
Puchta et al. (1996) PNAS 93:5055-5060.
Seibert et al. (2002) Plant Cell 14:1121-1131.
Segal et al. (2001) Curr. Opin. Biotechnol. 12:632-637.
Smith et al. (2000) Nucleic Acids Res. 28:3361-3369.
Urnov et al. (2005) Nature 435: 646-651.
Wright et al. (2005) Plant Journal 44:693-705.
Yanez et al. (1998) Gene Therapy 5:149-159.

* cited by examiner

*Primary Examiner* — Stuart F Baum
(74) *Attorney, Agent, or Firm* — Pasternak Patent Law

(57) ABSTRACT

Disclosed herein are methods and compositions for targeted integration of an exogenous sequence into a predetermined target site in a plant genome.

6 Claims, 22 Drawing Sheets

Target Vector (pDAB1585)

Figure 2A
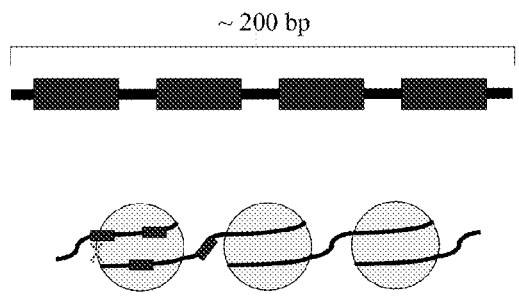
Figure 2B
```
                IL-1                                    Scd27
      ATTATCCGAGTTTAATAGAACTCGGATAAT          CGAGTTCTTGTACACCAGTACAAGAACTCG
      TAATAGGCTCAAATTATCTTGAGCCTATTA          GCTCAAGAACATGTGGTCATGTTCTTGAGC
                IL-1                                    Scd27
```
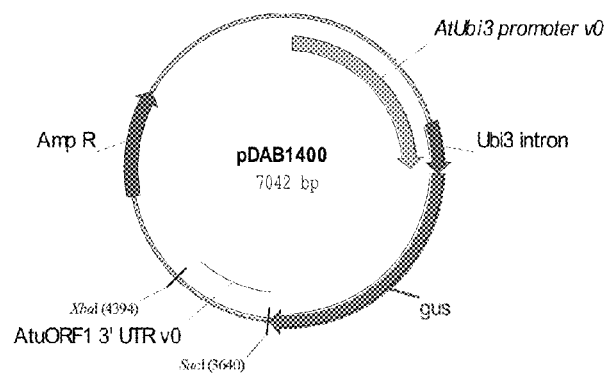
Figure 3

Figure 26A
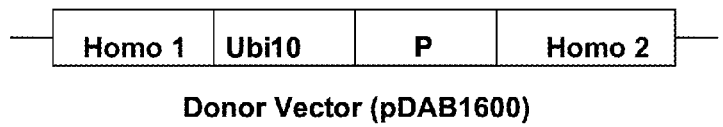
Donor Vector (pDAB1600)
Figure 26B
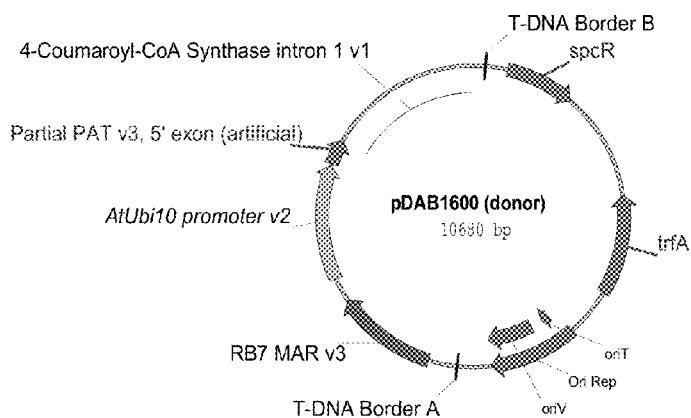
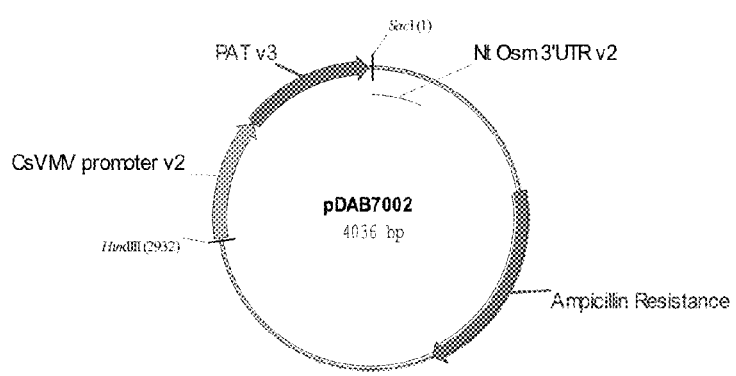
Figure 27

ZFN Vectors (pDAB1596, pDAB1598)

Positive Control Vector (pDAB1601)

ZINC FINGER NUCLEASE-MEDIATED HOMOLOGOUS RECOMBINATION

TECHNICAL FIELD

The present disclosure is in the fields of genome engineering, gene targeting, targeted chromosomal integration and protein expression in plants.

BACKGROUND

A major area of interest in agriculture, especially in light of the determination of the complete nucleotide sequences of a number of plant genomes, is the targeted alteration of genome sequences. In particular, the ability to convert endogenous plant sequences would facilitate numerous applications such as, for example, the optimization of crop traits affecting nutritional value, yield, stress tolerance, pathogen resistance, and resistance to agrochemicals and/or the adaptation of plants for use as biological factories for the production of pharmaceutical compounds or industrial chemicals.

In eukaryotes, attempts have been made to alter genomic sequences in cultured cells by taking advantage of the natural phenomenon of homologous recombination. See, for example, Capecchi (1989) *Science* 244:1288-1292; U.S. Pat. Nos. 6,528,313 and 6,528,314. If a polynucleotide has sufficient homology to the genomic region containing the sequence to be altered, it is possible for part or all of the sequence of the polynucleotide to replace the genomic sequence by homologous recombination. However, the frequency of homologous recombination under these circumstances is extremely low. Moreover, the frequency of insertion of the exogenous polynucleotide at genomic locations that lack sequence homology exceeds the frequency of homologous recombination by several orders of magnitude.

The introduction of a double-stranded break into genomic DNA, in the region of the genome bearing homology to an exogenous polynucleotide, has been shown to stimulate homologous recombination at this site by several thousand-fold in cultured cells. Rouet et al. (1994) *Mol. Cell. Biol.* 14:8096-8106; Choulika et al. (1995) *Mol. Cell. Biol.* 15:1968-1973; Donoho et al. (1998) *Mol. Cell. Biol.* 18:4070-4078. See also Johnson et al. (2001) *Biochem. Soc. Trans.* 29:196-201; and Yanez et al. (1998) *Gene Therapy* 5:149-159. In these methods, DNA cleavage in the desired genomic region was accomplished by inserting a recognition site for a meganuclease (i.e., an endonuclease whose recognition sequence is so large that it does not occur, or occurs only rarely, in the genome of interest) into the desired genomic region.

However, meganuclease cleavage-stimulated homologous recombination relies on either the fortuitous presence of, or the directed insertion of, a suitable meganuclease recognition site in the vicinity of the genomic region to be altered. Since meganuclease recognition sites are rare (or nonexistent) in a typical plant genome, and insertion of a suitable meganuclease recognition site is plagued with the same difficulties as associated with other genomic alterations, these methods are not broadly applicable.

Thus, there remain needs for compositions and methods for targeted alteration of sequences in any plant genome and for compositions and methods for targeted introduction of exogenous sequences into a genome.

SUMMARY

The present disclosure provides compositions and methods for targeted cleavage of cellular chromatin in a region of interest and/or homologous recombination at a predetermined region of interest in plant cells. Plant cells can be from monocotyledonous (monocots) or dicotyledonous (dicots) plant species and also include cultured cells, cells in a plant at any stage of development, and plant cells that have been removed from a whole plant and which cells (or their descendants) will be returned to the plant.

A region of interest in cellular chromatin can be, for example, a genomic sequence or portion thereof. Compositions include fusion polypeptides comprising an engineered zinc finger binding domain (e.g., a zinc finger binding domain having a novel specificity) and a cleavage domain, and fusion polypeptides comprising an engineered zinc finger binding domain and a cleavage half-domain. Cleavage domains and cleavage half domains can be obtained, for example, from various restriction endonucleases and/or homing endonucleases.

In one aspect, described herein is a vector comprising first and second DNA sequences, wherein (i) the first sequence is homologous to a third sequence and the second sequence is homologous to a fourth sequence; (ii) the third and fourth sequences are chromosomal DNA sequences; and (iii) the near edges of third and fourth sequences are separated by at least 1 nucleotide pair. In certain embodiments, the third and fourth sequences are endogenous sequences.

In any of the vectors described herein, at least one of the first or second sequences has a length of 100 nucleotides. In addition, any of the vectors described herein may further comprise a fifth sequence, wherein the fifth sequence: (a) is interposed between the first and second sequences; and (b) is an exogenous sequence. In certain embodiments, the fifth sequence has a size of at least 1 base pair but may be as large as 22 kilobase pairs.

The vectors (e.g., the fifth sequence) may also comprise sequences encoding a protein or portions of a protein. In certain embodiments, the protein-encoding sequence encodes a selectable marker (e.g., green fluorescent protein (GFP), (β-glucuronidase (GUS), phosphinothricin N-acetyl transferase (PAT, BAR), neomycin phosphotransferase, β-lactamase, catechol dioxygenase, α-amylase, tyrosinase, β-galactosidase, luciferase, aequorin, EPSP synthase, nitrilase, acetolactate synthase (ALS), dihydrofolate reductase (DHFR), dalapon dehalogenase and anthranilate synthase). In other embodiments, the protein-encoding sequence (e.g., the fifth sequence) encodes a protein or portion of protein, for example a sequence that is homologous to chromosomal sequences.

In still other embodiments, the vectors (e.g., the fifth sequence) comprise one or more transcriptional regulatory sequences. In still further embodiments, the vectors (e.g., fifth sequence) may comprise a wild-type counterpart of a mutant chromosomal sequence or, alternatively, a mutant counterpart of a wild-type chromosomal sequence.

In any of the vectors described herein, the first sequence may have at least 35% homology to the third sequence. Similarly, in any of the vectors described herein, the second sequence may have at least 35% homology to the fourth sequence. In some embodiments the first sequence has at least 35% to 50%, at least 50% to 70%, at least 70% to 80%, at least 80% to 85%, at least 85% to 90%, at least 90% to 95%, at least 95%, 96%, 97%, 98%, 99% or 100% homology to the third sequence. In some embodiments the second sequence has at least 35% to 50%, at least 50% to 70%, at least 70% to 80%, at least 80% to 85%, at least 85% to 90%, at least 90% to 95%, at least 95%, 96%, 97%, 98%, 99% or 100% homology to the fourth sequence.

In yet another aspect, described herein is a method for introducing an exogenous sequence into the genome of a plant cell, the method comprising the steps of: (a) contacting the cell with any of the vectors described above; and (b) expressing one or more nucleases in the cell, wherein the one or more nucleases cleave chromosomal DNA within between 0.4 and 3 kilobase pairs of either of the third or fourth sequences; such that cleavage of chromosomal DNA in step (b) stimulates incorporation of the targeting vector into the genome by homologous recombination. In certain embodiments, the one or more nucleases are fusions between the cleavage domain of a Type IIS restriction endonuclease and an engineered zinc finger binding domain.

In yet another aspect, provided herein is a method for expressing a protein in a plant cell, the method comprising the steps of: (a) contacting the cell with a vector as described herein; and (b) expressing one or more nucleases in the cell, wherein the one or more nucleases cleave chromosomal DNA within between 0.1 and 3 kilobase pairs of either of the third or fourth sequences; such that cleavage of chromosomal DNA in step (b) stimulates incorporation of the vector into the genome by homologous recombination. In certain embodiments, one or more nucleases are fusions between the cleavage domain of a Type IIS restriction endonuclease and an engineered zinc finger binding domain.

In another aspect, described herein is a targeting vector comprising: (a) first and second coding sequences; and (b) first, second and third target sequences; wherein the sequences are arranged in the order: first target sequence, first coding sequence, second target sequence, second coding sequence, third target sequence; further wherein the first target sequence is homologous to a first chromosomal sequence and the third target sequence is homologous to a second chromosomal sequence. The first and/or second coding sequence can encode a selectable marker or, alternatively, the first and/or second coding sequence can encode a protein that is not a selectable marker. The first and second chromosomal sequences may be endogenous chromosomal sequences. Furthermore, the vectors may comprise one or more repeats of the first, second and/or third target sequence.

In another aspect, a method for introducing an exogenous sequence into the genome of a plant cell is provided, the method comprising the steps of: (a) contacting the cell with a targeting vector as described in the preceding paragraph; and (b) expressing one or more nucleases in the cell, wherein the one or more nucleases cleave chromosomal DNA within between 0.1 and 3 kilobase pairs of either of the first or second chromosomal sequences; such that cleavage of chromosomal DNA in step (b) stimulates incorporation of the targeting vector into the genome by homologous recombination. In certain embodiments, the one or more nucleases comprise a cleavage half-domain; for example, the nuclease is a fusion between the cleavage domain of a Type IIS restriction endonuclease and an engineered zinc finger binding domain.

In another aspect, a method for expressing a protein in a plant cell is provided, the method comprising the steps of: (a) contacting the cell with a targeting vector as described two paragraphs above; and (b) expressing one or more nucleases in the cell, wherein the one or more nucleases cleave chromosomal DNA within between 0.1 and 3 kilobase pairs of either of the first or second chromosomal sequences; such that cleavage of chromosomal DNA in step (b) stimulates incorporation of the targeting vector into the genome by homologous recombination. In certain embodiments, one or more nucleases are fusions between the cleavage domain of a Type IIS restriction endonuclease and an engineered zinc finger binding domain.

In a still further aspect, a transgenic plant cell obtained according to any of the methods described herein is also provided.

In another aspect, provided herein is a plant comprising a transgenic plant cell obtained as described herein.

Also provided is a method for deleting sequences from the genome of a transgenic plant cell comprising first and second coding sequences; and first, second and third target sequences; wherein the sequences are arranged in the order: first target sequence, first coding sequence, second target sequence, second coding sequence, third target sequence, wherein the method comprises: (a) providing a transgenic plant cell as described herein; and (b) expressing first and second nucleases in the cell, wherein the first nuclease cleaves in the first target sequence and the second nuclease cleaves in the second target sequence.

In a further aspect, disclosed herein is a method for deleting sequences from the genome of a transgenic plant cell comprising first and second coding sequences; and first, second and third target sequences; wherein the sequences are arranged in the order: first target sequence, first coding sequence, second target sequence, second coding sequence, third target sequence, wherein the method comprises: (a) providing a transgenic plant cell as described herein; and (b) expressing first and second nucleases in the cell, wherein the first nuclease cleaves in the second target sequence and the second nuclease cleaves in the third target sequence.

In yet another aspect, provided herein is a method for deleting sequences from the genome of a transgenic plant cell comprising first and second coding sequences; and first, second and third target sequences; wherein the sequences are arranged in the order: first target sequence, first coding sequence, second target sequence, second coding sequence, third target sequence, wherein the method comprises: (a) providing a transgenic plant cell as described herein; and (b) expressing first and second nucleases in the cell, wherein the first nuclease cleaves in the first target sequence and the second nuclease cleaves in the third target sequence.

In another aspect, a method for intramolecular homologous recombination in the genome of a cell (e.g., plant cell) is provided, the method comprising the steps of (a) providing a DNA segment comprising a first sequence that is homologous to a second sequence; and (b) contacting said DNA segment with a nuclease, wherein the nuclease cleaves the DNA segment at a third sequence. In certain embodiments, the DNA segment is endogenous to the cell. In certain embodiments, homologous recombination occurs in a chromosome, for example, when DNA between the first and second sequences is deleted from the chromosome. The sequences deleted from the chromosome may encode, for example, all or part of a selectable marker. The deleted DNA may be replaced by an exogenous sequence, for example wherein the method further comprises: introducing a polynucleotide into the cell, wherein the polynucleotide comprises: (a) fourth and fifth sequences, wherein the fourth sequence is homologous to non-deleted sequences in proximity to the first sequence and the fifth sequence is homologous to non-deleted sequences in proximity to the second sequence; and (b) the exogenous sequence (e.g., a selectable marker, a protein or portion of a protein other than a selectable marker, an RNA such as siRNA, etc.). In any of the methods provided herein, the selectable marker may be, for example, green fluorescent protein (GFP), β-glucuronidase (GUS), phosphinothricin N-acetyl transferase (PAT, BAR), neomycin phosphotransferase, β-lactamase, catechol dioxygenase, α-amylase, tyrosinase, β-galactosidase, luciferase, aequorin, EPSP synthase, nitrilase, acetolactate synthase (ALS), dihydrofolate reductase (DHFR), dalapon dehalogenase and anthranilate synthase.

In any of the methods, the third sequence (i.e., the sequence cleaved by the nuclease) may be unique in the genome and/or the nuclease may be a pair of fusion proteins, wherein each fusion protein is a fusion between a cleavage half-domain (for example the cleavage domain of a Type IIS restriction endonuclease) and an engineered zinc finger binding domain. Furthermore, the third sequence may be between the first and second sequences (i.e., the homologous sequences) and/or at least 1 base pair from the first and/or second sequences.

In any of the methods described herein, one or both of the first and second sequences may be exogenous to the organism.

Thus, the present disclosure encompasses, but is not limited to, the following numbered embodiments:

1. A donor vector comprising first and second DNA sequences;
wherein the first sequence is homologous to a third sequence and the second sequence is homologous to a fourth sequence;
wherein the third and fourth sequences are chromosomal DNA sequences; and
wherein the near edges of third and fourth sequences are separated by at least 1 nucleotide pair.

2. The vector of 1, wherein the third and fourth sequences are endogenous sequences.

3. The vector of 1 or 2, wherein at least one of the first or second sequences has a length of 100 nucleotides.

4. The vector of any of 1 to 3, further comprising a fifth sequence, wherein the fifth sequence:
(a) is interposed between the first and second sequences; and
(b) is an exogenous sequence.

5. The vector of 4, wherein the fifth sequence has a size of at least 1 base pair.

6. The vector of 4, wherein the fifth sequence comprises sequences encoding a selectable marker.

7. The vector of 6, wherein the selectable marker is selected from the group consisting of green fluorescent protein (GFP), β-glucuronidase (GUS), phosphinothricin N-acetyl transferase (PAT, BAR), neomycin phosphotransferase, β-lactamase, catechol dioxygenase, α-amylase, tyrosinase, β-galactosidase, luciferase, aequorin, EPSP synthase, nitrilase, acetolactate synthase (ALS), dihydrofolate reductase (DHFR), dalapon dehalogenase and anthranilate synthase.

8. The vector of 4, wherein the fifth sequence comprises sequences encoding a protein other than a selectable marker.

9. The vector of 4, wherein the fifth sequence comprises one or more transcriptional regulatory sequences.

10. The vector of 4, wherein the fifth sequence comprises sequences encoding a portion of a protein.

11. The vector of 10, wherein the sequences encoding the portion of the protein comprise sequences homologous to chromosomal sequences.

12. The vector of 4, wherein the fifth sequence comprises a wild-type counterpart of a mutant chromosomal sequence.

13. The vector of 4, wherein the fifth sequence comprises a mutant counterpart of a wild-type chromosomal sequence.

14. The vector of any of 1 to 13, wherein the first sequence has at least 35% homology to the third sequence.

15. The vector of 1 to 14, wherein the second sequence has at least 35% homology to the fourth sequence.

16. The vector of 14, wherein the second sequence has at least 35% homology to the fourth sequence.

17. A method for introducing an exogenous sequence into the genome of a plant cell, the method comprising the steps of:
(a) contacting the cell with a targeting vector according to any of 1 to 16; and
(b) expressing one or more nucleases in the cell, wherein the one or more nucleases cleave chromosomal DNA within 3 kilobase pairs of either of the third or fourth sequences;
such that cleavage of chromosomal DNA in step (b) stimulates incorporation of the targeting vector into the genome by homologous recombination.

18. The method of 17, wherein the one or more nucleases are fusions between the cleavage domain of a Type IIS restriction endonuclease and an engineered zinc finger binding domain.

19. A method for expressing a protein in a plant cell, the method comprising the steps of
(a) contacting the cell with a targeting vector according to 8; and
(b) expressing one or more nucleases in the cell, wherein the one or more nucleases cleave chromosomal DNA within 3 kilobase pairs of either of the third or fourth sequences;
such that cleavage of chromosomal DNA in step (b) stimulates incorporation of the targeting vector into the genome by homologous recombination.

20. The method of 19, wherein the one or more nucleases are fusions between the cleavage domain of a Type IIS restriction endonuclease and an engineered zinc finger binding domain.

21. A transgenic plant cell obtained according to the method of 17, 18, 19 or 20.

22. A plant comprising a transgenic plant cell according to 21.

23. A method for intramolecular homologous recombination in the genome of a cell, the method comprising the steps of
(a) providing a DNA segment comprising a first sequence that is homologous to a second sequence; and
(b) contacting said DNA segment with a nuclease, wherein the nuclease cleaves the DNA segment at a third sequence.

24. The method of 23, wherein the DNA segment is endogenous to the cell.

25. The method of 23 or 24, wherein the homologous recombination occurs in a chromosome.

26. The method of 25, wherein DNA between the first and second sequences is deleted from the chromosome.

27. The method of 23, 24, 25 or 26, wherein the third sequence is unique in the genome.

28. The method of any of 23 to 26, wherein the cell is a plant cell.

29. The method of any of 23 to 28, wherein the nuclease is a pair of fusion proteins, wherein each fusion protein is a fusion between the cleavage domain of a Type IIS restriction endonuclease and an engineered zinc finger binding domain.

30. The method of any of 23 to 29, wherein the third sequence is at least 100 base pairs from the first sequence.

31. The method of any of 23 to 30, wherein the third sequence is at least 100 base pairs from the second sequence.

32. The method of any of 23 to 31, wherein the third sequence lies between the first and second sequences.

33. The method of any of 23 to 32, wherein one of the first or second sequences is exogenous to the organism.

34. The method of any of 23 to 32, wherein both of the first and second sequences are exogenous to the organism.

35. The method of 26, wherein the sequences deleted from the chromosome encode all or part of a selectable marker.

36. The method of 35, wherein the selectable marker is selected from the group consisting of green fluorescent protein (GFP), β-glucuronidase (GUS), phosphinothricin N-acetyl transferase (PAT, BAR), neomycin phosphotransferase, β-lactamase, catechol dioxygenase, α-amylase, tyrosinase, β-galactosidase, luciferase, aequorin, EPSP synthase, nitrilase, acetolactate synthase (ALS), dihydrofolate reductase (DHFR), dalapon dehalogenase and anthranilate synthase.

37. The method of 26, wherein the deleted DNA is replaced by an exogenous sequence, the method further comprising:
    introducing a polynucleotide into the cell, wherein the polynucleotide comprises:
    (a) fourth and fifth sequences, wherein the fourth sequence is homologous to non-deleted sequences in proximity to the first sequence and the fifth sequence is homologous to non-deleted sequences in proximity to the second sequence; and
    (b) the exogenous sequence.

38. The method of 37 wherein the exogenous sequence is a selectable marker.

39. The method of 38, wherein the selectable marker is selected from the group consisting of green fluorescent protein (GFP), β-glucuronidase (GUS), phosphinothricin N-acetyl transferase (PAT, BAR), neomycin phosphotransferase, β-lactamase, catechol dioxygenase, α-amylase, tyrosinase, β-galactosidase, luciferase, aequorin, EPSP synthase, nitrilase, acetolactate synthase (ALS), dihydrofolate reductase (DHFR), dalapon dehalogenase and anthranilate synthase.

40. The method of any of 23 to 39, wherein the exogenous sequence encodes a protein other than a selectable marker.

41. The method of any of 23 to 39, wherein the exogenous sequence encodes a RNA.

42. The method of 41, wherein the RNA is a siRNA.

43. A targeting vector comprising:
    (a) first and second coding sequences; and
    (b) first, second and third target sequences;
    wherein the sequences are arranged in the order: first target sequence, first coding sequence, second target sequence, second coding sequence, third target sequence;
    further wherein the first target sequence is homologous to a first chromosomal sequence and the third target sequence is homologous to a second chromosomal sequence.

44. The vector of 43, wherein the first coding sequence encodes a selectable marker.

45. The vector of 43 or 44, wherein the second coding sequence encodes a selectable marker.

46. The vector of 43 or 45, wherein the first coding sequence encodes a protein that is not a selectable marker.

47. The vector of 43, 44 or 46, wherein the second coding sequence encodes a protein that is not a selectable marker.

48. The vector of any of 43 to 47, wherein the first and second chromosomal sequences are endogenous chromosomal sequences.

49. The vector of any of 43 to 48, further comprising one or more repeats of the first target sequence.

50. The vector of any of 43 to 49, further comprising one or more repeats of the second target sequence.

51. The vector of any of 43 to 50, further comprising one or more repeats of the third target sequence.

52. A method for introducing an exogenous sequence into the genome of a plant cell, the method comprising the steps of:
    (a) contacting the cell with a targeting vector according to any of claims 43 to 51; and
    (b) expressing one or more nucleases in the cell, wherein the one or more nucleases cleave chromosomal DNA within between 0.1 and 3 kilobase pairs of either of the first or second chromosomal sequences;
    such that cleavage of chromosomal DNA in step (b) stimulates incorporation of the targeting vector into the genome by homologous recombination.

53. The method of 52, wherein the one or more nucleases are fusions between the cleavage domain of a Type IIS restriction endonuclease and an engineered zinc finger binding domain.

54. A method for expressing a protein in a plant cell, the method comprising the steps of
    (a) contacting the cell with a targeting vector according to any of 43 to 51; and
    (b) expressing one or more nucleases in the cell, wherein the one or more nucleases cleave chromosomal DNA within between 0.1 and 3 kilobase pairs of either of the first or second chromosomal sequences;
    such that cleavage of chromosomal DNA in step (b) stimulates incorporation of the targeting vector into the genome by homologous recombination.

55. The method of claim 54, wherein the one or more nucleases are fusions between the cleavage domain of a Type IIS restriction endonuclease and an engineered zinc finger binding domain.

56. A transgenic plant cell obtained according to the method of 52 or 53.

57. A plant comprising a transgenic plant cell according to 56.

58. A method for deleting sequences from the genome of a transgenic plant cell wherein the method comprises:
    (a) providing a transgenic plant cell according to 56; and
    (b) expressing first and second nucleases in the cell, wherein the first nuclease cleaves in the first target sequence and the second nuclease cleaves in the second target sequence.

59. A method for deleting sequences from the genome of a transgenic plant cell wherein the method comprises:
    (a) providing a transgenic plant cell according to 56; and
    (b) expressing first and second nucleases in the cell, wherein the first nuclease cleaves in the second target sequence and the second nuclease cleaves in the third target sequence.

60. A method for deleting sequences from the genome of a transgenic plant cell wherein the method comprises:
    (a) providing a transgenic plant cell according to 56; and
    (b) expressing first and second nucleases in the cell, wherein the first nuclease cleaves in the first target sequence and the second nuclease cleaves in the third target sequence.

BRIEF DESCRIPTION OF THE DRAWINGS

FIG. 1A is a linear depiction of various elements of the construct. FIG. 1B is a depiction of the circular construct.

FIGS. 2A and 2B depict exemplary ZFNs and their target sites. FIG. 2A depicts the ZFNs and the binding regions. FIG. 2B depicts the target sites for IL-1 (SEQ ID NO:2) and Scd27 (SEQ ID NO:3).

FIG. 3 is a schematic representation of the plasmid pDAB1400.

FIGS. 26A and 26B are schematic representations of the targeting plasmid vector designated pDAB1600. FIG. 26A is a linear depiction of various elements of the plasmid. FIG. 26B is a depiction of the circular plasmid.

FIG. 27 is a schematic representation of the plasmid pDAB7002.

FIG. 34A is a schematic of the linearized plasmids. FIG. 34B shows pDAB1596. FIG. 34C shows pDAB1598.

FIG. 37A shows various elements in linear form. FIG. 37B shows the circular plasmid.

DETAILED DESCRIPTION

Figure 1A:
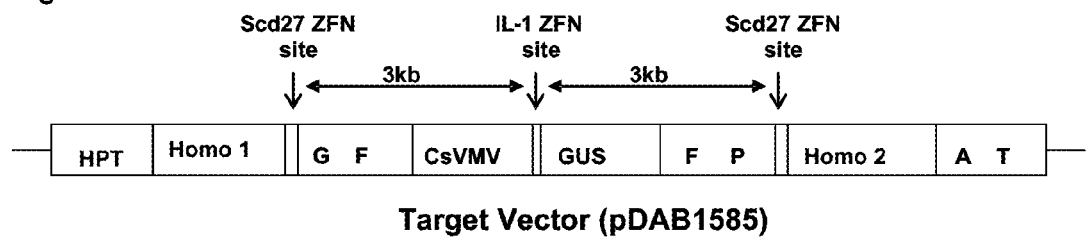
FIGS. 1A and 1B are schematic representations of the targeting construct designated pDAB1585.

Disclosed herein are compositions and methods useful for targeted cleavage of plant cellular chromatin and for targeted alteration of a plant cellular nucleotide sequence, e.g., by targeted cleavage followed by intrachromosomal homologous recombination or by targeted cleavage followed by homologous recombination between an exogenous polynucleotide (comprising one or more regions of homology with the cellular nucleotide sequence) and a genomic sequence.

Genomic sequences include those present in chromosomes, episomes, organellar genomes (e.g., mitochondria, chloroplasts), artificial chromosomes and any other type of nucleic acid present in a cell such as, for example, amplified sequences, double minute chromosomes and the genomes of endogenous or infecting bacteria and viruses. Genomic sequences can be normal (i.e., wild-type) or mutant; mutant sequences can comprise, for example, insertions, deletions, translocations, rearrangements, and/or point mutations. A genomic sequence can also comprise one of a number of different alleles.

Compositions useful for targeted cleavage and recombination include fusion proteins comprising a cleavage domain (or a cleavage half-domain) and a zinc finger binding domain, polynucleotides encoding these proteins and combinations of polypeptides and polypeptide-encoding polynucleotides. A zinc finger binding domain can comprise one or more zinc fingers (e.g., 2, 3, 4, 5, 6, 7, 8, 9 or more zinc fingers), and can be engineered to bind to any genomic sequence. Thus, by identifying a target genomic region of interest at which cleavage or recombination is desired, one can, according to the methods disclosed herein, construct one or more fusion proteins comprising a cleavage domain (or cleavage half-domain) and a zinc finger domain engineered to recognize a target sequence in said genomic region. The presence of such a fusion protein (or proteins) in a cell will result in binding of the fusion protein(s) to its (their) binding site(s) and cleavage within or near said genomic region. Moreover, if an exogenous polynucleotide homologous to the genomic region is also present in such a cell, homologous recombination occurs at a high rate between the genomic region and the exogenous polynucleotide.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

Definitions

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

Zinc finger binding domains can be "engineered" to bind to a predetermined nucleotide sequence. Non-limiting examples of methods for engineering zinc finger proteins are design and selection. A designed zinc finger protein is a protein not occurring in nature whose design/composition results principally from rational criteria. Rational criteria for design include application of substitution rules and computerized algorithms for processing information in a database storing information of existing ZFP designs and binding data. See, for example, U.S. Pat. Nos. 6,140,081; 6,453,242; 6,534,261; and 6,785,613; see, also WO 98/53058; WO 98/53059; WO 98/53060; WO 02/016536 and WO 03/016496; and U.S. Pat. Nos. 6,746,838; 6,866,997; and 7,030,215.

A "selected" zinc finger protein is a protein not found in nature whose production results primarily from an empirical process such as phage display, interaction trap or hybrid selection. See e.g., U.S. Pat. Nos. 5,789,538; 5,925,523; 6,007,988; 6,013,453; 6,200,759; 6,733,970; US RE39,229; and WO 95/19431; WO 96/06166; WO 98/53057; WO 98/54311; WO 00/27878; WO 01/60970 WO 01/88197 and WO 02/099084.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 25,000 nucleotides in length (or any integer value therebetween or thereabove), preferably between about 100 and 5,000 nucleotides in length (or any integer therebetween), more preferably between about 200 and 2,500 nucleotides in length.

A "homologous sequence" refers to a first sequence which shares a degree of sequence identity with a second sequence, and whose sequence may be identical to that of the second sequence. A "homologous, non-identical sequence" refers to a first sequence which shares a degree of sequence identity with a second sequence, but whose sequence is not identical to that of the second sequence. For example, a polynucleotide comprising the wild-type sequence of a mutant gene is homologous and non-identical to the sequence of the mutant gene. In certain embodiments, the degree of homology between the two sequences is sufficient to allow homologous recombination therebetween, utilizing normal cellular mechanisms. Two homologous non-identical sequences can be any length and their degree of non-homology can be as small as a single nucleotide (e.g., for correction of a genomic point mutation by targeted homologous recombination) or as large as 10 or more kilobases (e.g., for insertion of a gene at a predetermined site in a chromosome). Two polynucleotides comprising the homologous non-identical sequences need not be the same length. For example, an exogenous polynucleotide (i.e., donor polynucleotide) of between 20 and 10,000 nucleotides or nucleotide pairs can be used.

Techniques for determining nucleic acid and amino acid sequence identity are known in the art. Typically, such techniques include determining the nucleotide sequence of the mRNA for a gene and/or determining the amino acid sequence encoded thereby, and comparing these sequences to a second nucleotide or amino acid sequence. Genomic sequences can also be determined and compared in this fashion. In general, identity refers to an exact nucleotide-to-nucleotide or amino acid-to-amino acid correspondence of two polynucleotides or polypeptide sequences, respectively. Two or more sequences (polynucleotide or amino acid) can be compared by determining their percent identity. The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, *Advances in Applied Mathematics* 2:482-489 (1981). This algorithm can be applied to amino acid sequences by using the scoring matrix developed by Dayhoff, *Atlas of Protein Sequences and Structure*, M. O. Dayhoff ed., 5 suppl. 3:353-358, National Biomedical Research Foundation, Washington, D.C., USA, and normalized by Gribskov, *Nucl. Acids Res.* 14(6):6745-6763 (1986). An exemplary implementation of this algorithm to determine percent identity of a sequence is provided by the Genetics Computer Group (Madison, Wis.) in the "BestFit" utility application. The default parameters for this method are described in the Wisconsin Sequence Analysis Package Program Manual, Version 8 (1995) (available from Genetics Computer Group, Madison, Wis.). A preferred method of establishing percent identity in the context of the present disclosure is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects sequence identity. Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+ PDB+GenBank CDS translations+Swiss protein+Spupdate+ PIR. Details of these programs can be found on the internet. With respect to sequences described herein, the range of desired degrees of sequence identity is approximately 35% to 100% and any integer value therebetween. Typically the percent identities between sequences are at least 35%-40%; 40%-45%; 45%-50%; 50%-60%; 60%-70%; 70-75%, preferably 80-82%, more preferably 85-90%, even more preferably 92%, still more preferably 95%, and most preferably 98% sequence identity.

Alternatively, the degree of sequence similarity between polynucleotides can be determined by hybridization of polynucleotides under conditions that allow formation of stable duplexes between homologous regions, followed by digestion with single-stranded-specific nuclease(s), and size determination of the digested fragments. Two nucleic acid, or two polypeptide sequences are substantially homologous to each other when the sequences exhibit at least about 70%-75%, preferably 80%-82%, more preferably 85%-90%, even more preferably 92%, still more preferably 95%, and most preferably 98% sequence identity over a defined length of the molecules, as determined using the methods above. As used herein, substantially homologous also refers to sequences showing complete identity to a specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *Nucleic Acid Hybridization: A Practical Approach*, editors B. D. Hames and S. J. Higgins, (1985) Oxford; Washington, D.C.; IRL Press).

Selective hybridization of two nucleic acid fragments can be determined as follows. The degree of sequence identity between two nucleic acid molecules affects the efficiency and strength of hybridization events between such molecules. A partially identical nucleic acid sequence will at least partially inhibit the hybridization of a completely identical sequence to a target molecule. Inhibition of hybridization of the completely identical sequence can be assessed using hybridization assays that are well known in the art (e.g., Southern (DNA) blot, Northern (RNA) blot, solution hybridization, or the like, see Sambrook, et al., *Molecular Cloning: A Laboratory Manual*, Second Edition, (1989) Cold Spring Harbor, N.Y.). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a reference nucleic acid sequence, and then by selection of appropriate conditions the probe and the reference sequence selectively hybridize, or bind, to each other to form a duplex molecule. A nucleic acid molecule that is capable of hybridizing selectively to a reference sequence under moderately stringent hybridization conditions typically hybridizes under conditions that allow detection of a target nucleic acid sequence of at least about 10-14 nucleotides in length having at least approximately 70% sequence identity with the sequence of the selected nucleic acid probe. Stringent hybridization conditions typically allow detection of target nucleic acid sequences of at least about 10-14 nucleotides in length having a sequence identity of greater than about 90-95% with the sequence of the selected nucleic acid probe. Hybridization conditions useful for probe/reference sequence hybridization, where the probe and reference sequence have a specific degree of sequence identity, can be determined as is known in the art (see, for example, *Nucleic Acid Hybridization: A Practical Approach*, editors B. D. Hames and S. J. Higgins, (1985) Oxford; Washington, D.C.; IRL Press).

Conditions for hybridization are well-known to those of skill in the art. Hybridization stringency refers to the degree to which hybridization conditions disfavor the formation of hybrids containing mismatched nucleotides, with higher stringency correlated with a lower tolerance for mismatched hybrids. Factors that affect the stringency of hybridization are well-known to those of skill in the art and include, but are not limited to, temperature, pH, ionic strength, and concentration of organic solvents such as, for example, formamide and dimethylsulfoxide. As is known to those of skill in the art, hybridization stringency is increased by higher temperatures, lower ionic strength and lower solvent concentrations.

With respect to stringency conditions for hybridization, it is well known in the art that numerous equivalent conditions can be employed to establish a particular stringency by varying, for example, the following factors: the length and nature of the sequences, base composition of the various sequences, concentrations of salts and other hybridization solution components, the presence or absence of blocking agents in the hybridization solutions (e.g., dextran sulfate, and polyethylene glycol), hybridization reaction temperature and time parameters, as well as, varying wash conditions. The selection of a particular set of hybridization conditions is selected following standard methods in the art (see, for example, Sambrook, et al., *Molecular Cloning: A Laboratory Manual*, Second Edition, (1989) Cold Spring Harbor, N.Y.).

"Recombination" refers to a process of exchange of genetic information between two polynucleotides. For the purposes of this disclosure, "homologous recombination (HR)" refers to the specialized form of such exchange that takes place, for example, during repair of double-strand breaks in cells. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage domain" comprises one or more polypeptide sequences which possesses catalytic activity for DNA cleavage. A cleavage domain can be contained in a single polypeptide chain or cleavage activity can result from the association of two (or more) polypeptides.

A "cleavage half-domain" is a polypeptide sequence which, in conjunction with a second polypeptide (either identical or different) forms a complex having cleavage activity (preferably double-strand cleavage activity).

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

An "accessible region" is a site in cellular chromatin in which a target site present in the nucleic acid can be bound by an exogenous molecule which recognizes the target site. Without wishing to be bound by any particular theory, it is believed that an accessible region is one that is not packaged into a nucleosomal structure. The distinct structure of an accessible region can often be detected by its sensitivity to chemical and enzymatic probes, for example, nucleases.

A "target site" or "target sequence" is a nucleic acid sequence that defines a portion of a nucleic acid to which a binding molecule will bind, provided sufficient conditions for binding exist. For example, the sequence 5'-GAATTC-3' is a target site for the Eco RI restriction endonuclease.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, an *Agrogacterium tumefacians* T-strand, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a ZFP DNA-binding domain and a cleavage domain) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of a mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression.

"Plant" cells include, but are not limited to, cells of monocotyledonous (monocots) or dicotyledonous (dicots) plants. Non-limiting examples of monocots include cereal plants such as maize, rice, barley, oats, wheat, sorghum, rye, sugarcane, pineapple, onion, banana, and coconut. Non-limiting examples of dicots include tobacco, tomato, sunflower, cotton, sugarbeet, potato, lettuce, melon, soybean, canola (rapeseed), and alfalfa. Plant cells may be from any part of the plant and/or from any stage of plant development.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 25,000 nucleotide pairs in length, or any integral value of nucleotide pairs.

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a ZFP DNA-binding domain is fused to a cleavage domain, the ZFP DNA-binding domain and the cleavage domain are in operative linkage if, in the fusion polypeptide, the ZFP DNA-binding domain portion is able to bind its target site and/or its binding site, while the cleavage domain is able to cleave DNA in the vicinity of the target site.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields et al. (1989) *Nature* 340:245-246; U.S. Pat. No. 5,585,245 and PCT WO 98/44350.

Target Sites

The disclosed methods and compositions include fusion proteins comprising a cleavage domain (or a cleavage half-domain) and a zinc finger domain, in which the zinc finger domain, by binding to a sequence in cellular chromatin (e.g., a target site or a binding site), directs the activity of the cleavage domain (or cleavage half-domain) to the vicinity of the sequence and, hence, induces cleavage in the vicinity of the target sequence. As set forth elsewhere in this disclosure, a zinc finger domain can be engineered to bind to virtually any desired sequence. Accordingly, after identifying a region of interest containing a sequence at which cleavage or recombination is desired, one or more zinc finger binding domains can be engineered to bind to one or more sequences in the region of interest. Expression of a fusion protein comprising a zinc finger binding domain and a cleavage domain (or of two fusion proteins, each comprising a zinc finger binding domain and a cleavage half-domain), in a cell, effects cleavage in the region of interest.

Selection of a sequence in cellular chromatin for binding by a zinc finger domain (e.g., a target site) can be accomplished, for example, according to the methods disclosed in co-owned U.S. Pat. No. 6,453,242 (Sep. 17, 2002), which also discloses methods for designing ZFPs to bind to a selected sequence. It will be clear to those skilled in the art that simple visual inspection of a nucleotide sequence can also be used for selection of a target site. Accordingly, any means for target site selection can be used in the claimed methods.

Target sites are generally composed of a plurality of adjacent target subsites. A target subsite refers to the sequence (usually either a nucleotide triplet, or a nucleotide quadruplet that can overlap by one nucleotide with an adjacent quadruplet) bound by an individual zinc finger. See, for example, WO 02/077227. If the strand with which a zinc finger protein makes most contacts is designated the target strand "primary recognition strand," or "primary contact strand," some zinc finger proteins bind to a three base triplet in the target strand and a fourth base on the non-target strand. A target site generally has a length of at least 9 nucleotides and, accordingly, is bound by a zinc finger binding domain comprising at least three zinc fingers. However binding of, for example, a 4-finger binding domain to a 12-nucleotide target site, a 5-finger binding domain to a 15-nucleotide target site or a 6-finger binding domain to an 18-nucleotide target site, is also possible. As will be apparent, binding of larger binding domains (e.g., 7-, 8-, 9-finger and more) to longer target sites is also possible.

It is not necessary for a target site to be a multiple of three nucleotides. For example, in cases in which cross-strand interactions occur (see, e.g., U.S. Pat. No. 6,453,242 and WO 02/077227), one or more of the individual zinc fingers of a multi-finger binding domain can bind to overlapping quadruplet subsites. As a result, a three-finger protein can bind a 10-nucleotide sequence, wherein the tenth nucleotide is part of a quadruplet bound by a terminal finger, a four-finger protein can bind a 13-nucleotide sequence, wherein the thirteenth nucleotide is part of a quadruplet bound by a terminal finger, etc.

The length and nature of amino acid linker sequences between individual zinc fingers in a multi-finger binding domain also affects binding to a target sequence. For example, the presence of a so-called "non-canonical linker," "long linker" or "structured linker" between adjacent zinc fingers in a multi-finger binding domain can allow those fingers to bind subsites which are not immediately adjacent. Non-limiting examples of such linkers are described, for example, in U.S. Pat. No. 6,479,626 and WO 01/53480. Accordingly, one or more subsites, in a target site for a zinc finger binding domain, can be separated from each other by 1, 2, 3, 4, 5 or more nucleotides. To provide but one example, a four-finger binding domain can bind to a 13-nucleotide target site comprising, in sequence, two contiguous 3-nucleotide subsites, an intervening nucleotide, and two contiguous triplet subsites.

Distance between sequences (e.g., target sites) refers to the number of nucleotides or nucleotide pairs intervening between two sequences, as measured from the edges of the sequences nearest each other.

In certain embodiments in which cleavage depends on the binding of two zinc finger domain/cleavage half-domain fusion molecules to separate target sites, the two target sites can be on opposite DNA strands. In other embodiments, both target sites are on the same DNA strand.

Zinc Finger Binding Domains

A zinc finger binding domain comprises one or more zinc fingers. Miller et al. (1985) *EMBO J.* 4:1609-1614; Rhodes (1993) *Scientific American* Feb.:56-65; U.S. Pat. No. 6,453, 242. Typically, a single zinc finger domain is about 30 amino acids in length. Structural studies have demonstrated that each zinc finger domain (motif) contains two beta sheets (held in a beta turn which contains the two invariant cysteine residues) and an alpha helix (containing the two invariant histidine residues), which are held in a particular conformation through coordination of a zinc atom by the two cysteines and the two histidines.

Zinc fingers include both canonical $C_2H_2$ zinc fingers (i.e., those in which the zinc ion is coordinated by two cysteine and two histidine residues) and non-canonical zinc fingers such as, for example, $C_3H$ zinc fingers (those in which the zinc ion is coordinated by three cysteine residues and one histidine residue) and $C_4$ zinc fingers (those in which the zinc ion is coordinated by four cysteine residues). See also WO 02/057293.

Zinc finger binding domains can be engineered to bind to a sequence of choice. See, for example, Beerli et al. (2002) *Nature Biotechnol.* 20:135-141; Pabo et al. (2001) *Ann. Rev. Biochem.* 70:313-340; Isalan et al. (2001) *Nature Biotechnol.* 19:656-660; Segal et al. (2001) *Curr. Opin. Biotechnol.* 12:632-637; Choo et al. (2000) *Curr. Opin. Struct. Biol.* 10:411-416. An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453, 242 and 6,534,261. Additional design methods are disclosed, for example, in U.S. Pat. Nos. 6,746,838; 6,785,613; 6,866,997; and 7,030,215.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237.

Enhancement of binding specificity for zinc finger binding domains has been described, for example, in co-owned U.S. Pat. No. 6,794,136.

Since an individual zinc finger binds to a three-nucleotide (i.e., triplet) sequence (or a four-nucleotide sequence which can overlap, by one nucleotide, with the four-nucleotide binding site of an adjacent zinc finger), the length of a sequence to which a zinc finger binding domain is engineered to bind (e.g., a target sequence) will determine the number of zinc fingers in an engineered zinc finger binding domain. For example, for ZFPs in which the finger motifs do not bind to overlapping subsites, a six-nucleotide target sequence is bound by a two-finger binding domain; a nine-nucleotide target sequence is bound by a three-finger binding domain, etc. As noted herein, binding sites for individual zinc fingers (i.e., subsites) in a target site need not be contiguous, but can be separated by one or several nucleotides, depending on the length and nature of the amino acids sequences between the zinc fingers (i.e., the inter-finger linkers) in a multi-finger binding domain.

In a multi-finger zinc finger binding domain, adjacent zinc fingers can be separated by amino acid linker sequences of approximately 5 amino acids (so-called "canonical" inter-finger linkers) or, alternatively, by one or more non-canonical linkers. See, e.g., co-owned U.S. Pat. Nos. 6,453,242 and 6,534,261. For engineered zinc finger binding domains comprising more than three fingers, insertion of longer ("non-canonical") inter-finger linkers between certain of the zinc fingers may be preferred as it may increase the affinity and/or specificity of binding by the binding domain. See, for example, U.S. Pat. No. 6,479,626 and WO 01/53480. Accordingly, multi-finger zinc finger binding domains can also be characterized with respect to the presence and location of non-canonical inter-finger linkers. For example, a six-finger zinc finger binding domain comprising three fingers (joined by two canonical inter-finger linkers), a long linker and three additional fingers (joined by two canonical inter-finger linkers) is denoted a 2×3 configuration. Similarly, a binding domain comprising two fingers (with a canonical linker therebetween), a long linker and two additional fingers (joined by a canonical linker) is denoted a 2×2 protein. A protein comprising three two-finger units (in each of which the two fingers are joined by a canonical linker), and in which each two-finger unit is joined to the adjacent two finger unit by a long linker, is referred to as a 3×2 protein.

The presence of a long or non-canonical inter-finger linker between two adjacent zinc fingers in a multi-finger binding domain often allows the two fingers to bind to subsites which are not immediately contiguous in the target sequence. Accordingly, there can be gaps of one or more nucleotides between subsites in a target site; i.e., a target site can contain one or more nucleotides that are not contacted by a zinc finger. For example, a 2×2 zinc finger binding domain can bind to two six-nucleotide sequences separated by one nucleotide, i.e., it binds to a 13-nucleotide target site. See also Moore et al. (2001a) Proc. Natl. Acad. Sci. USA 98:1432-1436; Moore et al. (2001b) Proc. Natl. Acad. Sci. USA 98:1437-1441 and WO 01/53480.

As mentioned previously, a target subsite is a three- or four-nucleotide sequence that is bound by a single zinc finger. For certain purposes, a two-finger unit is denoted a binding module. A binding module can be obtained by, for example, selecting for two adjacent fingers in the context of a multi-finger protein (generally three fingers) which bind a particular six-nucleotide target sequence. Alternatively, modules can be constructed by assembly of individual zinc fingers. See also WO 98/53057 and WO 01/53480.

Cleavage Domains

The cleavage domain portion of the fusion proteins disclosed herein can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al., (1997) *Nucleic Acids Res.* 25:3379-3388. Additional enzymes which cleave DNA are known (e.g., S1 Nuclease; mung bean nuclease; pancreatic DNase I; micrococcal nuclease; yeast HO endonuclease; see also Linn et al. (eds.) *Nucleases*, Cold Spring Harbor Laboratory Press, 1993). One or more of these enzymes (or functional fragments thereof) can be used as a source of cleavage domains and cleavage half-domains.

Similarly, a cleavage half-domain (e.g., fusion proteins comprising a zinc finger binding domain and a cleavage half-domain) can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotides or more). In general, the point of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme FokI catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) *Proc. Natl. Acad. Sci. USA* 89:4275-4279; Li et al. (1993) *Proc. Natl. Acad. Sci. USA* 90:2764-2768; Kim et al. (1994a) *Proc. Natl. Acad. Sci. USA* 91:883-887; Kim et al. (1994b) *J. Biol. Chem.* 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is Fok I. This particular enzyme is active as a dimer. Bitinaite et al. (1998) *Proc. Natl. Acad. Sci. USA* 95: 10,570-10,575. Accordingly, for the purposes of the present disclosure, the portion of the Fok I enzyme used in the disclosed fusion proteins is considered a cleavage half-domain. Thus, for targeted double-stranded cleavage and/or targeted replacement of cellular sequences using zinc finger-Fok I fusions, two fusion proteins, each comprising a FokI cleavage half-domain, can be used to reconstitute a catalytically active cleavage domain. Alternatively, a single polypeptide molecule containing a zinc finger binding domain and two Fok I cleavage half-domains can also be used. Parameters for targeted cleavage and targeted sequence alteration using zinc finger-Fok I fusions are provided elsewhere in this disclosure.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are listed in Table 1. Additional restriction enzymes also contain separable binding and cleavage domains, and these are contemplated by the present disclosure. See, for example, Roberts et al. (2003) *Nucleic Acids Res.* 31:418-420.

TABLE 1

Some Type IIS Restriction Enzymes

Aar I
Ace III
Aci I
Alo I
Bae I
Bbr7 I
Bbv I
Bbv II
BbvC I
Bcc I
Bce83 I
BceA I
Bcef I
Bcg I
BciV I
Bfi I
Bin I
Bmg I
Bpu10 I
BsaX I
Bsb I
BscA I
BscG I
BseR I
BseY I
Bsi I
Bsm I
BsmA I
BsmF I
Bsp24 I
BspG I
BspM I
BspNC I
Bsr I
BsrB I
BsrD I
BstF5 I
Btr I
Bts I
Cdi I
CjeP I
Drd II TABLE 1-continued Some Type IIS Restriction Enzymes Eci I
Eco31 I
Eco57 I
Eco57M I
Esp3 I
Fau I
Fin I
Fok I
Gdi II
Gsu I
Hga I
Hin4 II
Hph I
Ksp632 I
Mbo II
Mly I
Mme I
Mnl I
Pfl1108 I
Ple I
Ppi I
Psr I
RleA I
Sap I
SfaN I
Sim I
SspD5 I
Sth132 I
Sts I
TspDT I
TspGW I
Tth111 II
UbaP I
Bsa I
BsmB I Zinc Finger Domain-Cleavage Domain Fusions Methods for design and construction of fusion proteins (and polynucleotides encoding same) are known to those of skill in the art. For example, methods for the design and construction of fusion protein comprising zinc finger proteins (and polynucleotides encoding same) are described in co-owned U.S. Pat. Nos. 6,453,242 and 6,534,261. In certain embodiments, polynucleotides encoding such fusion proteins are constructed. These polynucleotides can be inserted into a vector and the vector can be introduced into a cell (see below for additional disclosure regarding vectors and methods for introducing polynucleotides into cells).

In certain embodiments of the methods described herein, a fusion protein comprises a zinc finger binding domain and a cleavage half-domain from the Fok I restriction enzyme, and two such fusion proteins are expressed in a cell. Expression of two fusion proteins in a cell can result from delivery of the two proteins to the cell; delivery of one protein and one nucleic acid encoding one of the proteins to the cell; delivery of two nucleic acids, each encoding one of the proteins, to the cell; or by delivery of a single nucleic acid, encoding both proteins, to the cell. In additional embodiments, a fusion protein comprises a single polypeptide chain comprising two cleavage half domains and a zinc finger binding domain. In this case, a single fusion protein is expressed in a cell and, without wishing to be bound by theory, is believed to cleave DNA as a result of formation of an intramolecular dimer of the cleavage half-domains.

In certain embodiments, the components of the fusion proteins (e.g., ZPP-Fok I fusions) are arranged such that the zinc finger domain is nearest the amino terminus of the fusion protein, and the cleavage half-domain is nearest the carboxy-terminus. This mirrors the relative orientation of the cleavage domain in naturally-occurring dimerizing cleavage domains such as those derived from the Fok I enzyme, in which the DNA-binding domain is nearest the amino terminus and the cleavage half-domain is nearest the carboxy terminus. In these embodiments, dimerization of the cleavage half-domains to form a functional nuclease is brought about by binding of the fusion proteins to sites on opposite DNA strands, with the 5' ends of the binding sites being proximal to each other.

In additional embodiments, the components of the fusion proteins (e.g., ZFP-Fok I fusions) are arranged such that the cleavage half-domain is nearest the amino terminus of the fusion protein, and the zinc finger domain is nearest the carboxy-terminus. In these embodiments, dimerization of the cleavage half-domains to form a functional nuclease is brought about by binding of the fusion proteins to sites on opposite DNA strands, with the 3' ends of the binding sites being proximal to each other.

In yet additional embodiments, a first fusion protein contains the cleavage half-domain nearest the amino terminus of the fusion protein, and the zinc finger domain nearest the carboxy-terminus, and a second fusion protein is arranged such that the zinc finger domain is nearest the amino terminus of the fusion protein, and the cleavage half-domain is nearest the carboxy-terminus. In these embodiments, both fusion proteins bind to the same DNA strand, with the binding site of the first fusion protein containing the zinc finger domain nearest the carboxy terminus located to the 5' side of the binding site of the second fusion protein containing the zinc finger domain nearest the amino terminus.

In certain embodiments, the disclosed fusion proteins the amino acid sequence between the zinc finger domain and the cleavage domain (or cleavage half-domain) is denoted the "ZC linker." The ZC linker is to be distinguished from the inter-finger linkers discussed above. See, e.g., U.S. Patent Publications 20050064474A1 and 20030232410, and International Patent Publication WO05/084190, for details on obtaining ZC linkers that optimize cleavage.

Methods for Targeted Cleavage

The disclosed methods and compositions can be used to cleave DNA at a region of interest in cellular chromatin (e.g., at a desired or predetermined site in a genome, for example, in a gene, either mutant or wild-type). For such targeted DNA cleavage, a zinc finger binding domain is engineered to bind a target site at or near the predetermined cleavage site, and a fusion protein comprising the engineered zinc finger binding domain and a cleavage domain is expressed in a cell. Upon binding of the zinc finger portion of the fusion protein to the target site, the DNA is cleaved near the target site by the cleavage domain. The exact site of cleavage can depend on the length of the ZC linker.

Alternatively, two fusion proteins, each comprising a zinc finger binding domain and a cleavage half-domain, are expressed in a cell, and bind to target sites which are juxtaposed in such a way that a functional cleavage domain is reconstituted and DNA is cleaved in the vicinity of the target sites. In one embodiment, cleavage occurs between the target sites of the two zinc finger binding domains. One or both of the zinc finger binding domains can be engineered.

For targeted cleavage using a zinc finger binding domain-cleavage domain fusion polypeptide, the binding site can encompass the cleavage site, or the near edge of the binding site can be 1, 2, 3, 4, 5, 6, 10, 25, 50 or more nucleotides (or any integral value between 1 and 50 nucleotides) from the cleavage site. The exact location of the binding site, with respect to the cleavage site, will depend upon the particular cleavage domain, and the length of the ZC linker. For methods in which two fusion polypeptides, each comprising a zinc finger binding domain and a cleavage half-domain, are used, the binding sites generally straddle the cleavage site. Thus the near edge of the first binding site can be 1, 2, 3, 4, 5, 6, 10, 25 or more nucleotides (or any integral value between 1 and 50 nucleotides) on one side of the cleavage site, and the near edge of the second binding site can be 1, 2, 3, 4, 5, 6, 10, 25 or more nucleotides (or any integral value between 1 and 50 nucleotides) on the other side of the cleavage site. Methods for mapping cleavage sites in vitro and in vivo are known to those of skill in the art.

Thus, the methods described herein can employ an engineered zinc finger binding domain fused to a cleavage domain. In these cases, the binding domain is engineered to bind to a target sequence, at or near which cleavage is desired. The fusion protein, or a polynucleotide encoding same, is introduced into a plant cell. Once introduced into, or expressed in, the cell, the fusion protein binds to the target sequence and cleaves at or near the target sequence. The exact site of cleavage depends on the nature of the cleavage domain and/or the presence and/or nature of linker sequences between the binding and cleavage domains. In cases where two fusion proteins, each comprising a cleavage half-domain, are used, the distance between the near edges of the binding sites can be 1, 2, 3, 4, 5, 6, 7, 8, 9, 10, 25 or more nucleotides (or any integral value between 1 and 50 nucleotides). Optimal levels of cleavage can also depend on both the distance between the binding sites of the two fusion proteins (see, for example, Smith et al. (2000) *Nucleic Acids Res.* 28:3361-3369; Bibikova et al. (2001) *Mol. Cell. Biol.* 21:289-297) and the length of the ZC linker in each fusion protein. See, also, U.S. Patent Publication 20050064474A1 and International Patent Publications WO05/084190, WO05/014791 and WO03/080809.

In certain embodiments, the cleavage domain comprises two cleavage half-domains, both of which are part of a single polypeptide comprising a binding domain, a first cleavage half-domain and a second cleavage half-domain. The cleavage half-domains can have the same amino acid sequence or different amino acid sequences, so long as they function to cleave the DNA.

Cleavage half-domains may also be provided in separate molecules. For example, two fusion polypeptides may be introduced into a cell, wherein each polypeptide comprises a binding domain and a cleavage half-domain. The cleavage half-domains can have the same amino acid sequence or different amino acid sequences, so long as they function to cleave the DNA. Further, the binding domains bind to target sequences which are typically disposed in such a way that, upon binding of the fusion polypeptides, the two cleavage half-domains are presented in a spatial orientation to each other that allows reconstitution of a cleavage domain (e.g., by dimerization of the half-domains), thereby positioning the half-domains relative to each other to form a functional cleavage domain, resulting in cleavage of cellular chromatin in a region of interest. Generally, cleavage by the reconstituted cleavage domain occurs at a site located between the two target sequences. One or both of the proteins can be engineered to bind to its target site.

The two fusion proteins can bind in the region of interest in the same or opposite polarity, and their binding sites (i.e., target sites) can be separated by any number of nucleotides, e.g., from 0 to 200 nucleotides or any integral value therebetween. In certain embodiments, the binding sites for two fusion proteins, each comprising a zinc finger binding domain and a cleavage half-domain, can be located between 5 and 18 nucleotides apart, for example, 5-8 nucleotides apart, or 15-18 nucleotides apart, or 6 nucleotides apart, or 16 nucleotides apart, as measured from the edge of each binding site nearest the other binding site, and cleavage occurs between the binding sites.

The site at which the DNA is cleaved generally lies between the binding sites for the two fusion proteins. Double-strand breakage of DNA often results from two single-strand breaks, or "nicks," offset by 1, 2, 3, 4, 5, 6 or more nucleotides, (for example, cleavage of double-stranded DNA by native Fok I results from single-strand breaks offset by 4 nucleotides). Thus, cleavage does not necessarily occur at exactly opposite sites on each DNA strand. In addition, the structure of the fusion proteins and the distance between the target sites can influence whether cleavage occurs adjacent a single nucleotide pair, or whether cleavage occurs at several sites. However, for many applications, including targeted recombination and targeted mutagenesis (see infra) cleavage within a range of nucleotides is generally sufficient, and cleavage between particular base pairs is not required.

As noted above, the fusion protein(s) can be introduced as polypeptides and/or polynucleotides. For example, two polynucleotides, each comprising sequences encoding one of the aforementioned polypeptides, can be introduced into a cell, and when the polypeptides are expressed and each binds to its target sequence, cleavage occurs at or near the target sequence. Alternatively, a single polynucleotide comprising sequences encoding both fusion polypeptides is introduced into a cell. Polynucleotides can be DNA, RNA or any modified forms or analogues or DNA and/or RNA.

To enhance cleavage specificity, additional compositions may also be employed in the methods described herein. For example, single cleavage half-domains can exhibit limited double-stranded cleavage activity. In methods in which two fusion proteins, each containing a three-finger zinc finger domain and a cleavage half-domain, are introduced into the cell, either protein specifies an approximately 9-nucleotide target site. Although the aggregate target sequence of 18 nucleotides is likely to be unique in a mammalian genome, any given 9-nucleotide target site occurs, on average, approximately 23,000 times in the human genome. Thus, non-specific cleavage, due to the site-specific binding of a single half-domain, may occur. Accordingly, the methods described herein contemplate the use of a dominant-negative mutant of a cleavage half-domain such as Fok I (or a nucleic acid encoding same) that is expressed in a cell along with the two fusion proteins. The dominant-negative mutant is capable of dimerizing but is unable to cleave, and also blocks the cleavage activity of a half-domain to which it is dimerized. By providing the dominant-negative mutant in molar excess to the fusion proteins, only regions in which both fusion proteins are bound will have a high enough local concentration of functional cleavage half-domains for dimerization and cleavage to occur. At sites where only one of the two fusion proteins is bound, its cleavage half-domain forms a dimer with the dominant negative mutant half-domain, and undesirable, non-specific cleavage does not occur.

Three catalytic amino acid residues in the Fok I cleavage half-domain have been identified: Asp 450, Asp 467 and Lys 469. Bitinaite et al. (1998) *Proc. Natl. Acad. Sci. USA* 95: 10,570-10,575. Thus, one or more mutations at one of these residues can be used to generate a dominant negative mutation. Further, many of the catalytic amino acid residues of other Type IIS endonucleases are known and/or can be determined, for example, by alignment with Fok I sequences and/or by generation and testing of mutants for catalytic activity.

Dimerization Domain Mutations in the Cleavage Half-Domain

Methods for targeted cleavage which involve the use of fusions between a ZFP and a cleavage half-domain (such as, e.g., a ZFP/FokI fusion) require the use of two such fusion molecules, each generally directed to a distinct target sequence. Target sequences for the two fusion proteins can be chosen so that targeted cleavage is directed to a unique site in a genome, as discussed above. A potential source of reduced cleavage specificity could result from homodimerization of one of the two ZFP/cleavage half-domain fusions. This might occur, for example, due to the presence, in a genome, of inverted repeats of the target sequences for one of the two ZFP/cleavage half-domain fusions, located so as to allow two copies of the same fusion protein to bind with an orientation and spacing that allows formation of a functional dimer.

One approach for reducing the probability of this type of aberrant cleavage at sequences other than the intended target site involves generating variants of the cleavage half-domain that minimize or prevent homodimerization. Preferably, one or more amino acids in the region of the half-domain involved in its dimerization are altered. In the crystal structure of the FokI protein dimer, the structure of the cleavage half-domains is reported to be similar to the arrangement of the cleavage half-domains during cleavage of DNA by FokI. Wah et al. (1998) *Proc. Natl. Acad. Sci. USA* 95:10564-10569. This structure indicates that amino acid residues at positions 483 and 487 play a key role in the dimerization of the FokI cleavage half-domains. The structure also indicates that amino acid residues at positions 446, 447, 479, 483, 484, 486, 487, 490, 491, 496, 498, 499, 500, 531, 534, 537, and 538 are all close enough to the dimerization interface to influence dimerization. Accordingly, amino acid sequence alterations at one or more of the aforementioned positions will likely alter the dimerization properties of the cleavage half-domain. Such changes can be introduced, for example, by constructing a library containing (or encoding) different amino acid residues at these positions and selecting variants with the desired properties, or by rationally designing individual mutants. In addition to preventing homodimerization, it is also possible that some of these mutations may increase the cleavage efficiency above that obtained with two wild-type cleavage half-domains.

Accordingly, alteration of a FokI cleavage half-domain at any amino acid residue which affects dimerization can be used to prevent one of a pair of ZFP/FokI fusions from undergoing homodimerization which can lead to cleavage at undesired sequences. Thus, for targeted cleavage using a pair of ZFP/FokI fusions, one or both of the fusion proteins can comprise one or more amino acid alterations that inhibit self-dimerization, but allow heterodimerization of the two fusion proteins to occur such that cleavage occurs at the desired target site. In certain embodiments, alterations are present in both fusion proteins, and the alterations have additive effects; i.e., homodimerization of either fusion, leading to aberrant cleavage, is minimized or abolished, while heterodimerization of the two fusion proteins is facilitated compared to that obtained with wild-type cleavage half-domains.

Methods for Targeted Alteration of Genomic Sequences and Targeted Recombination

Also described herein are methods of replacing a genomic sequence (e.g., a region of interest in cellular chromatin)

with a homologous non-identical sequence (i.e., targeted recombination). Previous attempts to replace particular sequences have involved contacting a cell with a polynucleotide comprising sequences bearing homology to a chromosomal region (i.e., a donor DNA), followed by selection of cells in which the donor DNA molecule had undergone homologous recombination into the genome. The success rate of these methods is low, due to poor efficiency of homologous recombination and a high frequency of non-specific insertion of the donor DNA into regions of the genome other than the target site.

The present disclosure provides methods of targeted sequence alteration characterized by a greater efficiency of targeted recombination and a lower frequency of non-specific insertion events. The methods involve making and using engineered zinc finger binding domains fused to cleavage domains (or cleavage half-domains) to make one or more targeted double-stranded breaks in cellular DNA. Because double-stranded breaks in cellular DNA stimulate cellular repair mechanisms several thousand-fold in the vicinity of the cleavage site, such targeted cleavage allows for the alteration or replacement (via homology-directed repair) of sequences at virtually any site in the genome.

In addition to the fusion molecules described herein, targeted replacement of a selected genomic sequence also requires the introduction of the replacement (or donor) sequence. The donor sequence can be introduced into the cell prior to, concurrently with, or subsequent to, expression of the fusion protein(s). The donor polynucleotide contains sufficient homology to a genomic sequence to support homologous recombination (or homology-directed repair) between it and the genomic sequence to which it bears homology. Approximately 25, 50 100, 200, 500, 750, 1,000, 1,500, 2,000 nucleotides or more of sequence homology between a donor and a genomic sequence (or any integral value between 10 and 2,000 nucleotides, or more) will support homologous recombination therebetween. Donor sequences can range in length from 10 to 5,000 nucleotides (or any integral value of nucleotides therebetween) or longer. It will be readily apparent that the donor sequence is typically not identical to the genomic sequence that it replaces. For example, the sequence of the donor polynucleotide can contain one or more single base changes, insertions, deletions, inversions or rearrangements with respect to the genomic sequence, so long as sufficient homology with chromosomal sequences is present. Alternatively, a donor sequence can contain a non-homologous sequence flanked by two regions of homology. Additionally, donor sequences can comprise a vector molecule containing sequences that are not homologous to the region of interest in cellular chromatin. Generally, the homologous region(s) of a donor sequence will have at least 50% sequence identity to a genomic sequence with which recombination is desired. In certain embodiments, 60%, 70%, 80%, 90%, 95%, 98%, 99%, or 99.9% sequence identity is present. Any value between 1% and 100% sequence identity can be present, depending upon the length of the donor polynucleotide.

A donor molecule can contain several, discontinuous regions of homology to cellular chromatin. For example, for targeted insertion of sequences not normally present in a region of interest, said sequences can be present in a donor nucleic acid molecule and flanked by regions of homology to sequence in the region of interest.

To simplify assays (e.g., hybridization, PCR, restriction enzyme digestion) for determining successful insertion of the donor sequence, certain sequence differences may be present in the donor sequence as compared to the genomic sequence. Preferably, if located in a coding region, such nucleotide sequence differences will not change the amino acid sequence, or will make silent amino acid changes (i.e., changes which do not affect the structure or function of the protein). The donor polynucleotide can optionally contain changes in sequences corresponding to the zinc finger domain binding sites in the region of interest, to prevent cleavage of donor sequences that have been introduced into cellular chromatin by homologous recombination.

The donor polynucleotide can be DNA or RNA, single-stranded or double-stranded and can be introduced into a cell in linear or circular form. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al. (1987) *Proc. Natl. Acad. Sci. USA* 84:4959-4963; Nehls et al. (1996) *Science* 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

A polynucleotide can be introduced into a cell as part of a vector molecule having additional sequences such as, for example, replication origins, promoters and genes encoding antibiotic resistance. Moreover, donor polynucleotides can be introduced as naked nucleic acid, as nucleic acid complexed with an agent such as a liposome or poloxamer, or can be delivered by bacteria or viruses (e.g., *Agrobacterium, Rhizobium* sp. NGR234, *Sinorhizoboium meliloti, Mesorhizobium loti,* tobacco mosaic virus, potato virus X, cauliflower mosaic virus and cassava vein mosaic virus. See, e.g., Chung et al. (2006) *Trends Plant Sci.* 11(1):1-4.

Without being bound by one theory, it appears that the presence of a double-stranded break in a cellular sequence, coupled with the presence of an exogenous DNA molecule having homology to a region adjacent to or surrounding the break, activates cellular mechanisms which repair the break by transfer of sequence information from the donor molecule into the cellular (e.g., genomic or chromosomal) sequence; i.e., by a processes of homology-directed repair, also known as "gene conversion." Applicants' methods advantageously combine the powerful targeting capabilities of engineered ZFPs with a cleavage domain (or cleavage half-domain) to specifically target a double-stranded break to the region of the genome at insertion of exogenous sequences is desired.

For alteration of a chromosomal sequence, it is not necessary for the entire sequence of the donor to be copied into the chromosome, as long as enough of the donor sequence is copied to effect the desired sequence alteration.

The efficiency of insertion of donor sequences by homologous recombination is inversely related to the distance, in the cellular DNA, between the double-stranded break and the site at which recombination is desired. In other words, higher homologous recombination efficiencies are observed when the double-stranded break is closer to the site at which recombination is desired. In cases in which a precise site of recombination is not predetermined (e.g., the desired recombination event can occur over an interval of genomic sequence), the length and sequence of the donor nucleic acid, together with the site(s) of cleavage, are selected to obtain the desired recombination event. In cases in which the desired event is designed to change the sequence of a single nucleotide pair in a genomic sequence, cellular chromatin is cleaved within 10,000 nucleotides on either side of that nucleotide pair. In certain embodiments, cleavage occurs within 1,000, 500, 200, 100, 90, 80, 70, 60, 50, 40, 30, 20, 10, 5, or 2 nucleotides, or any integral value between 2 and 1,000 nucleotides, on either side of the nucleotide pair whose sequence is to be changed.

As detailed above, the binding sites for two fusion proteins, each comprising a zinc finger binding domain and a cleavage half-domain, can be located 5-8 or 15-18 nucleotides apart, as measured from the edge of each binding site nearest the other binding site, and cleavage occurs between the binding sites. Whether cleavage occurs at a single site or at multiple sites between the binding sites is immaterial, since the cleaved genomic sequences are replaced by the donor sequences. Thus, for efficient alteration of the sequence of a single nucleotide pair by targeted recombination, the midpoint of the region between the binding sites is within 10,000 nucleotides of that nucleotide pair, preferably within 1,000 nucleotides, or 500 nucleotides, or 200 nucleotides, or 100 nucleotides, or 50 nucleotides, or 20 nucleotides, or 10 nucleotides, or 5 nucleotide, or 2 nucleotides, or one nucleotide, or at the nucleotide pair of interest.

In certain embodiments, a homologous chromosome can serve as the donor polynucleotide. Thus, for example, correction of a mutation in a heterozygote can be achieved by engineering fusion proteins which bind to and cleave the mutant sequence on one chromosome, but do not cleave the wild-type sequence on the homologous chromosome. The double-stranded break on the mutation-bearing chromosome stimulates a homology-based "gene conversion" process in which the wild-type sequence from the homologous chromosome is copied into the cleaved chromosome, thus restoring two copies of the wild-type sequence.

Methods and compositions are also provided that may enhance levels of targeted recombination including, but not limited to, the use of additional LFP-functional domain fusions to activate expression of genes involved in homologous recombination, such as, for example, members of the RAD52 epistasis group (e.g., Rad50, Rad51, Rad51B, Rad51C, Rad51D, Rad52, Rad54, Rad54B, Mre11, XRCC2, XRCC3), genes whose products interact with the aforementioned gene products (e.g., BRCA1, BRCA2) and/or genes in the NBS1 complex. See, e.g., Boyko et al. (2006) Plant Physiology 141:488-497 and LaFarge et al. (2003) Nucleic Acids Res 31(4): 1148-1155. Similarly ZFP-functional domain fusions can be used, in combination with the methods and compositions disclosed herein, to repress expression of genes involved in non-homologous end joining (e.g., Ku70/80, XRCC4, poly(ADP ribose) polymerase, DNA ligase 4). See, for example, Riha et al. (2002) EMBO 21:2819-2826; Freisner et al. (2003) Plant J. 34:427-440; Chen et al. (1994) European Journal of Biochemistry 224: 135-142. Methods for activation and repression of gene expression using fusions between a zinc finger binding domain and a functional domain are disclosed, for example, in co-owned U.S. Pat. Nos. 6,534,261; 6,824,978 and 6,933,113. Additional repression methods include the use of antisense oligonucleotides and/or small interfering RNA (siRNA or RNAi) targeted to the sequence of the gene to be repressed.

As an alternative to or, in addition to, activating expression of gene products involved in homologous recombination, fusions of these protein (or functional fragments thereof) with a zinc finger binding domain targeted to the region of interest, can be used to recruit these proteins (recombination proteins) to the region of interest, thereby increasing their local concentration and further stimulating homologous recombination processes. Alternatively, a polypeptide involved in homologous recombination as described above (or a functional fragment thereof) can be part of a triple fusion protein comprising a zinc finger binding domain, a cleavage domain (or cleavage half-domain) and the recombination protein (or functional fragment thereof). Additional proteins involved in gene conversion and recombination-related chromatin remodeling, which can be used in the aforementioned methods and compositions, include histone acetyltransferases (e.g., Esa1p, Tip60), histone methyltransferases (e.g., Dot1p), histone kinases and histone phosphatases. See, also, Bhat et al. (1999) Plant J. 33:455-469

Further increases in efficiency of targeted recombination, in cells comprising a zinc finger/nuclease fusion molecule and a donor DNA molecule, are achieved by blocking the cells in the $G_2$ phase of the cell cycle, when homology-driven repair processes are maximally active. Such arrest can be achieved in a number of ways. For example, cells can be treated with e.g., drugs, compounds and/or small molecules which influence cell-cycle progression so as to arrest cells in $G_2$ phase. Exemplary molecules of this type include, but are not limited to, compounds which affect microtubule polymerization (e.g., vinblastine, nocodazole, Taxol), compounds that interact with DNA (e.g., cis-platinum(II) diamine dichloride, Cisplatin, doxorubicin) and/or compounds that affect DNA synthesis (e.g., thymidine, hydroxyurea, L-mimosine, etoposide, 5-fluorouracil). Additional increases in recombination efficiency are achieved by the use of histone deacetylase (HDAC) inhibitors (e.g., sodium butyrate, trichostatin A) which alter chromatin structure to make genomic DNA more accessible to the cellular recombination machinery.

Additional methods for cell-cycle arrest include overexpression of proteins which inhibit the activity of the CDK cell-cycle kinases, for example, by introducing a cDNA encoding the protein into the cell or by introducing into the cell an engineered ZIP which activates expression of the gene encoding the protein. Cell-cycle arrest is also achieved by inhibiting the activity of cyclins and CDKs, for example, using RNAi methods (e.g., U.S. Pat. No. 6,506,559) or by introducing into the cell an engineered ZFP which represses expression of one or more genes involved in cell-cycle progression such as, for example, cyclin and/or CDK genes. See, e.g., co-owned U.S. Pat. No. 6,534,261 for methods for the synthesis of engineered zinc finger proteins for regulation of gene expression.

Alternatively, in certain cases, targeted cleavage is conducted in the absence of a donor polynucleotide (preferably in S or $G_2$ phase), and recombination occurs between homologous chromosomes.

Expression Vectors

A nucleic acid encoding one or more ZFPs or LEP fusion proteins can be cloned into a vector for transformation into prokaryotic or eukaryotic cells for replication and/or expression. Vectors can be prokaryotic vectors, e.g., plasmids, or shuttle vectors, insect vectors, or eukaryotic vectors. A nucleic acid encoding a ZFP can also be cloned into an expression vector, for administration to a plant cell.

To express the ZFPs or ZFP fusion proteins, sequences encoding the ZFPs or ZFP fusions are typically subcloned into an expression vector that contains a promoter to direct transcription. Suitable bacterial and eukaryotic promoters are well known in the art and described, e.g., in Sambrook et al., Molecular Cloning, A Laboratory Manual (2nd ed. 1989; 3$^{rd}$ ed., 2001); Kriegler, Gene Transfer and Expression: *A Laboratory Manual* (1990); and *Current Protocols in Molecular Biology* (Ausubel et al., supra. Bacterial expression systems for expressing the ZFP are available in, e.g., *E. coli*, *Bacillus* sp., and *Salmonella* (Palva et al., *Gene* 22:229-235 (1983)). Kits for such expression systems are commercially available. Eukaryotic expression systems for mammalian cells, yeast, and insect cells are well known by those of skill in the art and are also commercially available.

The promoter used to direct expression of a ZFP-encoding nucleic acid depends on the particular application. For example, a strong constitutive promoter suited to the host cell is typically used for expression and purification of ZFPs.

In contrast, when a ZFP is administered in vivo for plant gene regulation (see, "Nucleic Acid Delivery to Plant Cells" section below), either a constitutive or an inducible promoter is used, depending on the particular use of the ZFP. Non-limiting examples of plant promoters include promoter sequences derived from *A. thaliana* ubiquitin-3 (ubi-3) (Callis, et al., 1990, *J. Biol. Chem.* 265-12486-12493); *A. tumifaciens* mannopine synthase (Δmas) (Petolino et al., U.S. Pat. No. 6,730,824); and/or Cassava Vein Mosaic Virus (CsVMV) (Verdaguer et al., 1996, *Plant Molecular Biology* 31:1129-1139). See, also, Examples.

In addition to the promoter, the expression vector typically contains a transcription unit or expression cassette that contains all the additional elements required for the expression of the nucleic acid in host cells, either prokaryotic or eukaryotic. A typical expression cassette thus contains a promoter operably linked, e.g., to a nucleic acid sequence encoding the ZFP, and signals required, e.g., for efficient polyadenylation of the transcript, transcriptional termination, ribosome binding sites, or translation termination. Additional elements of the cassette may include, e.g., enhancers, and heterologous splicing signals.

The particular expression vector used to transport the genetic information into the cell is selected with regard to the intended use of the ZFP, e.g., expression in plants, animals, bacteria, fungus, protozoa, etc. (see expression vectors described below). Standard bacterial and animal expression vectors are known in the art and are described in detail, for example, U.S. Patent Publication 20050064474A1 and International Patent Publications WO05/084190, WO05/014769 and WO03/080809.

Standard transfection methods can be used to produce bacterial, mammalian, yeast or insect cell lines that express large quantities of protein, which can then be purified using standard techniques (see, e.g., Colley et al., *J. Biol. Chem.* 264:17619-17622 (1989); *Guide to Protein Purification*, in *Methods in Enzymology*, vol. 182 (Deutscher, ed., 1990)). Transformation of eukaryotic and prokaryotic cells are performed according to standard techniques (see, e.g., Morrison, *J. Bact.* 132:349-351 (1977); Clark-Curtiss & Curtiss, *Methods in Enzymology* 101:347-362 (Wu et al., eds., 1983).

Any of the well known procedures for introducing foreign nucleotide sequences into such host cells may be used. These include the use of calcium phosphate transfection, polybrene, protoplast fusion, electroporation, ultrasonic methods (e.g., sonoporation), liposomes, microinjection, naked DNA, plasmid vectors, viral vectors, both episomal and integrative, and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing the protein of choice.

Nucleic Acid Delivery to Plant Cells

As noted above, DNA constructs may be introduced into (e.g., into the genome of) a desired plant host by a variety of conventional techniques. For reviews of such techniques see, for example, Weissbach & Weissbach *Methods for Plant Molecular Biology* (1988, Academic Press, N.Y.) Section VIII, pp. 421-463; and Grierson & Corey, *Plant Molecular Biology* (1988, 2d Ed.), Blackie, London, Ch. 7-9.

For example, the DNA construct may be introduced directly into the genomic DNA of the plant cell using techniques such as electroporation and microinjection of plant cell protoplasts, or the DNA constructs can be introduced directly to plant tissue using biolistic methods, such as DNA particle bombardment (see, e.g., Klein et al (1987) *Nature* 327:70-73). Alternatively, the DNA constructs may be combined with suitable T-DNA flanking regions and introduced into a conventional *Agrobacterium tumefaciens* host vector. *Agrobacterium tumefaciens*-mediated transformation techniques, including disarming and use of binary vectors, are well described in the scientific literature. See, for example Horsch et al (1984) *Science* 233:496-498, and Fraley et al (1983) *Proc. Nat'l. Acad. Sci. USA* 80:4803.

In addition, gene transfer may be achieved using non-Agrobacterium bacteria or viruses such as *Rhizobium* sp. NGR234, *Sinorhizoboium meliloti*, *Mesorhizobium loti*, potato virus X, cauliflower mosaic virus and cassava vein mosaic virus and/or tobacco mosaic virus, See, e.g., Chung et al. (2006) *Trends Plant Sci.* 11(1):1-4.

The virulence functions of the *Agrobacterium tumefaciens* host will direct the insertion of the construct and adjacent marker into the plant cell DNA when the cell is infected by the bacteria using binary T DNA vector (Bevan (1984) *Nuc. Acid Res.* 12:8711-8721) or the co-cultivation procedure (Horsch et al (1985) *Science* 227:1229-1231). Generally, the *Agrobacterium* transformation system is used to engineer dicotyledonous plants (Bevan et al (1982) *Ann. Rev. Genet.* 16:357-384; Rogers et al (1986) *Methods Enzymol.* 118:627-641). The *Agrobacterium* transformation system may also be used to transform, as well as transfer, DNA to monocotyledonous plants and plant cells. See U.S. Pat. No. 5,591,616; Hemalsteen et al (1984) *EMBO J* 3:3039-3041; Hooykass-Van Slogteren et al (1984) *Nature* 311:763-764; Grimsley et al (1987) *Nature* 325:1677-179; Boulton et al (1989) *Plant Mol. Biol.* 12:31-40; and Gould et al (1991) *Plant Physiol.* 95:426-434.

Alternative gene transfer and transformation methods include, but are not limited to, protoplast transformation through calcium-, polyethylene glycol (PEG)- or electroporation-mediated uptake of naked DNA (see Paszkowski et al. (1984) *EMBO J* 3:2717-2722, Potrykus et al. (1985) *Molec. Gen. Genet.* 199:169-177; Fromm et al. (1985) *Proc. Nat. Acad. Sci. USA* 82:5824-5828; and Shimamoto (1989) *Nature* 338:274-276) and electroporation of plant tissues (D'Halluin et al. (1992) *Plant Cell* 4:1495-1505). Additional methods for plant cell transformation include microinjection, silicon carbide mediated DNA uptake (Kaeppler et al. (1990) *Plant Cell Reporter* 9:415-418), and microprojectile bombardment (see Klein et al. (1988) *Proc. Nat. Acad. Sci. USA* 85:4305-4309; and Gordon-Kamm et al. (1990) *Plant Cell* 2:603-618).

The disclosed methods and compositions can be used to insert exogenous sequences into a predetermined location in a plant cell genome. This is useful inasmuch as expression of an introduced transgene into a plant genome depends critically on its integration site. Accordingly, genes encoding, e.g., nutrients, antibiotics or therapeutic molecules can be inserted, by targeted recombination, into regions of a plant genome favorable to their expression.

Transformed plant cells which are produced by any of the above transformation techniques can be cultured to regenerate a whole plant which possesses the transformed genotype and thus the desired phenotype. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans, et al., "Protoplasts Isolation and Culture" in *Handbook of Plant Cell Culture*, pp. 124-176, Macmillian Publishing Company, New York, 1983; and Binding, *Regeneration of Plants, Plant Protoplasts*, pp. 21-73, CRC Press, Boca Raton, 1985. Regeneration can also be obtained from plant callus, explants, organs, pollens, embryos or parts thereof. Such regeneration techniques are described generally in Klee et al (1987) *Ann. Rev. of Plant Phys.* 38:467-486.

Nucleic acids introduced into a plant cell can be used to confer desired traits on essentially any plant. A wide variety of plants and plant cell systems may be engineered for the desired physiological and agronomic characteristics described herein using the nucleic acid constructs of the present disclosure and the various transformation methods mentioned above. In preferred embodiments, target plants and plant cells for engineering include, but are not limited to, those monocotyledonous and dicotyledonous plants, such as crops including grain crops (e.g., wheat, maize, rice, millet, barley), fruit crops (e.g., tomato, apple, pear, strawberry, orange), forage crops (e.g., alfalfa), root vegetable crops (e.g., carrot, potato, sugar beets, yam), leafy vegetable crops (e.g., lettuce, spinach); flowering plants (e.g., petunia, rose, chrysanthemum), conifers and pine trees (e.g., pine fir, spruce); plants used in phytoremediation (e.g., heavy metal accumulating plants); oil crops (e.g., sunflower, rape seed) and plants used for experimental purposes (e.g., *Arabidopsis*). Thus, the disclosed methods and compositions have use over a broad range of plants, including, but not limited to, species from the genera *Asparagus, Avena, Brassica, Citrus, Citrullus, Capsicum, Cucurbita, Daucus, Glycine, Gossypium, Hordeum, Lactuca, Lycopersicon, Malus, Manihot, Nicotiana, Oryza, Persea, Pisum, Pyrus, Prunus, Raphanus, Secale, Solanuni, Sorghum, Triticum, Vitis, Vigna*, and *Zea*.

One of skill in the art will recognize that after the expression cassette is stably incorporated in transgenic plants and confirmed to be operable, it can be introduced into other plants by sexual crossing. Any of a number of standard breeding techniques can be used, depending upon the species to be crossed.

A transformed plant cell, callus, tissue or plant may be identified and isolated by selecting or screening the engineered plant material for traits encoded by the marker genes present on the transforming DNA. For instance, selection may be performed by growing the engineered plant material on media containing an inhibitory amount of the antibiotic or herbicide to which the transforming gene construct confers resistance. Further, transformed plants and plant cells may also be identified by screening for the activities of any visible marker genes (e.g., the β-glucuronidase, luciferase, B or C1 genes) that may be present on the recombinant nucleic acid constructs. Such selection and screening methodologies are well known to those skilled in the art.

Physical and biochemical methods also may be used to identify plant or plant cell transformants containing inserted gene constructs. These methods include but are not limited to: 1) Southern analysis or PCR amplification for detecting and determining the structure of the recombinant DNA insert; 2) Northern blot, S1 RNase protection, primer-extension or reverse transcriptase-PCR amplification for detecting and examining RNA transcripts of the gene constructs; 3) enzymatic assays for detecting enzyme or ribozyme activity, where such gene products are encoded by the gene construct; 4) protein gel electrophoresis, Western blot techniques, immunoprecipitation, or enzyme-linked immunoassays, where the gene construct products are proteins. Additional techniques, such as in situ hybridization, enzyme staining, and immunostaining, also may be used to detect the presence or expression of the recombinant construct in specific plant organs and tissues. The methods for doing all these assays are well known to those skilled in the art.

Effects of gene manipulation using the methods disclosed herein can be observed by, for example, northern blots of the RNA (e.g., mRNA) isolated from the tissues of interest. Typically, if the amount of mRNA has increased, it can be assumed that the corresponding endogenous gene is being expressed at a greater rate than before. Other methods of measuring gene and/or CYP74B activity can be used. Different types of enzymatic assays can be used, depending on the substrate used and the method of detecting the increase or decrease of a reaction product or by-product. In addition, the levels of and/or CYP74B protein expressed can be measured immunochemically, i.e., ELISA, RIA, EIA and other antibody based assays well known to those of skill in the art, such as by electrophoretic detection assays (either with staining or western blotting). The transgene may be selectively expressed in some tissues of the plant or at some developmental stages, or the transgene may be expressed in substantially all plant tissues, substantially along its entire life cycle. However, any combinatorial expression mode is also applicable.

The present disclosure also encompasses seeds of the transgenic plants described above wherein the seed has the transgene or gene construct. The present disclosure further encompasses the progeny, clones, cell lines or cells of the transgenic plants described above wherein said progeny, clone, cell line or cell has the transgene or gene construct.

ZFPs and expression vectors encoding ZFPs can be administered directly to the plant for targeted cleavage and/or recombination.

Administration of effective amounts is by any of the routes normally used for introducing ZFP into ultimate contact with the plant cell to be treated. The ZFPs are administered in any suitable manner, preferably with pharmaceutically acceptable carriers. Suitable methods of administering such modulators are available and well known to those of skill in the art, and, although more than one route can be used to administer a particular composition, a particular route can often provide a more immediate and more effective reaction than another route.

Carriers may also be used and are determined in part by the particular composition being administered, as well as by the particular method used to administer the composition. Accordingly, there is a wide variety of suitable formulations of pharmaceutical compositions that are available (see, e.g., *Remington's Pharmaceutical Sciences*, 17$^{th}$ ed. 1985)).

Applications

The disclosed methods and compositions for targeted cleavage can be used to induce mutations in a genomic sequence. Targeted cleavage can also be used to create gene knock-outs (e.g., for functional genomics or target validation) and to facilitate targeted insertion of a sequence into a genome (i.e., gene knock-in). Insertion can be by means of replacements of chromosomal sequences through homologous recombination or by targeted integration, in which a new sequence (i.e., a sequence not present in the region of interest), flanked by sequences homologous to the region of interest in the chromosome, is inserted at a predetermined target site. The same methods can also be used to replace a wild-type sequence with a mutant sequence, or to convert one allele to a different allele.

Targeted cleavage of infecting or integrated plant pathogens can be used to treat pathogenic infections in a plant host, for example, by cleaving the genome of the pathogen such that it's pathogenicity is reduced or eliminated. Additionally, targeted cleavage of genes encoding receptors for plant viruses can be used to block expression of such receptors, thereby preventing viral infection and/or viral spread in the plant.

Exemplary plant pathogens include, but are not limited to, plant viruses such as Alfamoviruses, Alphacryptoviruses, Badnaviruses, Betacryptoviruses, Bigeminiviruses, Bromoviruses, Bymoviruses, Capilloviruses, Carlaviruses, Carmoviruses, Cauliomviruses, Closteroviruses, Comoviruses, Cucumoviruses, Cytorhabdoviruses, Dianthoviruses, Enamoviruses, Fabaviruses, Fijiviruses, Furoviruses, Hordeiviruses, Hybrigeminiviruses, Idaeoviruses, Rarviruses, Ipomoviruses, Luteoviruses, Machlomoviruses, Macluraviruses, Marafiviruses, Monogeminiviruses, Nanaviruses, Necroviruses, Nepoviruses, Nucleorhabdoviruses, Oryzaviruses, Ourmiaviruses, Phytoreoviruses, Potexviruses, Potyviruses, Rymoviruses, satellite RNAs, satelliviruses, Sequiviruses, Sobemoviruses, Tenuiviruses, Tobamoviruses, Tobraviruses, Tombusviruses, Tospoviruses, Trichoviruses, Tymoviruses, Umbraviruses, Varicosaviruses and Waikaviruses; fungal pathogens such as smuts (e.g. Ustilaginales), rusts (Uredinales), ergots (*Clavicepts pupurea*) and mildew; molds (Oomycetes) such as *Phytophthora infestans* (potato blight); bacterial pathogens such as *Erwinia* (e.g., *E. herbicola*), *Pseudomonas* (e.g., *P. aeruginosa, P. syringae; P. fluorescense* and *P. putida*), *Ralstonia* (e.g., *R. solanacearum*), *Agrobacterium* and *Xanthomonas*; roundworms (Nematoda); and Phytomyxea (*Polymyxa* and *Plasmodiophora*).

The disclosed methods for targeted recombination can be used to replace any genomic sequence with a homologous, non-identical sequence. For example, a mutant genomic sequence can be replaced by its wild-type counterpart, thereby providing methods for treatment of plant diseases; provide resistance to plant pathogens; increase crop yields, etc. In like fashion, one allele of a gene can be replaced by a different allele using the methods of targeted recombination disclosed herein.

In many of these cases, a region of interest comprises a mutation, and the donor polynucleotide comprises the corresponding wild-type sequence. Similarly, a wild-type genomic sequence can be replaced by a mutant sequence, if such is desirable. For example, overexpression of an oncogene can be reversed either by mutating the gene or by replacing its control sequences with sequences that support a lower, non-pathologic level of expression. Indeed, any pathology dependent upon a particular genomic sequence, in any fashion, can be corrected or alleviated using the methods and compositions disclosed herein.

Targeted cleavage and targeted recombination can also be used to alter non-coding sequences (e.g., regulatory sequences such as promoters, enhancers, initiators, terminators, splice sites) to alter the levels of expression of a gene product. Such methods can be used, for example, for therapeutic purposes, functional genomics and/or target validation studies.

Targeted modification of chromatin structure, as disclosed in co-owned WO 01/83793; can be used to facilitate the binding of fusion proteins to cellular chromatin.

In additional embodiments, one or more fusions between a zinc finger binding domain and a recombinase (or functional fragment thereof) can be used, in addition to or instead of the zinc finger-cleavage domain fusions disclosed herein, to facilitate targeted recombination. See, for example, co-owned U.S. Pat. No. 6,534,261 and Akopian et al. (2003) *Proc. Natl. Acad. Sci. USA* 100:8688-8691.

In additional embodiments, the disclosed methods and compositions are used to provide fusions of ZFP binding domains with transcriptional activation or repression domains that require dimerization (either homodimerization or heterodimerization) for their activity. In these cases, a fusion polypeptide comprises a zinc finger binding domain and a functional domain monomer (e.g., a monomer from a dimeric transcriptional activation or repression domain). Binding of two such fusion polypeptides to properly situated target sites allows dimerization so as to reconstitute a functional transcription activation or repression domain.

Furthermore, as disclosed above, the methods and compositions set forth herein can be used for targeted integration of exogenous sequences into a region of interest in the genome of a cell, for example in which cleavage enhances insertion via homology-dependent mechanisms (e.g., insertion of a donor sequence comprising an exogenous sequence together with one or more sequences that are either identical, or homologous but non-identical, with a predetermined genomic sequence (i.e., a target site)).

The donor sequence typically contains sufficient homology, in the regions flanking the exogenous sequence, to support homology-directed repair of a double-strand break in a genomic sequence, thereby inserting the exogenous sequence at the genomic target site. Therefore, the donor nucleic acid can be of any size sufficient to support integration of the exogenous sequence by homology-dependent repair mechanisms (e.g., homologous recombination). Without wishing to be bound by any particular theory, the regions of homology flanking the exogenous sequence are thought to provide the broken chromosome ends with a template for re-synthesis of the genetic information at the site of the double-stranded break. In certain embodiments two of the identical sequences or two of the homologous but non-identical sequences (or one of each) are present, flanking the exogenous sequence. An exogenous sequence (or exogenous nucleic acid or exogenous polynucleotide) is one that contains a nucleotide sequence that is not normally present in the region of interest.

Exemplary exogenous sequences include, but are not limited to, cDNAs, promoter sequences, enhancer sequences, epitope tags, marker genes, cleavage enzyme recognition sites and various types of expression constructs. See, for example, U.S. Pat. No. 6,833,252. Additional exemplary homing endonucleases include I-CeuI, PI-PspI, PI-Sce, I-SceIV, I-CsmI, I-PanI, I-SceII, I-PpoI, I-SceIII, I-CreI, I-TevI, I-TevII and I-TevIII. Their recognition sequences are known. See also U.S. Pat. No. 5,420,032; Belfort et al. (1997) *Nucleic Acids Res.* 25:3379-3388; Dujon et al. (1989) *Gene* 82:115-118; Perler et al. (1994) *Nucleic Acids Res.* 22, 1125-1127; Jasin (1996) *Trends Genet.* 12:224-228; Gimble et al. (1996) *J. Mol. Biol.* 263:163-180; Argast et al. (1998) *J. Mol. Biol.* 280:345-353 and the New England Biolabs catalogue.

Marker genes include, but are not limited to, sequences encoding proteins that mediate antibiotic resistance (e.g., ampicillin resistance, neomycin resistance, G418 resistance, puromycin resistance), sequences encoding colored or fluorescent or luminescent proteins (e.g., green fluorescent protein, enhanced green fluorescent protein, red fluorescent protein, luciferase), and proteins which mediate enhanced cell growth and/or gene amplification (e.g., dihydrofolate reductase). Exemplary marker genes thus include, but are not limited to, β-glucuronidase (GUS), phosphinothricin N-acetyl transferase (PAT, BAR), neomycin phosphotransferase, β-lactamase, catechol dioxygenase, α-amylase, tyrosinase, β-galactosidase, luciferase, aequorin, EPSP synthase, nitrilase, acetolactate synthase (ALS), dihydrofolate reductase (DHFR), dalapon dehalogenase and anthranilate synthase. In certain embodiments, targeted integration is used to insert a RNA expression construct, e.g., sequences responsible for regulated expression of micro RNA or siRNA. Promoters, enhancers and additional transcription regulatory sequences, as described above, can also be incorporated in a RNA expression construct.

EXAMPLES

Example 1

Design and Generation of Target Vector

A. Overall Structure of the Target Sequence

Figure 1B:
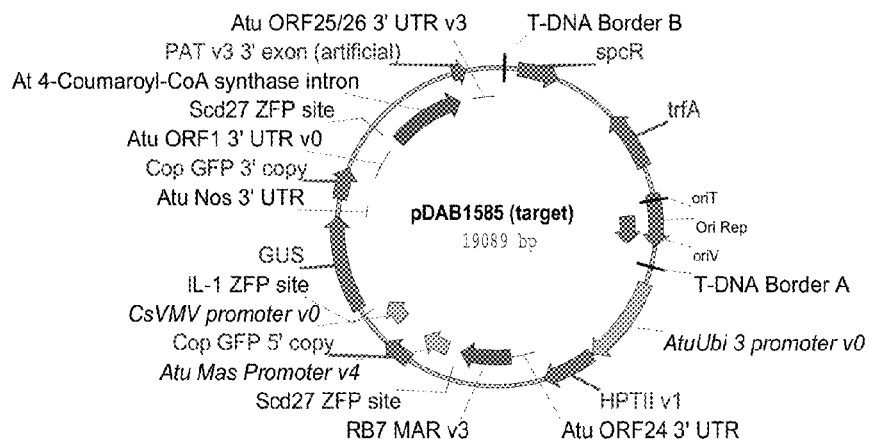

The target construct for tobacco (a dicot) included the following 7 components as shown in FIG. 1: i) a hygromycin phosphotransferase (HPT) expression cassette comprising an *A. thaliana* ubiquitin-3 (ubi-3) promoter (Callis, et al., 1990, J. Biol. Chem. 265-12486-12493) driving the *E. coli* HPT gene (Waldron et al., 1985, *Plant Mol. Biol.* 18:189-200) terminated by an *A. tumifaciens* open reading frame-24 (orf-24) 3' untranslated region (UTR) (Gelvin et al., 1987, EP222493); ii) homologous sequence-1, comprising the *N. tabacum* RB7 matrix attachment region (MAR) (Thompson et al., 1997, WO9727207); iii) a 5' Green Fluorescent Protein (GFP) gene fragment (Evrogen Joint Stock Company, Moscow, Russia) driven by a modified *A. tumifaciens* mannopine synthase (Δmas) promoter (Petolino et al., U.S. Pat. No. 6,730,824); iv) a β-glucuronidase (GUS) expression cassette comprising a Cassava Vein Mosaic Virus (CsVMV) promoter (Verdaguer et al., 1996, Plant Molecular Biology 31:1129-1139) driving a GUS gene (Jefferson, 1987, *Plant Mol. Biol. Rep.* 5:387-405) terminated by the *A. tumifaciens* nopaline synthase (nos) 3'UTR (DePicker et al., 1982, J. Mol. Appl. Genet. 1:561-573); v) a 3' GFP gene fragment (Evrogen Joint Stock Company, Moscow, Russia) terminated by an *A. tumifaciens* orf-1 3' UTR (Huang et al., J. Bacteriol. 172:1814-1822); vi) homologous sequence-2, comprising *A. thaliana* 4-coumaroyl-CoA synthase (4-CoAS) intron-1 (Locus At3g21320, GenBank N.C. 003074) and; vii) a *S. viridochromogenes* phosphinothricin phosphotransferase (PAT) (Wohlleben et al., 1988, Gene 70:25-37) 3' gene fragment terminated by *A. tumifaciens* ORF-25/26 3' UTR (Gelvin et al., 1987, EP222493).

A zinc finger-Fok1 fusion protein binding site (IL-1-L0-Fok1) (Urnov et al., 2005, US 2005/0064474) was inserted down stream of the CsVMV promoter (Verdaguer et al., 1996, Plant Molecular Biology 31:1129-1139) and fused with the GUS coding sequence (Jefferson, 1987, Plant Mol. Biol. Rep. 5:387-405) at the N-terminal. Two copies of a second zinc finger-Fok1 fusion protein binding site (Scd27-L0-Fok1) (Urnov et al., 2005, US 2005/0064474) flanked the 5' and 3' GFP gene fragments (Evrogen Joint Stock Company, Moscow, Russia). Each binding site contained four tandem repeats of the recognition sequence of the particular zinc finger-Fok1 fusion protein so that each binding site was ~200 bp in size (FIG. 2a). This was designed to ensure that the recognition sequences would be accessible to the zinc finger-Fok1 fusion protein in the complex chromatin environment. Each recognition sequence included an inverted repeat sequence to which a single zinc finger-Fok1 fusion protein bound as a homodimer and cleaved the double stranded DNA (FIG. 2b). The 5' and 3' GFP gene fragments overlapped by 540 bp providing homology within the target sequence and a stop codon was inserted at the 3' end of the 5' GFP fragment to ensure no functional GFP translation from the target sequence. The transformation vector comprising the target sequence was generated through a multiple-step cloning process as described below.

B. Construction of the HPT Binary Vector (pDAB1584)

The vector pDAB1400, which contained a GUS expression cassette, comprising an *A. thaliana* ubi-3 promoter (Callis, et al., 1990, J. Biol. Chem. 265-12486-12493) driving the GUS gene (Jefferson, 1987, Plant Mol. Biol. Rep. 5:387-405) terminated by *A. tumifaciens* orf-1 UTR (Huang et al., J. Bacterial. 172:1814-1822), was used as the starting base construct (FIG. 3).

Figure 4:
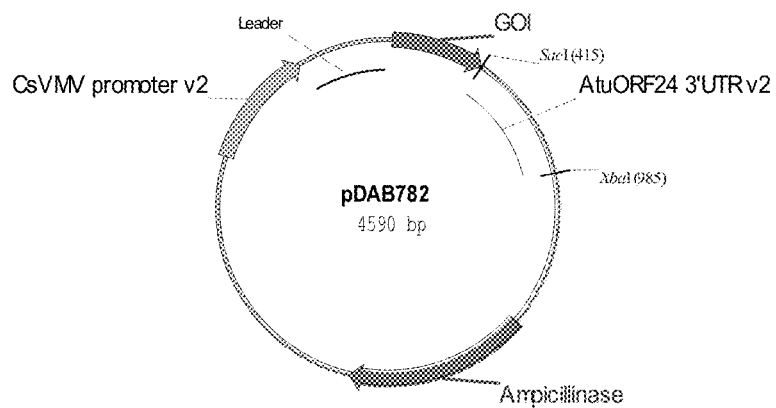
FIG. 4 is a schematic representation of the plasmid pDAB782.
Figure 5:
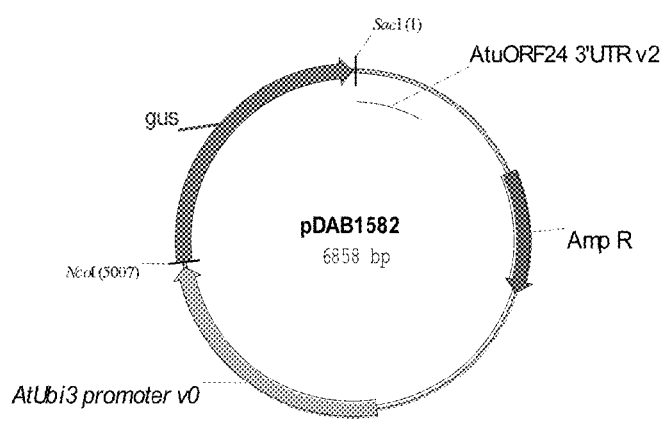
FIG. 5 is a schematic representation of the plasmid pDAB1582.

To avoid any unnecessary repeated regulatory elements in the target construct, the *A. tumifaciens* orf-1 UTR (Huang et al., J. Bacteriol. 172:1814-1822) in pDAB1400 was replaced with an *A. tumifaciens* orf-24 UTR (Gelvin et al., 1987, EP222493), which was excised from pDAB782 (FIG. 4) as a SacI/XbaI fragment and cloned into the same sites in pDAB1400. The resulting construct contained an *A. thaliana* ubi-3 promoter (Callis, et al., 1990, J. Biol. Chem. 265-12486-12493) driving the GUS gene (Jefferson, 1987, Plant Mol. Biol. Rep. 5:387-405) terminated by an *A. tumifaciens* orf-24 UTR (Gelvin et al., 1987, EP222493) and was named pDAB1582 (FIG. 5).

Figure 6:
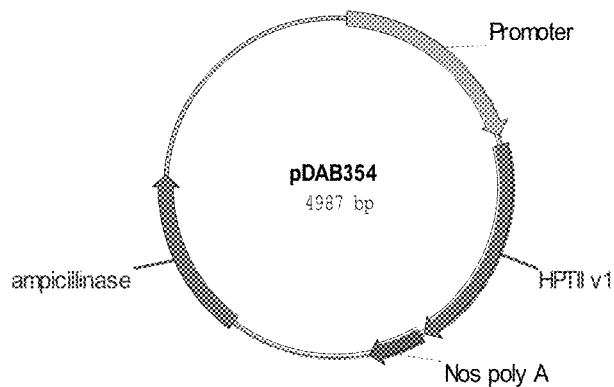
FIG. 6 is a schematic representation of the plasmid pDAB354.
Figure 7:
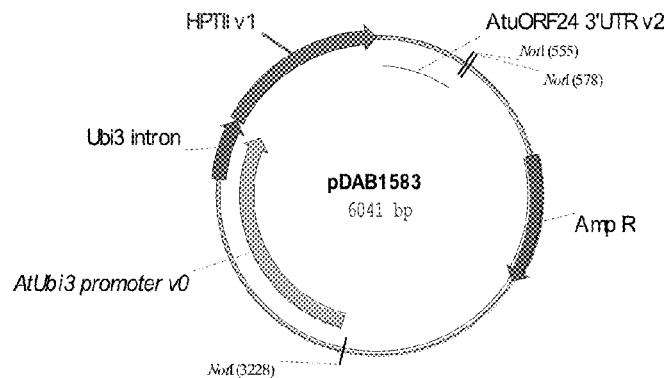
FIG. 7 is a schematic representation of the plasmid pDAB1583.

The HPT coding sequence (Waldron et al., 1985, Plant Mol. Biol. 18:189-200) was PCR amplified from pDAB354 plasmid (FIG. 6) using the primers P1 and P2. A BbsI site was added at the 5' end of primer P1 and the SacI site was retained at the 3' end of primer P2. The HPTII PCR fragment was digested with BbsI/SacI and cloned into pDAB1582 digested with NcoI-SacI to replace the GUS gene with the HPT gene from the PCR fragment. The resulting plasmid was named pDAB1583 (FIG. 7).

Figure 8:
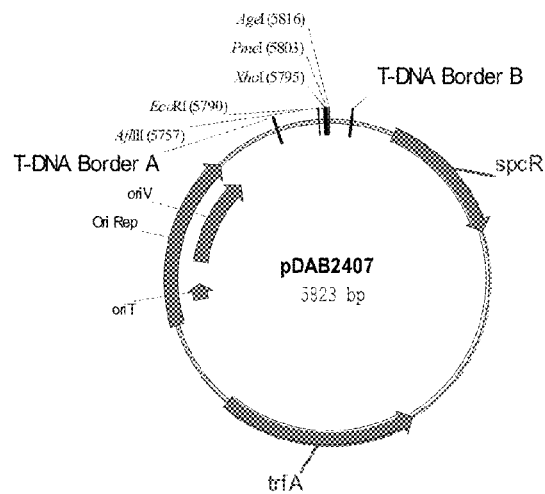
FIG. 8 is a schematic representation of the plasmid pDAB2407.
Figure 9:
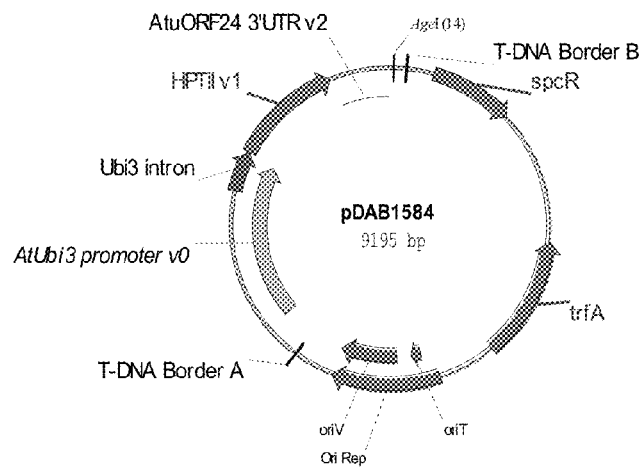
FIG. 9 is a schematic representation of the plasmid pDAB1584.

The *A. thaliana* ubi-3/HPT/*A. tumifaciens* orf-24 fragment was then excised from pDAB1583 by NotI digestion and treated with T4 DNA polymerase to generate blunt-ends. The blunt-end-treated HPT expression cassette was cloned into pDAB2407 (FIG. 8), a binary base vector, at the PmeI site resulting in plasmid pDAB1584 (FIG. 9).

C. Construction of the Vector Comprising the Homologous Sequences and the Scd27 Zinc Finger-Fok1 Fusion Protein Binding Site (pDAB1580)

Figure 10:
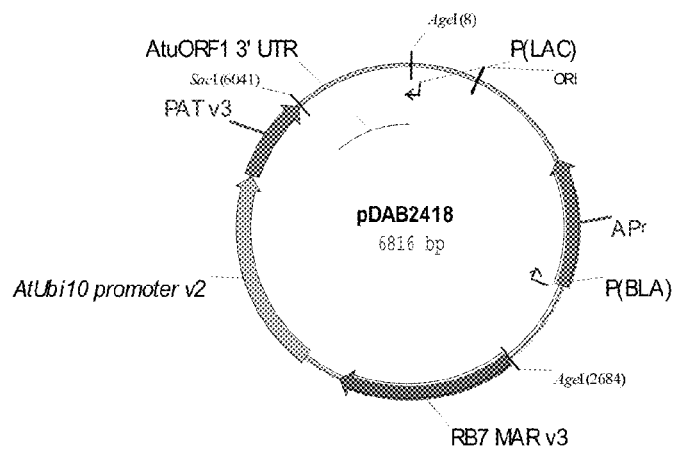
FIG. 10 is a schematic representation of the plasmid pDAB2418.
Figure 11:
FIG. 11 is a schematic representation of the plasmid pDAB4045.
Figure 12:
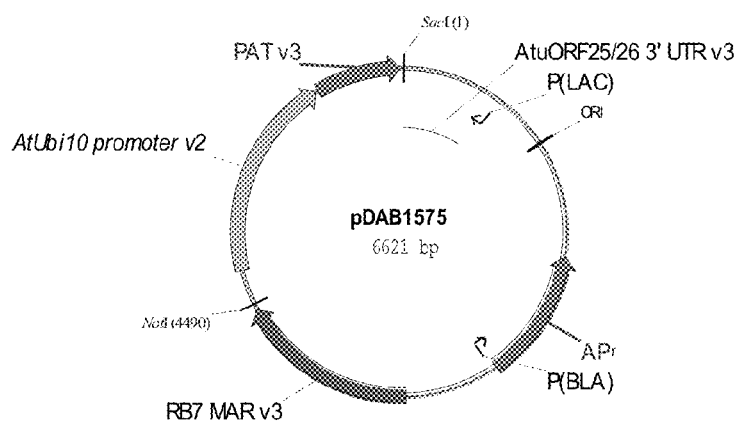
FIG. 12 is a schematic representation of the plasmid pDAB1575.

The *A. tumefaciens* orf-1 UTR (Huang et al., J. Bacteriol. 172:1814-1822) in pDAB2418 (FIG. 10) was replaced with the *A. tumefaciens* orf25/26 UTR (Gelvin et al., 1987, EP222493) to avoid repeated regulatory sequences in the target vector. To make the UTR swap, the *A. tumefaciens* orf25/26 UTR (Gelvin et al., 1987, EP222493) was PCR amplified from the pDAB4045 plasmid (FIG. 11) using primers P3 and P4. SmaI and AgeI sites were added to the 3' end of PCR fragment, and the SacI site was retained at the 5' end. The pDAB2418 plasmid DNA, which contained a PAT gene expression cassette comprising the *A. thaliana* ubiquitin-10 (ubi-10) promoter (Callis, et al., 1990, J. Biol. Chem. 265-12486-12493) driving the PAT gene (Wohlleben et al., 1988, Gene 70:25-37) terminated by the *A. tumefaciens* orf-1 UTR (Huang et al., J. Bacteriol. 172:1814-1822)

and a *N. tabacum* RB7 MAR sequence (Thompson et al., 1997, WO9727207), was digested with SacI and AgeI and the two largest fragments were recovered. These fragments were ligated with the *A. tumefaciens* orf25/26 UTR (Gelvin et al., 1987, EP222493) PCR product digested with SacI and AgeI. The resulting plasmid was named pDAB1575 (FIG. 12). The *N. tabacum* RB7 MAR (Thompson et al., 1997, WO9727207) serves as homologous sequence-1 in the target vector.

Figure 13:
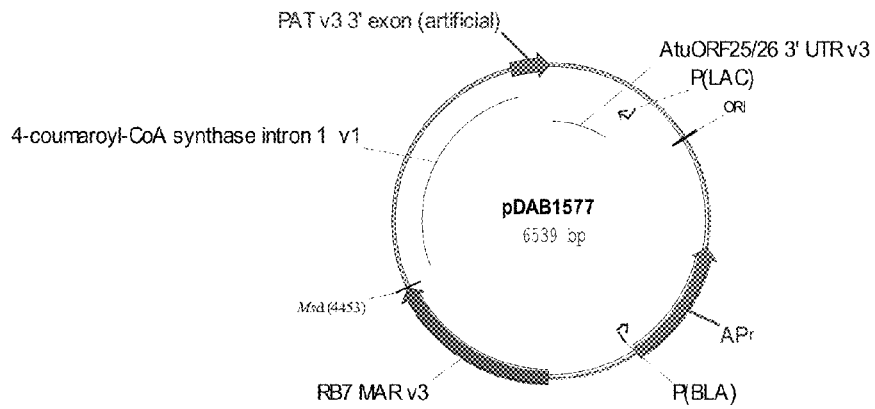
FIG. 13 is a schematic representation of the plasmid pDAB1577.

Intron-1 of *A. thaliana* 4-CoAS (Locus At3g21320, GenBank N.C. 003074) was selected to serve as homologous sequence-2 in the target vector. The PAT gene (Wohlleben et al., 1988, Gene 70:25-37) coding sequence was analyzed and the 299/300 bp downstream of the start codon was identified as the site for inserting the intron so that the appropriate 5' and 3' splicing sites would be formed. The full-length intron was then fused with 253 bp of 3' partial PAT coding sequence by DNA synthesis (Picoscript Ltd., LLP, Houston, Tex.). NotI and SacI sites were added to the 5' and 3' end of the DNA fragment, respectively. The synthesized DNA fragment was then digested with NotI/SacI and inserted into pDAB1575 at the same sites to replace the full-length PAT coding sequence. The resulting construct was named pDAB1577 (FIG. 13).

Figure 14:
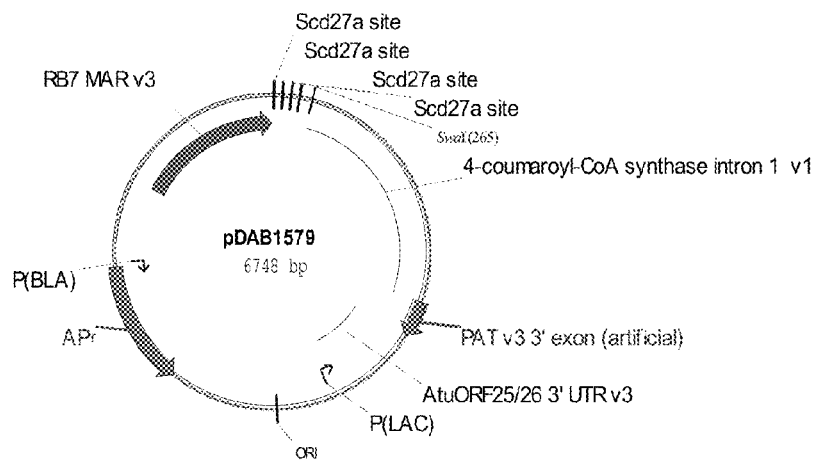
FIG. 14 is a schematic representation of the plasmid pDAB1579.
Figure 15:
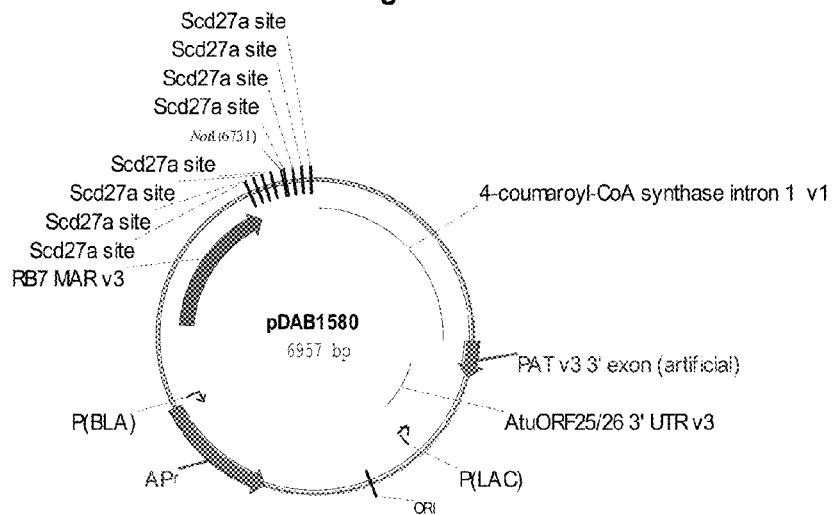
FIG. 15 is a schematic representation of the plasmid pDAB1580.

A 241 bp DNA fragment containing 4 tandem repeats of Scd27-L0-Fok1 (FIG. 2) was synthesized (Picoscript Ltd., LLP, Houston, Tex.) with a SmaI site added to both 5' and 3' ends of the fragment. The synthesized zinc finger-Fok1 binding site-containing fragment was then digested with SmaI and inserted into pDAB1577 at MscI site. The resulting vector was named pDAB1579 (FIG. 14). A second SmaI-digested zinc finger-Fok1 binding site-containing fragment was then inserted into pDAB1579 at the SwaI site. The resulting construct was named pDAB1580 (FIG. 15). This vector contains homologous sequences 1 and 2 (*N. tabacum* RB7 MAR and *A. thaliana* 4-CoAS intron1, respectively) and two synthesized Scd27 zinc finger-Fok1 binding sites, each containing 4 tandem repeats of Scd27-L0-Fok1 recognition sites.

D. Construction of the Vector Containing Two Partially Duplicated Non-Functional GFP Fragments (pDAB1572)

Figure 16:
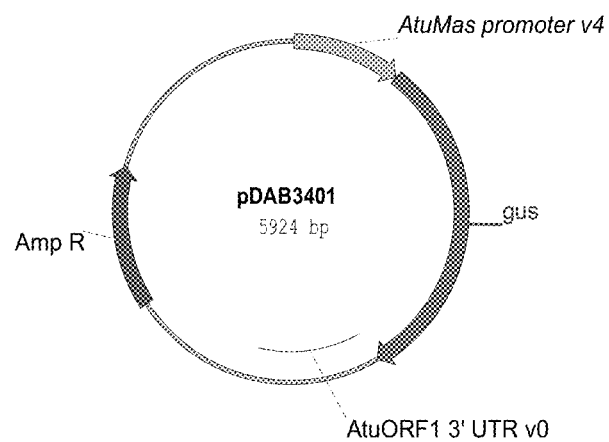
FIG. 16 is a schematic representation of the plasmid pDAB3401.
Figure 17:
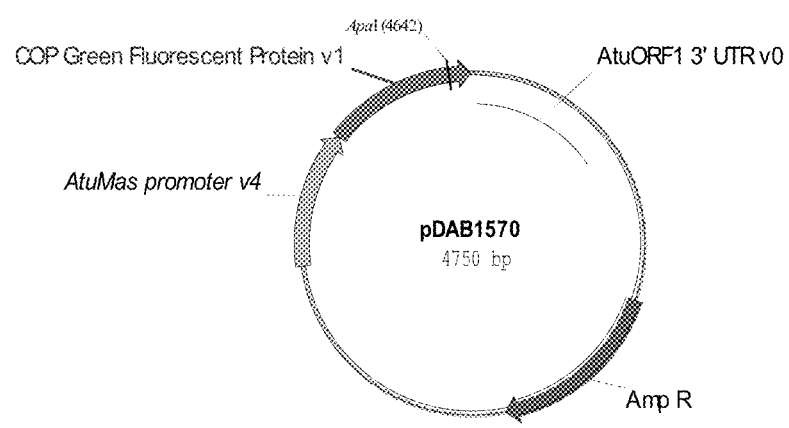
FIG. 17 is a schematic representation of the plasmid pDAB1570.

The GFP gene, CopGFP, was purchased from Evrogen Joint Stock Company (Moscow, Russia) and the full-length coding sequence was PCR amplified using primers P5 and P6. BbsI and SacI sites were added to the 5' and 3' ends of the PCR product, respectively. The CopGFP PCR product was then digested with BbsI/SacI and cloned into pDAB3401 (FIG. 16) comprising the modified *A. tumifaciens* Δmas promoter (Petolino et al., U.S. Pat. No. 6,730,824) driving the GUS gene (Jefferson, 1987, Plant Mol. Biol. Rep. 5:387-405) and terminated by *A. tumifaciens* orf-1 3' UTR (Huang et al., J. Bacteriol. 172:1814-1822) at the NcoI/SacI sites to replace the GUS gene. The resulting vector was named pDAB1570 (FIG. 17).

Figure 18:
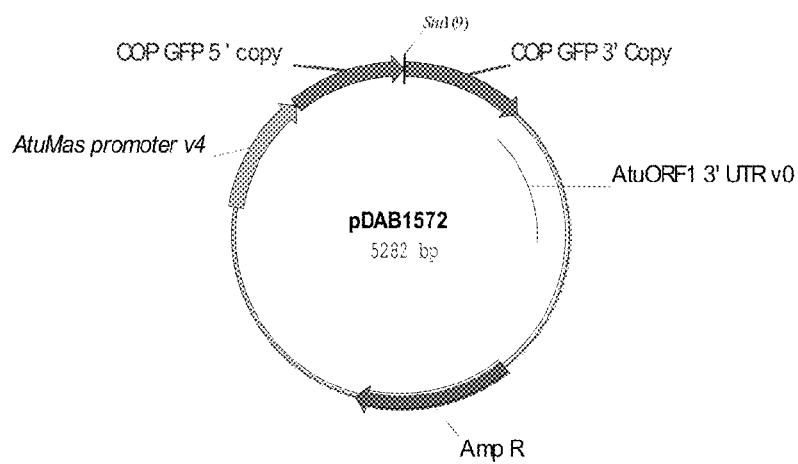
FIG. 18 is a schematic representation of the plasmid pDAB1572.

To make the two partially duplicated, non-functional GFP fragments, a DNA fragment containing the majority of the coding sequence of CopGFP with a 47 bp deletion at the 5' end was PCR amplified using primers P9 and P10. An ApaI site was added to both the 5' and 3' ends and an additional StuI site was added to the 5' end downstream of the ApaI site. The PCR product was then digested with ApaI and inserted into pDAB1570 at the ApaI site, thereby creating two non-functional GFP fragments in the same vector with a 540 bp duplicated sequence. The resultant construct was named pDAB1572 (FIG. 18).

E. Construction of the Vector Containing the IL-1 Zinc Finger-Fok1 Fusion Protein Binding Site/Gus Gene Fusion (pDAB1573)

Figure 19:
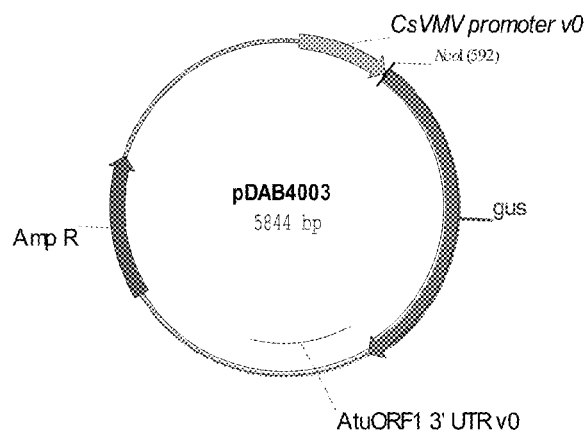
FIG. 19 is a schematic representation of the plasmid pDAB4003.
Figure 20:
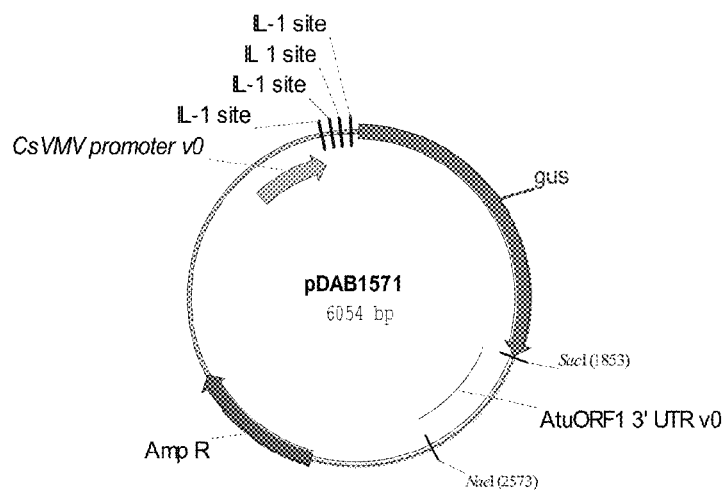
FIG. 20 is a schematic representation of the plasmid pDAB1571.

A 233 bp DNA fragment containing 4 tandem repeats of IL-1_L0-Fok1 recognition site (FIG. 2) was synthesized by Picoscript Ltd., LLP, (Houston, Tex.) with NcoI and AflIII sites added to the 5' and 3' ends, respectively. The synthesized fragment was then digested with NcoI/AflIII and inserted into pDAB4003 (FIG. 19), which contained a GUS gene (Jefferson, 1987, Plant Mol. Biol. Rep. 5:387-405) driven by a CsVMV promoter (Verdaguer et al., 1996, Plant Molecular Biology 31:1129-1139) terminated by *A. tumefaciens* orf-1 3' UTR (Huang et al., J. Bacteriol. 172:1814-1822) at NcoI site. An N-terminal fusion between IL-1_L0-Fok1 binding site and GUS coding sequence was then generated. The resulting vector was named pDAB1571 (FIG. 20).

Figure 21:
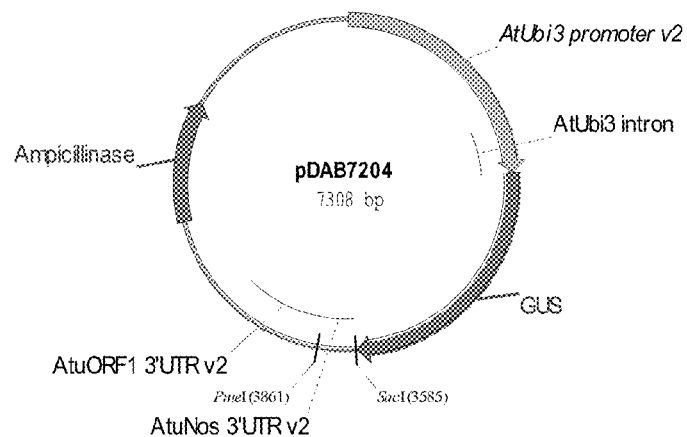
FIG. 21 is a schematic representation of the plasmid pDAB7204.
Figure 22:
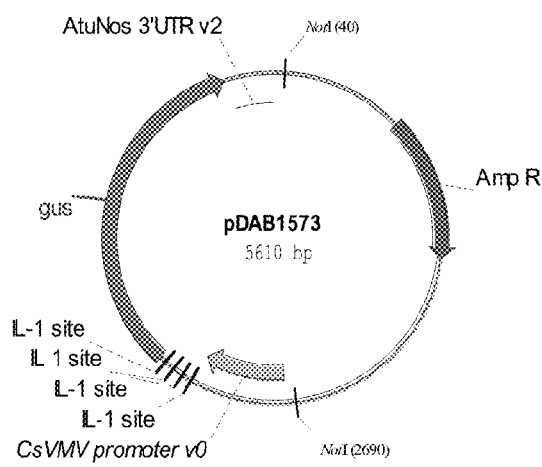
FIG. 22 is a schematic representation of the plasmid pDAB1573.

To avoid repeat 3' UTR elements in the target vector, the *A. tumefaciens* nos 3' UTR (DePicker et al., 1982, J. Mol. Appl. Genet. 1:561-573) was excised from pDAB7204 (FIG. 21) as a SacI/PmeI fragment and cloned into pDAB1571, which was digested with SacI/NaeI, to replace the *A. tumefaciens* orf-1 3' UTR (Huang et al., J. Bacteriol. 172:1814-1822). The resulting plasmid was named pDAB1573 (FIG. 22).

F. Construction of the Final Target Vector (pDAB1585)

Figure 23:
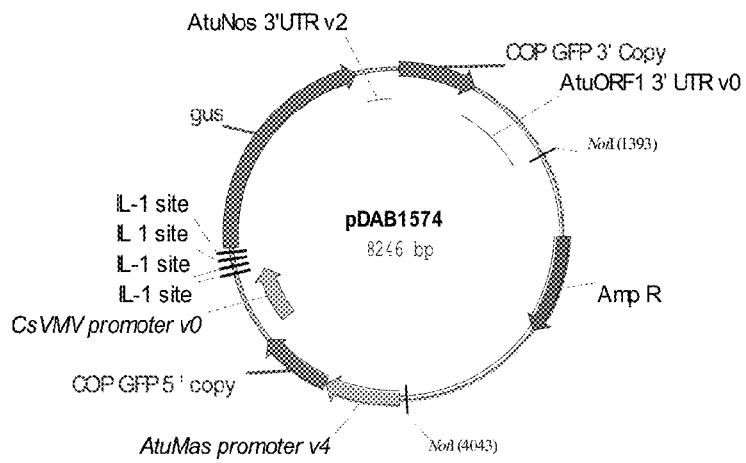
FIG. 23 is a schematic representation of the plasmid pDAB1574.
Figure 24:
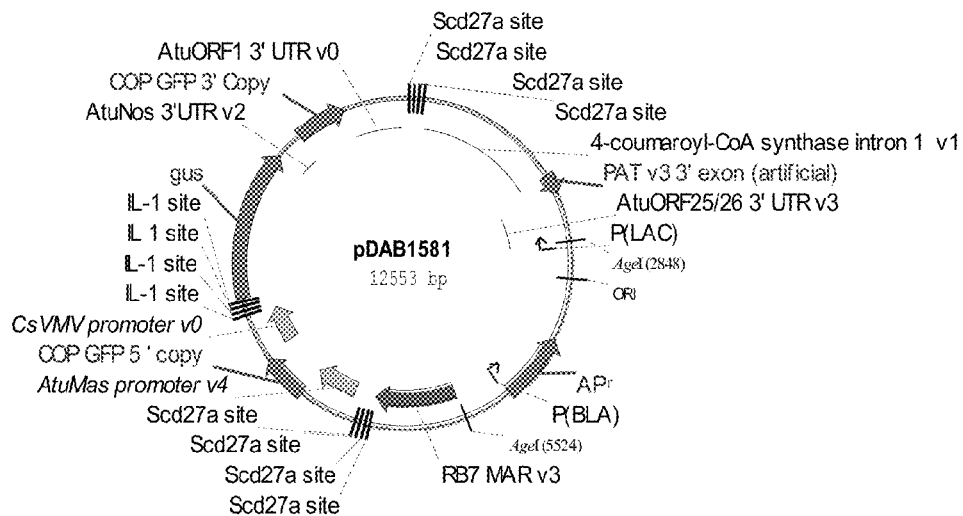
FIG. 24 is a schematic representation of the plasmid pDAB1581.

To make to final target vector, the GUS expression cassette with the IL-1-Fok1 fusion protein target site insertion was excised from pDAB1573 by NotI digestion, blunt-end treated and inserted into pDAB1572 at StuI site. The resulting intermediate vector was named pDAB1574 (FIG. 23). The entire cassette containing the modified Δmas promoter (Petolino et al., U.S. Pat. No. 6,730,824) a 5' partially duplicated GFP sequence (Evrogen Joint Stock Company, Moscow, Russia), the CsVMV promoter (Verdaguer et al., 1996, Plant Molecular Biology 31:1129-1139), an IL-1-Fok1 fusion protein target sequence, the GUS gene (Jefferson, 1987, Plant Mol. Biol. Rep. 5:387-405) coding region, an *A. tumefaciens* nos 3' UTR (DePicker et al., 1982, J. Mol. Appl. Genet. 1:561-573), a 3' partially duplicated GFP (Evrogen Joint Stock Company, Moscow, Russia) and *A. tumefaciens* orf-1 3' UTR (Huang et al., J. Bacteriol. 172:1814-1822) was excised from pDAB1574 and inserted into pDAB1580 at the NotI site. The resulting plasmid was named pDAB1581 (FIG. 24).

The AgeI fragment of pDAB1581 was then inserted into pDAB1584 at AgeI site thereby creating the final target construct, pDAB1585 (FIG. 1).

Example 2

Generation of Transgenic Cell Lines with Integrated Target Sequences

Two different tobacco cell suspension cultures were used into which target sequences of Example 1 were stably integrated via *Agrobacterium* transformation. The first culture, referred to as NT1, was obtained from Arnold Bendich of the University of Washington, Seattle, Wash., USA. This culture proliferates as 15-20 μdiameter cells in 20-30 cell clusters with a doubling time of approximately 48 hours. NT1 cell suspension cultures were maintained in media containing MS basal salts (PhytoTechnology Labs M524), 137.4 mg/L $K_2HPO_4$, 30 g/L sucrose, 2.22 mg/L 2,4-D, 1 mg/L thiamine-HCL, 100 mg/L myo-inositol and 0.5 g/L MES at a pH of 5.7. The NT1 cells were sub-cultured every 7 days by adding 40 mL of fresh MS-based medium to 1 mL packed cell volume (PCV).

The second tobacco cell culture used, referred to as BY2, was obtained from Jun Ueki of Japan Tobacco, Iwata, Shizuoka, Japan. This culture proliferates as 5-10 μdiameter cells in 100-150 cell clusters with a doubling time of roughly 18 hours. BY2 cell suspension cultures were maintained in media containing LS basal salts (PhytoTechnology Labs L689), 170 mg/L $KH_2PO_4$, 30 g/L sucrose, 0.2 mg/L 2,4-D and 0.6 mg/L thiamine-HCL at a pH of 6.0. The BY2 cells were sub-cultured every 7 days by adding 50 mL of LS-based medium to 0.25 mL PCV. Both NT1 and BY2 cell suspension cultures were maintained in 250-mL flasks on a rotary shaker at 25° C. and 125 RPM.

In order to generate transgenic NT1 and BY2 cell cultures with integrated target sequences, a flask of a four-day post sub-culture tobacco suspension was divided into 10-12 four mL aliquots which were co-cultivated in 100×25 mm Petri dishes with 100 μL Agrobacterium strain LBA4404 harboring pDAB1585 grown overnight to an $OD_{600}$~1.5. Dishes were wrapped with parafilm and incubated at 25° C. without shaking for 3 days after which excess liquid was removed and replaced with 11 mL of basal medium (MS- or LS-based for NT1 and BY2, respectively) containing 500 mg/L carbenicillin.

Following re-suspension of the tobacco cells, 1 mL suspension was dispensed onto 100×25 mm plates of appropriate base medium containing 500 mg/L carbenicillin and 200 mg/L hygromycin solidified with 8 g/L TC agar, and incubated unwrapped at 28° C. in the dark. This resulted in 120-144 selection plates for a single treatment. Individual hygromycin-resistant isolates appeared 10-14 days after plating (Table 1) and were transferred to individual 60×20 mm plates (one isolate per plate) where they were maintained as callus on a 14-day subculture schedule until needed for analysis and subsequent re-transformation experiments.

TABLE 1

Summary of Transgenic Target Cell Culture Generation

| Tobacco Cell Culture | # of Selection Plates | # of Transgenic Events |
|---|---|---|
| NT1 | 360 | 305 |
| BY2 | 720 | 551 |

Example 3

Screening and Characterization of Target Transgenic Events

The hygromycin-resistant transgenic events generated from the transformation of target vector into either BY2 or NT1 tobacco cell cultures (as described in Example 2) were analyzed as follows.

The initial analyses conducted for screening these transgenic events included GUS expression analysis to indicate the accessibility of the target sequence, PCR analysis of the partial and full-length target sequence to confirm the presence and intactness of target vector and Southern blot analysis to determine the copy number of the integrated target sequence. A subset of the transgenic events that showed GUS expression contained one single copy of full length target sequence; these were selected for re-establishing suspension cultures to generate the target lines for subsequent re-transformation. These re-established target lines were also subjected further characterization, which included more thorough Southern blot analysis, sequencing confirmation of the entire target insert and flanking genomic sequence analysis.

Transgenic tobacco callus tissue or suspension cultures initiated from the selected events were analyzed for GUS activity by incubating 50 mg samples in 150 μL of assay buffer for 24-48 hours at 37° C. The assay buffer consisted of 0.2 M sodium phosphate pH 8.0, 0.1 mM each of potassium ferricyanide and potassium ferrocyanide, 1.0 mM sodium EDTA, 0.5 mg/mL 5-bromo-4-chloro-3-indoyl-β-glucuronide and 0.6% (v/v) Triton X-100 (Jefferson, 1987, Plant Mol. Biol. Rep. 5:387-405). The appearance of blue colored regions was used as the indicator of GUS gene expression, which indicated that the target sequence insertion was transcriptionally active and thus accessible in the local genomic environment.

The GUS expressing transgenic events were assayed by PCR using the primer pair P15/P16 which led to amplification of a 10 kb DNA fragment extending from the 3' UTR of the HTP expression cassette at the 5' end of target sequence to the 3' UTR of the partial PAT gene cassette at the 3' end of the target sequence. Since all of the events were obtained under hygromycin selection, it was assumed that the HPT expression cassette was intact in all of the target events. Therefore, only the 3' UTR of the HPT expression cassette was covered in the full length PCR analysis. A subset of events were also PCR assayed using the primer pairs P15/P17 and P18/P19 to determine the intactness of the 5' and 3' ends of the target sequence, respectively. All target events confirmed with PCR analysis were further assayed by Southern blot analysis to determine the copy number of the integrated target sequence.

Southern blot analysis was carried out for all target events that passed the screening of GUS expression and full-length PCR. Ten μg of genomic DNA was digested with NsiI, which was a unique cutter within the target sequence. The digested genomic DNA was separated on a 0.8% agarose gel and transferred onto a nylon membrane. After cross-linking, the transferred DNA on the membrane was hybridized with an HPT gene probe to determine the copy number of the 5' end of target sequence. The same blot was then stripped and re-hybridized with a PAT gene probe to determine the copy number of the 3' end of the target sequence.

Three events that showed GUS expression and contained a single copy of full-length target sequence were selected for further characterization, which included more thorough Southern blot analysis, entire target sequence confirmation and flanking genomic sequence analysis (Table 2). These three events were BY2-380, NT1-240 and NT1-260. Suspension cultures were re-established from these three events for subsequent re-transformation with vectors comprising donor DNA and zinc finger-Fok1 fusion protein genes.

TABLE 2

Characterization of selected transgenic target cell cultures.

| Cell Line | Events No. | Hygromycin resistance | GUS expression | | PAT copy no. | HPTII copy no. | Full length PCR | 5'PCR | 3'PCR |
|---|---|---|---|---|---|---|---|---|---|
| | | | callus | suspension | | | | | |
| BY2 | 380 | + | + | + | 1 | 1 | + | + | + |
| NT1 | 240 | + | + | + | 1 | 1 | + | + | + |
| NT1 | 260 | + | + | + | 1 | 1 | +* | + | +* |

*with an insertion at the 3' end of the target

To ensure the three suspension cultures established from the target events BY2-380, NT1-240 and NT1-260 contained the intact target sequence as expected, the major target sequence from the 3'UTR of the HPT expression cassette at the 5' end of the target sequence to the 3' UTR of the partial PAT gene cassette at the 3' end of the target sequence was PCR amplified using the primer pair P15/P16 and cloned into pCR2.1 TOPO vector (Invitrogen, Carlsbad, Calif.). The PCR products inserted in the TOPO vector were sequenced by Lark technology, Inc. (Houston, Tex.). The sequence results indicated that while both BY2-380 and NT1-240 had complete target sequences as expected, NT1-260 had a DNA insertion of 5475 bp. The insertion was located 27 bp upstream of the 3' end of the 3' partial PAT sequence. Interestingly, there was an orf of 2883 by in this insertion. A BLAST search of this orf against the NBCI database showed that it matched with a transposon from *Agrobacterium*. Although this target line, NT1-260, may not be suitable for inter-chromosomal homologous recombination experiments because of the extra insertion sequence within the PAT selectable marker gene, it could still be used for testing the intra-chromosomal homologous recombination using the GFP reporter system designed in the target vector.

All three lines were further analyzed to obtain the flanking genomic sequences using the Universal GenomeWalker Kit (Clontech, Mountain View, Calif.). Brief, 2.5 µg of genomic DNA was digested with three blunt-end restriction enzymes, EcoRV, DraI and StuI in separate reactions. The digested DNA was purified through phenol/chloroform extraction and ligated with BD GenomeWalker Adaptor. Nested PCR amplification was performed with the ligation as template and primer P20 (walking upstream of the 5' end of target sequence insertion) and P21 (walking downstream of the 3' end of target sequence insertion) for the primary PCR reaction, and primer P22 (walking upstream of the 5' end of target sequence insertion) and P23 (walking downstream of the 3' end of target sequence insertion) for the secondary nested PCR reaction. The amplified fragments from the secondary PCR reactions were cloned into pCR2.1 TOPO or pCR Blunt II TOPO vector (Invitrogen, Carlsbad, Calif.) and sequenced using a Dye Terminator Cycle Sequencing Kit (Beckman Coulter, Fullerton, Calif.). The flanking genomic sequences were obtained from all of three target lines through this process. Primers were then designed based on the flanking genomic sequences and used to amplify the entire target sequence. The amplified fragments obtained from these target lines were of expected size. Both ends of the amplified fragments were confirmed by sequencing.

Example 4

Design and Generation of Donor DNA Vector

The donor DNA construct included homologous sequence-1 (*N. tabacum* RB7 MAR) (Thompson et al., 1997, WO9727207), a full-length *A. thaliana* ubi 10 promoter (Callis, et al., 1990, J. Biol. Chem. 265-12486-12493), 299 bp of 5' partial PAT gene coding sequence (Wohlleben et al., 1988, Gene 70:25-37) and homologous sequence-2 (*A. thaliana* 4-CoAS intron-1) (Locus At3g21320, GenBank N.C. 003074). Both homologous sequence-1 and sequence-2 in the donor vector were identical to the corresponding homologous sequence-1 and sequence-2 in the target vector (pDAB1585).

Figure 25:
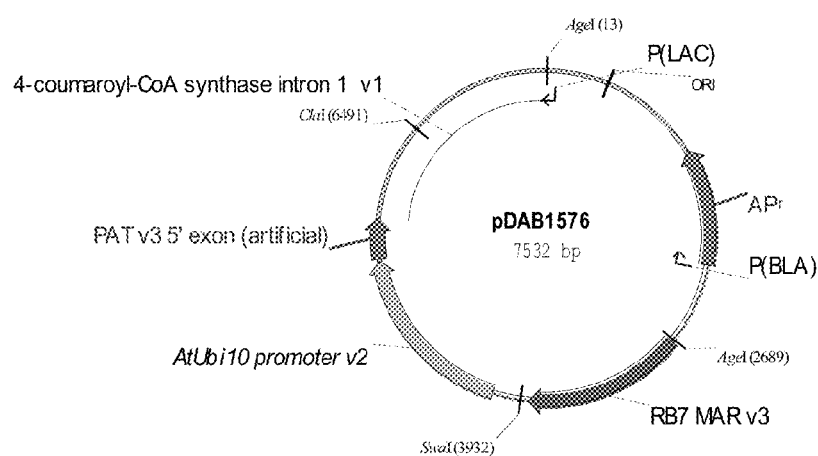
FIG. 25 is a schematic representation of the plasmid pDAB1576.

To construct the donor vector, the 299 bp of 5' partial PAT coding sequence was fused with the full-length *A. thaliana* 4-CoAS intron-1 (Locus At3g21320, GenBank N.C. 003074) through DNA synthesis by Picoscript Ltd., LLP, (Houston, Tex.). NcoI and XhoI sites were added to the 5' and 3' end of the fragment, respectively. This synthesized DNA fragment was then digested with NcoI/XhoI and inserted into pDAB1575 at the same sites to replace the full-length PAT gene coding sequence and its 3' UTR. The resulting construct was named pDAB1576 (FIG. 25).

pDAB1576 was then digested with AgeI and the entire fragment containing the 5' partial PAT expression cassette flanked by homologous sequence-1 and homologous sequence-2 was inserted into pDAB2407, the binary base vector, at the same site. The resultant construct was named pDAB1600 and was the binary version of the donor vector for plant cell re-transformation (FIG. 26).

Example 5

Design and Generation of Zinc Finger Nuclease Expression Vector

Figure 28:
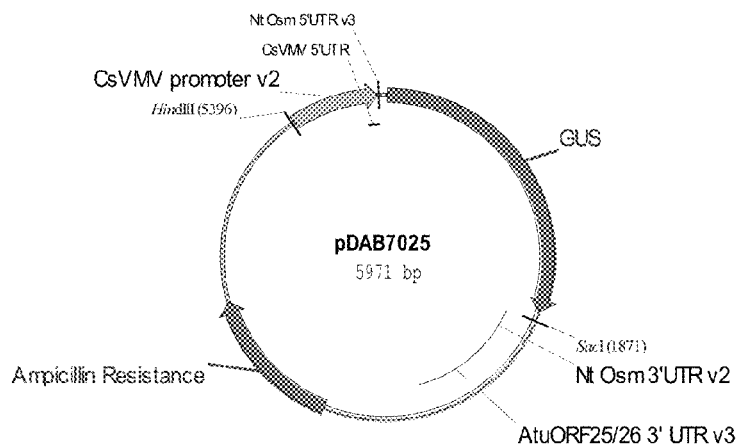
FIG. 28 is a schematic representation of the plasmid pDAB7025.
Figure 29:
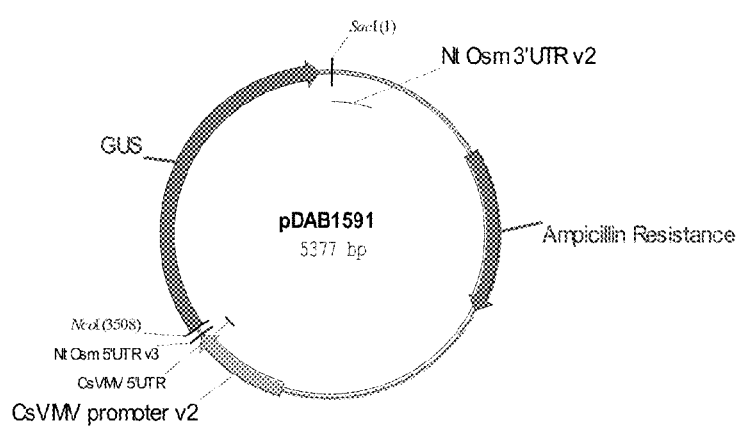
FIG. 29 is a schematic representation of the plasmid pDAB1591.

The zinc finger-Fok1 fusion protein gene was driven by a CsVMV promoter and 5' UTR (Verdaguer et al., 1996, Plant Molecular Biology 31:1129-1139). Also included in the cassette were *N. tabacum* osmotin 5' and 3' UTRs (Merlo et al., US2005102713). To make these vectors, the HindIII/SacI fragment comprising CsVMV promoter and 5'UTR driving PAT in pDAB7002 (FIG. 27) was replaced with a fragment comprising CsVMV promoter and 5' UTR and *N. tabacum* 5' UTR driving GUS, which was excised from pDAB7025 (FIG. 28) with HindIII/SacI. The resultant plasmid was named as pDAB1591 (FIG. 29).

Figure 30:
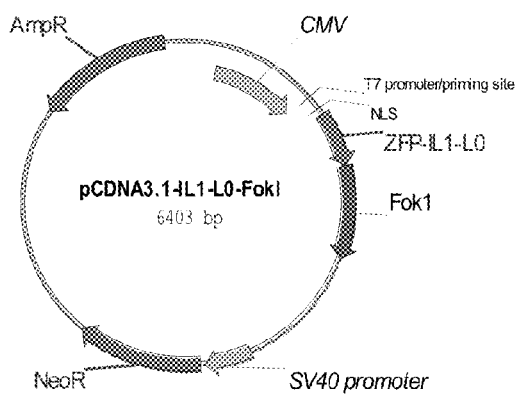
FIG. 30 is a schematic representation of the plasmid pcDNA3.1-IL1-L0-FokI.
Figure 31:
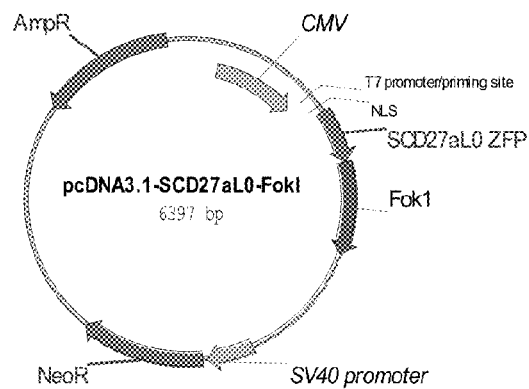
FIG. 31 is a schematic representation of the plasmid pcDNA3.1-SCD27-L0-FokI.
Figure 32:
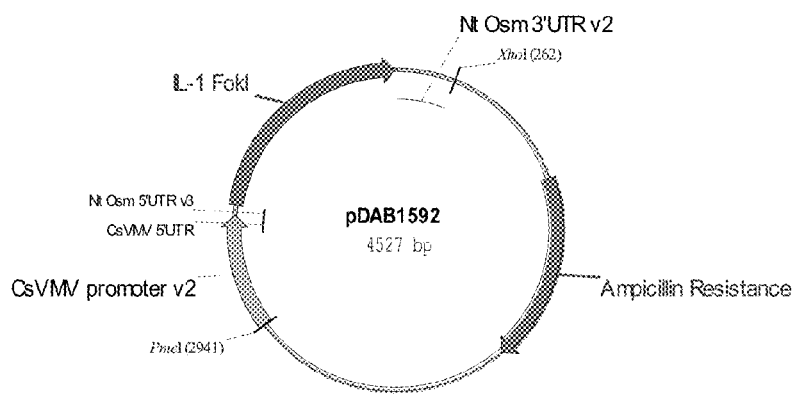
FIG. 32 is a schematic representation of the plasmid pDAB1592.
Figure 33:
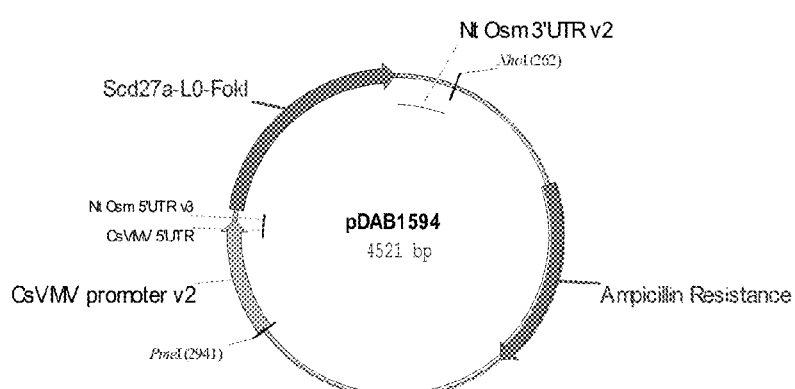
FIG. 33 is a schematic representation of the plasmid pDAB1594.

The IL1-L0-Fok1 and Scd27-L0-Fok1 coding sequences were PCR amplified from their original vectors, pcDNA3.1-IL1-L0-FokI (FIG. 30) and pcDNA3.1-SCD27a-L0-FokI (FIG. 31) using primer pair P11/P12 and P13/P14, respectively. BbsI and SacI sites were added to the 5' and 3' end of the PCR fragments, respectively. The PAT gene in pDAB1591 was replaced with the zinc finger fusion protein gene PCR fragment through SacI/NcoI cloning. The resultant plasmids were named pDAB1592 (FIG. 32) and pDAB1594 (FIG. 33) for IL-1-Fok1 and Scd27-Fok1 , respectively.

Figure 34A:
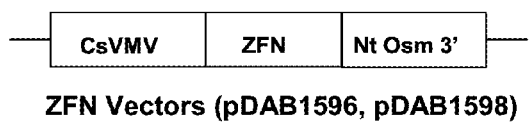
FIGS. 34A through C are schematic representations of plasmids pDAB1596 and pDAB1598.
Figure 34B:
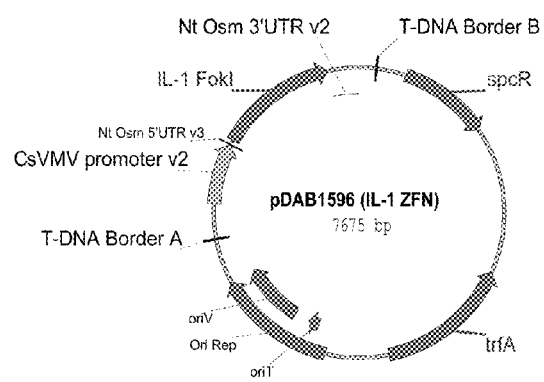
Figure 34C:
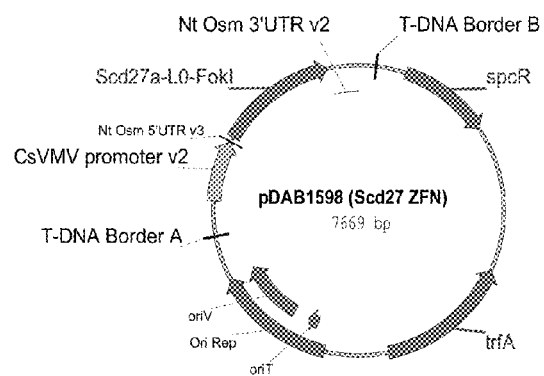

The binary versions of these vectors were constructed by excising the zinc finger fusion protein gene expression cassettes from pDAB1592 and pDAB1594 as a. PmeI/XhoI fragments, filling in the ends and cloning into pDAB2407 at the PmeI site (FIG. 34A). The resultant plasmids were named pDAB1596 (FIG. 34B) and pDAB1598 (FIG. 34C) for IL-1 ZFN and Scd27 ZFN, respectively and were the binary version of the zinc finger fusion protein gene vectors plant cell re-transformation.

Example 6

Design and Generation of Positive Control Vector

Figure 35:
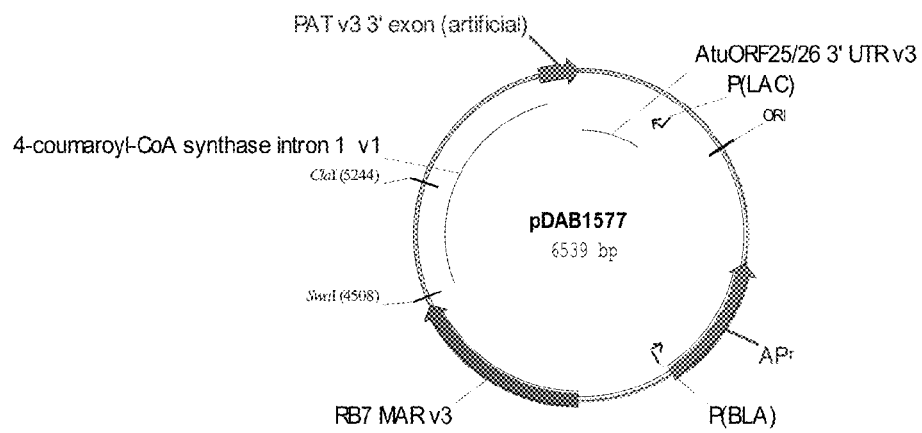
FIG. 35 is a schematic representation of the plasmid pDAB1577.
Figure 36:
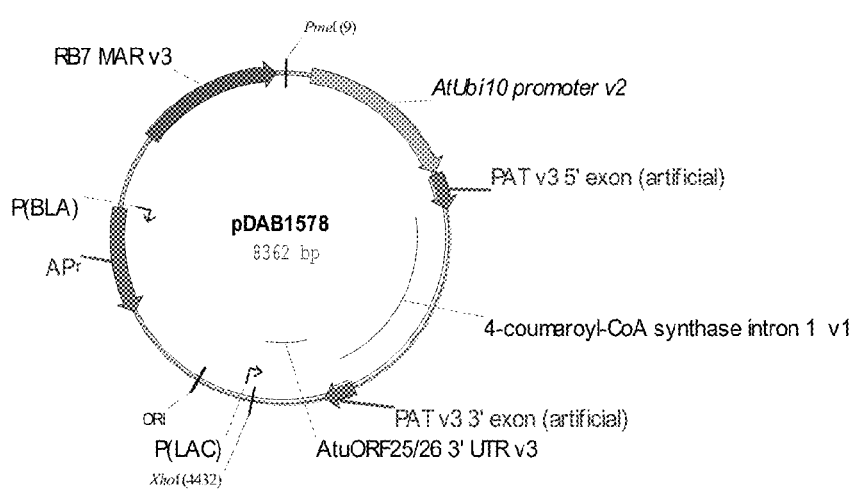
FIG. 36 is a schematic representation of the plasmid pDAB1578.

To estimate the illegitimate recombination frequency and serve as a positive control, a vector containing the PAT gene expression cassette was used. In order to be comparable with the final recombinants, the *A. thaliana* 4-CoAS intron-1 (Locus At3g21320, GenBank N.C. 003074) was inserted at the 299/300 bp of the PAT coding sequence (Wohlleben et al., 1988, Gene 70:25-37). To make this construct, the 2559 bp SwaI/ClaI fragment from pDAB1576 was ligated with the backbone fragment of pDAB1577 (FIG. 35) which was digested with the same restriction enzymes. The resulting vector contained the PAT gene expression cassette with the 043 bp of *A. thaliana* 4-CoAS intron-1 (Locus At3g21320, GenBank N.C. 003074) (Locus At3g21320, GenBank N.C. 003074) insertion in the middle of PAT coding sequence (Wohlleben et al., 1988, Gene 70:25-37). This vector was named pDAB1578 (FIG. 36).

To make the binary version of pDAB1578, the PAT gene expression cassette with the *A. thaliana* intron-1 (Locus At3g21320, GenBank N.C. 003074) was excised from pDAB1578 with PmeI/XhoI. After the 3' end of the fragment was blunt-end treated, it was inserted into pDAB2407, the binary base vector, at the PmeI site. The resulting vector was named pDAB1601 (FIG. 37) which comprised the PAT gene (Wohlleben et al., 1988, Gene 70:25-37) containing *A. thaliana* 4-CoAS intron-1 (Locus At3g21320, GenBank N.C. 003074) sequence driven by the *A. thaliana* ubi10 promoter (Callis, et al., 1990, J. Biol. Chem. 265-12486-12493) and terminated by the *A. tumefaciens* orf25/26 3' UTR (Gelvin et al., 1987, EP222493).

Example 7

Re-Transformation of Target Cell Cultures with Zinc Finger Nuclease Genes and Donor DNA Sequences Three independent, hygromycin-resistant, transgenic cell cultures (NT1-240, NT1-260 and BY2-380), each containing a single, full-length integrated copy of the target sequence, were selected and used to re-initiate suspension cultures by placing~250-500 mg of callus tissue into 40-50 mL of basal medium (MS- or LS-based for NT1 and BY2, respectively) containing 100 mg/L hygromycin and sub-culturing every 7 days as described above. Prior to re-transformation, the suspension cultures were transferred to basal medium without hygromycin.

*Agrobacterium*-mediated transformation of the target cell cultures was performed as described above. For each experiment, 10 co-cultivation plates were generated as follows: one plate comprised cells co-cultivated with 100 μL of an *Agrobacterium* strain harboring pDAB1600 (donor DNA); one plate comprised cells co-cultivated with 100 μL of an *Agrobacterium* strain harboring pDAB1601 (PAT selectable Marker); four plates comprised cells co-cultivated with 50 μL of an *Agrobacterium* strain harboring pDAB1600 (donor DNA) and 250 μL of an *Agrobacterium* strain harboring pDAB1596 (IL-1 ZFP-Fok1); and four plates comprised cells co-cultivated with 50 μL of an *Agrobacterium* strain harboring pDAB1600 (donor DNA) and 250 μL of an *Agrobacterium* strain harboring pDAB1598 (Scd 27a ZFP-Fok1). Following co-cultivation using the methods described above, the cells were plated out on basal medium (MS- or LS-based for NT1 and BY2, respectively) containing 500 mg/L carbenicillin and either 10 mg/L or 15 mg/L Bialaphos®, respectively, for NT1 or BY2. Individual Bialaphos®-resistant isolates appeared 2-4 weeks after plating (Table 3) and were transferred to individual 60×20 mm plates (one isolate per plate) where they were maintained as callus on a 14-day subculture schedule until needed for analysis.

TABLE 3

Summary of Re-transformation of Target Cell Cultures with Zinc Finger-Fok1 Fusion Protein Genes and Donor DNA

| Target Cell Culture | Treatment | # of Selection Plates | # of Transgenic Events | Ave. # of Events per Selection Plate |
|---|---|---|---|---|
| NT1-240 | pDAB1601 (PAT Selectable Marker) | 59 | 1,490 | 25.3 |
|  | pDAB1600 (Donor DNA only) | 35 | 0 | 0 |
|  | pDAB 1600 + pDAB 1596 (Donor DNA + IL-1 ZFP-Fok1) | 251 | 293 | 1.2 |
|  | pDAB 1600 + pDAB 1598 (Donor DNA + Scd27a ZFP-Fok1) | 251 | 247 | 1.0 |
| NT1-260 | pDAB1601 (PAT Selectable Marker) | 35 | 427 | 12.2 |
|  | pDAB1600 (Donor DNA only) | 35 | 0 | 0 |
|  | pDAB 1600 + pDAB 1596 (Donor DNA + IL-1 ZFP-Fok1) | 251 | 35 | 0.1 |
|  | pDAB 1600 + pDAB 1598 (Donor DNA + Scd27a ZFP-Fok1) | 251 | 76 | 0.3 |
| BY2-380 | pDAB1601 (PAT Selectable Marker) | 46 | 536 | 11.7 |
|  | pDAB1600 (Donor DNA only) | 46 | 0 | 0 |
|  | pDAB 1600 + pDAB 1596 (Donor DNA + IL-1 ZFP-Fok1) | 214 | 43 | 0.2 |
|  | pDAB 1600 + pDAB 1598 (Donor DNA + Scd27a ZFP-Fok1) | 214 | 47 | 0.2 |

Example 8

Confirmation of Homologous Recombination

A. Inter-Chromosomal Homologous Recombination

Two strategies were developed and tested for zinc finger-Fok1 fusion protein-facilitated inter-chromosomal homologous recombination in the exemplary tobacco system described in Examples 1 to 7.

Figure 37A:
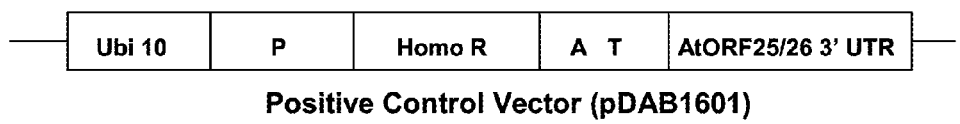
FIGS. 37A and 37B are schematic representations of plasmid pDAB1601.
Figure 37B:
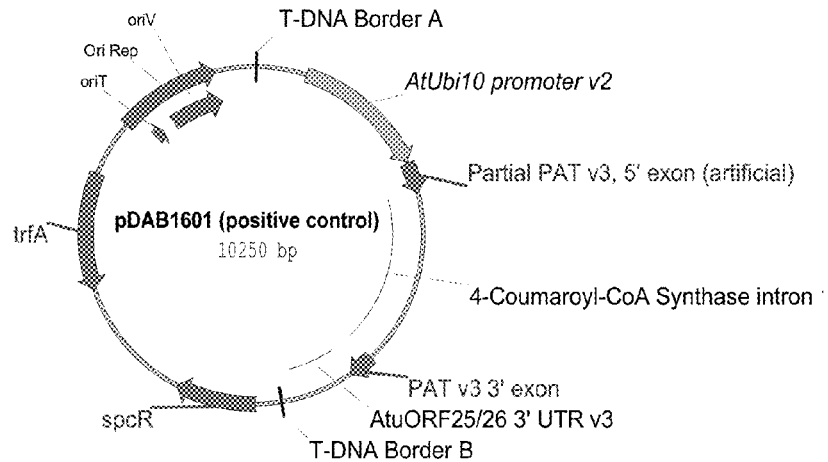
Figure 38:
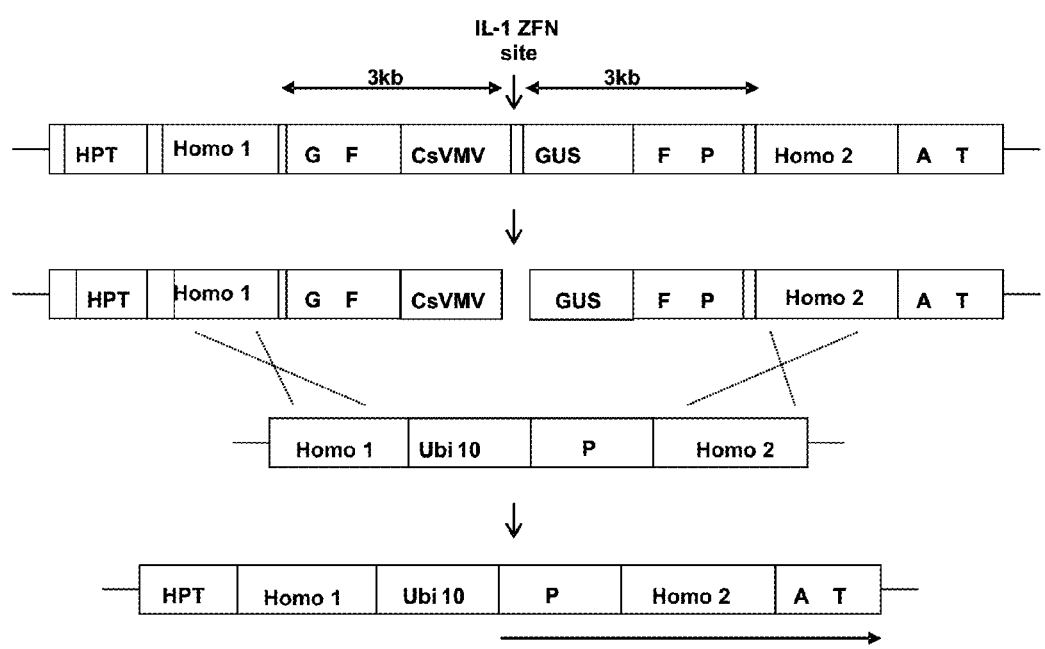
FIG. 38 is a schematic depicting predicted inter-chromosomal homologous recombination stimulated by the IL-1 ZFN-FokI fusion.

In strategy 1, the binding site for the zinc finger-Fok1 fusion protein (IL-1-L0-Fok1), was included in the middle of the target construct (FIG. 37). In this strategy, the binding site was flanked by ~3 kb of non-homologous sequences on both sides followed by homologous sequence-1 (*N. tabacum* RB7 MAR) and homologous sequence-2 (*A. thaliana* 4-CoAS intron-1) upstream and downstream, respectively (FIG. 38). It was hypothesized that in the presence of IL-1 zinc finger-Fok1 fusion protein, the IL-1-L0-FokI binding sequences would be recognized and a double stranded DNA break would be induced at this specific site, which would stimulate the endogenous DNA repair process. In the presence of donor DNA, which contained homologous sequences identical to that in the target sequence, the 5' partial PAT gene along with its promoter, would replace the entire ~6 kb DNA fragment between the homologous sequences in the target through homologous recombination. Through this process, the two partial PAT gene sequences, with the *A. thaliana* 4-CoAS intron-1 interposed between, would reconstitute a functional PAT gene, resulting in PAT expression and an herbicide resistance phenotype.

Figure 39:
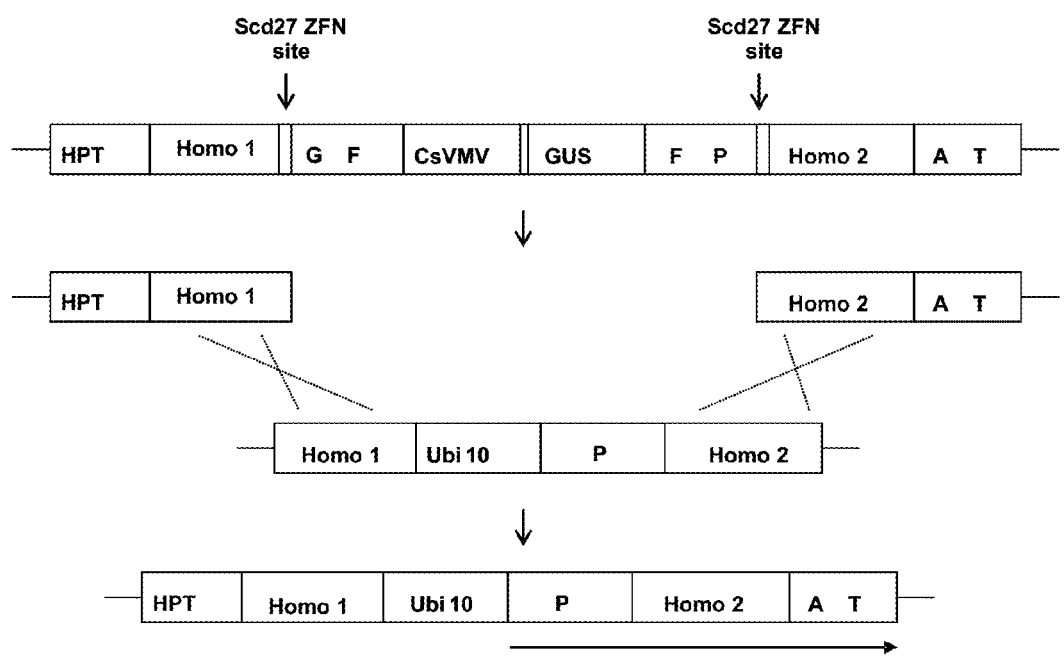
FIG. 39 is a schematic depicting predicted inter-chromosomal homologous recombination stimulated by the Scd27 ZFN-FokI fusion.

In strategy 2, two zinc finger-Fok1 binding sites (Scd27-L0-FokI) were included in the target vector: one directly downstream of the *N. tabacum* RB7 MAR and the other directly upstream of the *A. thaliana* 4-CoAS intron1 (FIG. 39). In between the two zinc finger-Fok1 fusion protein binding sites were ~6 kb of sequence, which included the 5' GFP fragment, a GUS expression cassette and the 3' GFP fragment. It was hypothesized that in the presence of Scd27 zinc finger-Fok1 fusion protein, the two binding sequences would be recognized and double stranded DNA breaks would be induced at both locations, which would remove the ~6 kb DNA fragment in between these two binding sequences, and stimulate the endogenous DNA repair process. Similar to the strategy 1, in the presence of donor DNA, which contained homologous sequences identical to that in the target sequence, the 5' partial PAT gene along with its promoter, would be inserted into the target sequence through homologous recombination at the site where the double strand DNA breaks were induced. Through this process, the two partial PAT gene sequences, with the *A. thaliana* 4-CoAS intron-1 interposed between, would reconstitute a functional PAT gene, resulting in PAT expression and an herbicide resistance phenotype.

Figure 40:
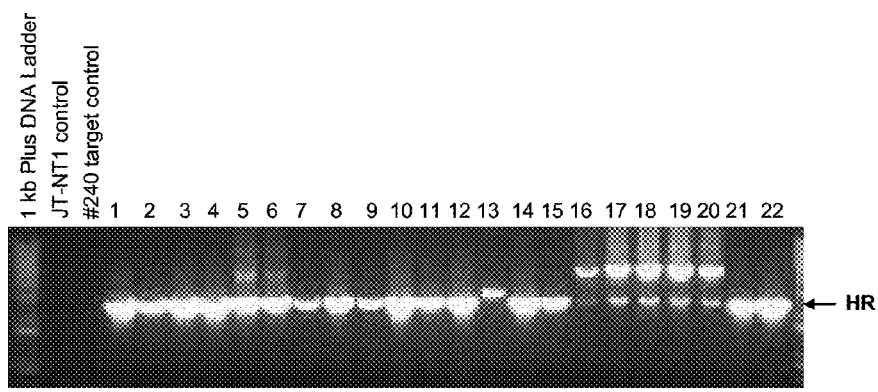
FIG. 40 shows PCR analysis of the recombinants. Lanes designated 1-20 shows homologous recombination events from the transformation of NT1-240 with SCD27-FokI fusion protein construct. Lanes designated 21 and 22 show homologous recombination events from the transformation of NT1-240 with SCD27-FokI fusion protein construct. Control lanes are shown in the 3 left most lanes.

All isolates obtained following herbicide (Bialaphos®) selection were first analyzed by PCR using primer pair P24/25, which amplified a DNA fragment spanning the reconstituted PAT gene. Primer P24 was homologous to the 5' end of the PAT coding sequence in the donor DNA and primer P25 was homologous to the 3' end of the PAT coding sequence in the target DNA. A 2.3 kb PCR fragment would result if the two partial PAT coding sequences were joined through homologous recombination. As shown in FIG. 40, a 2.3 kb PCR product was obtained from many of the isolates analyzed. These isolates were obtained from both the co-transformation of IL-1 zinc finger-Fok1 fusion protein gene/donor DNA and Scd27 zinc finger-Fok1 fusion protein gene/donor DNA. The 2.3 kb PCR products from multiple independent isolates representative of those derived from both IL-1 zinc finger-Fok1 and Scd27 zinc finger-Fok1 fusion protein gene transformations were purified from agarose gels and cloned into the pCR2.1 TOPO vector (Invitrogen, Carlsbad, Calif.). The 2.3 kb PCR product inserted in the TOPO vector was then sequenced using the Dye Terminator Cycle Sequencing Kit (Beckman Coulter). The sequencing results confirmed that all of the PCR products cloned in the TOPO vector contained the recombined sequence as predicted, including the 5' and 3' partial PAT gene sequences with the intervening *N. tabacum* 4-CoAS intron-1. These results confirmed the predicted inter-chromosomal recombination for both strategies tested and exemplified gene targeting via zinc finger-Fok1 fusion protein gene expression.

A couple of samples were further analyzed by PCR using primer pair P26/P25 which amplified a DNA fragment across the entire recombined region. Primer P26 was homologous to the 3' end of the HPT gene coding region in the target sequence and primer P25 was homologous to the 3' end of the PAT gene coding region in the target sequence. A predicted 5.2 kb PCR product would be obtained if homologous recombination occurred between the target sequence and the donor DNA. The non-recombined target would yield a PCR product of ~10 kb. A 5.2 kb PCR product was obtained from both samples analyzed. The 5.2 kb PCR product from one of the samples analyzed was purified from an agarose gel, cloned into pCR2.1 TOPO vector (Invitrogen, Carlsbad, Calif.). The PCR product was then sequenced using the Dye Terminator Cycle Sequencing Kit (Beckman Coulter, Fullerton, Calif.). The sequencing results confirmed that the PCR product contained the recombined sequence, including (from 5' to 3'): the 3' end of the HPT coding region (from the target sequence), the *A. thaliana* orf-24 3' UTR (from target sequence), the *N. tabacum* RB7 MAR (homologous sequence-1), *A. thaliana* ubi-10 promoter (from donor DNA), 5' partial PAT gene (from donor DNA), *A. thaliana* 4-CoAS intron-1 (homologous sequence-2), 3' partial PAT gene (from target sequence). This result further confirmed that the PCR products resulted from inter-chromosomal homologous recombination.

Figure 41:
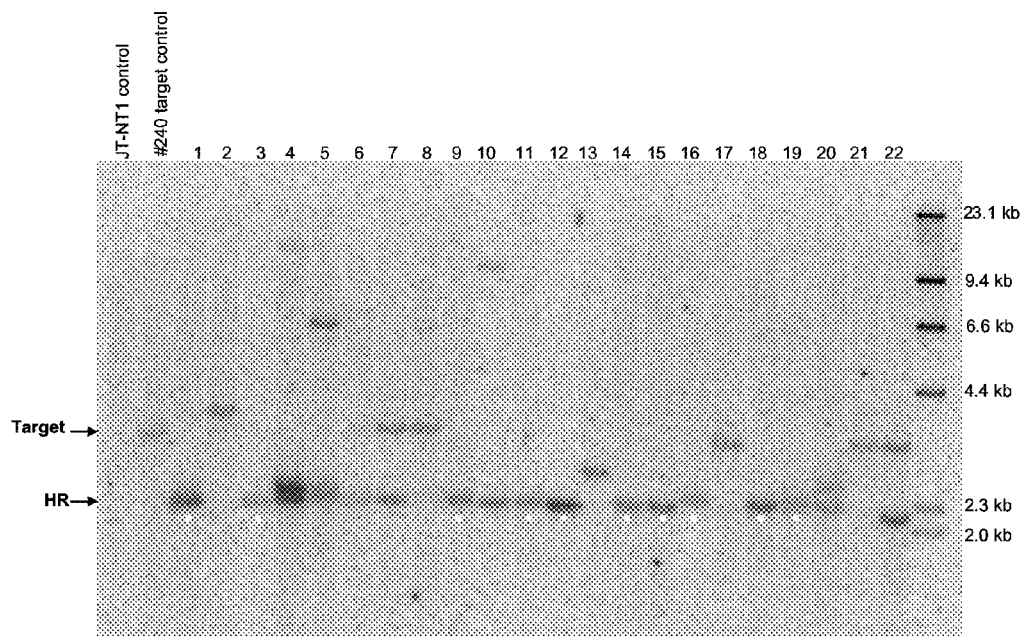
FIG. 41 shows Southern blot analysis of the recombinants. Lanes designated 1-20 shows homologous recombination events from the transformation of NT1-240 with SCD27-FokI fusion protein construct. Lanes designated 21 and 22 show homologous recombination events from the transformation of NT1-240 with SCD27-FokI fusion protein construct. Control lanes are shown in the 2 left most lanes.

To further analyze the recombinants at the genomic level, Southern blot analysis was carried out with a set of 22 isolates selected from both IL-1 zinc finger-Fok1 fusion protein gene/donor DNA and Scd27 zinc finger-Fok1 fusion protein gene/donor DNA transformations. All of the samples were confirmed to be recombinants by PCR analysis. Ten µg of genomic DNA from each sample was digested with BanII The digested genomic DNA was separated on a 0.8% agarose gel and transferred onto a nylon membrane. After cross-linking on the membrane, the DNA was hybridized with a 3' PAT probe. The expected recombinants would yield a band of 2079 by while the non-recombined target sequence would yield a band of 3018 bp. Results showed that out of 22 samples analyzed, 18 samples had a band with expected size of ~2 kb, which indicated these events were derived via homologous recombination in the vicinity the two partial PAT fragments (FIG. 41). Two samples displayed a band of unexpected size (one larger and one smaller than the target control) which suggests that the recombination in these two samples was not totally homology-dependent or that additional sequence rearrangements occurred during or after recombination. Another 2 samples displayed a band identical to the target control (~3 kb), indicating that these samples were either escapes from the herbicide selection or a mixed population of cells with only a small proportion having been derived from homologous recombination below the detection level for Southern blot analysis. Most likely the latter was the case since these samples displayed the expected amplification product corresponding to homologous recombination when analyzed with PCR. Out of the 18 samples that displayed the expected recombination band, 4 samples also had an additional band with the size identical to the target control, indicating that these samples represented a mixed population of cells with some cells non-recombined. Another 4 samples had additional bands of various sizes, indicating that these samples were genetic chimeras comprising some cells that had undergone non-homology-dependent events. Overall, 10 out of 22 samples were confirmed by Southern blot analysis to have undergone homologous recombination as predicted, at least in the region that involved in the two partial PAT fragments.

B. Intra-Chromosomal Homologous Recombination

Figure 42:
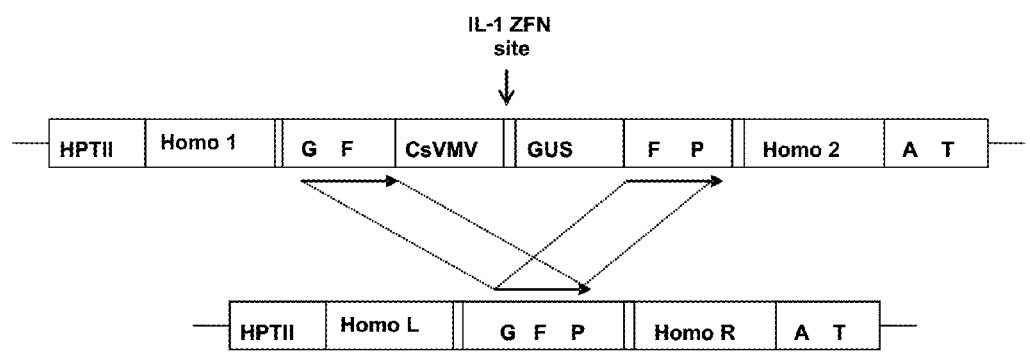
FIG. 42 is a schematic depicting predicted intra-chromosomal homologous recombination stimulated by the IL-1 ZFN-FokI fusion.

To test zinc finger-Fok 1-facilitated intra-chromosomal homologous recombination, two nonfunctional GFP fragments with 540 by overlap sequences were included in the target vector as described in FIG. 42. In between these two fragments was a GUS gene expression cassette. The IL-1-Fok1 fusion protein binding sequence was fused with the GUS coding sequence at its N-terminal. It was hypothesized that in the presence of IL-1-Fok1 fusion protein, the IL-1 ZFN binding sequences would be recognized and a double stranded DNA break would be induced, which would stimulate the endogenous DNA repair process. Without the presence of donor DNA, the two partially homologous GFP fragments would undergo an intra-chromosomal homologous recombination process and a functional GFP gene would be reconstituted.

Two target lines, BY2-380 and NT1-260 were transformed with plasmid pDAB1596 (the IL-1-Fok1 fusion protein gene binary vector) through *Agrobacterium*-mediated transformation as described above. Both donor DNA (pDAB1600) and the PAT control DNA (pDAB1601) were included as separate control treatments. Cells were plated onto non-selection medium after transformation. Apparent expression of the constituted functional GFP gene resulted in visible fluorescence around 5-8 days after transformation As summarized in Table 4, ~50 fluorescent loci were observed in each plate transformed with the IL-1-Fok1 fusion protein gene construct (pDAB1596). No significant difference was observed between the two target lines tested. No appreciable fluorescence beyond slight background was observed in the negative controls transformed with the donor DNA or PAT gene constructs.

TABLE 4

Constitution of Functional GFP through IL-1-Fok1 zinc finger fusion protein-stimulated intra-chromosomal homologous recombination

| Target Line | Transformation Treatment | # Fluorescent Loci per Plate |
|---|---|---|
| BY2-380 | IL-1-Fok1 (pDAB1596) | 51.4 |
|  | PAT Gene (pDAB1601) | 2.0 |
|  | Donor DNA Only (pDAB1600) | 0 |
| NT1-260 | IL-1-Fok1 (pDAB1596) | 53.0 |
|  | PAT Gene (pDAB1601) | 0 |
|  | Donor DNA Only (pDAB1600) | 0 |

Figure 43:
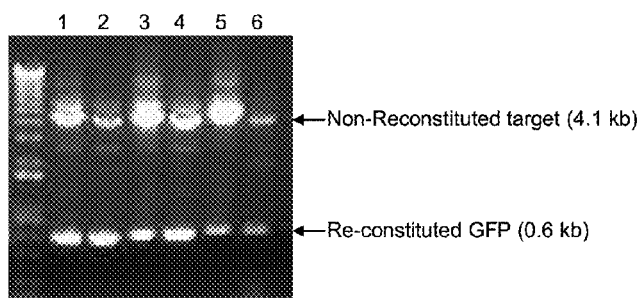
FIG. 43 is PCR analysis confirming that GFP is reconstituted in fluorescent tissues expressing the IL-1-FokI fusion protein.

To confirm that the green fluorescent loci resulted from reconstitution of a functional GFP gene, molecular analysis of the GFP expressing tissue was carried out. Since all the cells were plated on non-selective medium, it was difficult to obtain a cell population that was homogeneous with respect to GFP expression. A number of fluorescing tissue segments were isolated from the plate (with the aid of a dissecting microscope) and enriched through several passages of selective sub-culture. Genomic DNA was isolated from these visually enriched tissues and assayed by PCR using the primer pair P27/P28. The primer P27 was homologous to the 5' end of the 5' partial GFP fragment in the target DNA sequence and primer P28 was homologous to the 3' end of the 3' partial GFP fragment in the target DNA sequence. A predicted 0.6 kb PCR product would be obtained if the GFP gene had been reconstituted through intra-chromosomal homologous recombination between these two partial GFP fragments. The non-recombined target would yield a PCR product of 4.1 kb. As shown in FIG. 43, all of the samples that were enriched from fluorescing tissues had the predicted 0.6 kb PCR product, which indicated, that a functional GFP gene had been reconstituted in these tissues. A second 4.1 kb PCR product was also observed in all of these enriched samples, which indicated the presence of the non-recombined cell population. This was not unexpected since these samples were only enriched via visual selection using fluorescence as an indicator. The PCR products were separated on a 0.8% agarose gel, transferred onto a nylon membrane and probed with the GFP gene coding sequence. The results indicated that the two PCR products, 0.6 kb and 4.1 kb, contained GFP sequence, thereby confirming that the fluorescence resulted from expression of a reconstituted GFP gene.

Example 9

Design of Zinc Finger-Fok1 Fusion Protein Targeted to a Gene in a Monocot

Zinc finger nucleases, for facilitating homology-directed repair in a monocot (e.g., maize, sorghum, wheat, barley, rice) are designed and synthesized as follows. A gene of interest is selected, which gene preferably includes at least one codon that can be targeted for an amino acid substitution. The relevant portion of the selected gene is cloned and the nucleotide sequence of the clone is determined.

The sequence thus obtained is scanned, optionally using a computer program containing a listing of individual zinc fingers and their target sites and/or a listing of two-finger modules and their target sites, for a pair of target sequences, separated by 5-6 nucleotide pairs, wherein each target sequence can be bound by a 3-, 4-, 5- or 6-finger zinc finger protein. See, for example, U.S. Pat. No. 6,785,613; WO 98/53057; WO 01/53480 and U.S. Patent Application Publication No. 2003/0092000. Additional methods for ZFP design are disclosed, for example, in U.S. Pat. Nos. 5,789,538; 6,013,453; 6,410,248; 6,733,970; 6,746,838; 6,785,613; 6,866,997; 7,030,215; WO 01/088197; WO 02/099084; and US Patent Application Publications 2003/0044957; 2003/0108880; 2003/0134318 and 2004/0128717.

For each target sequence identified in the previous step, a gene encoding a fusion between a Fold cleavage half-domain and a zinc finger protein that binds to the target sequence is synthesized. See, for example, U.S. Pat. No. 5,436,150; WO 2005/084190 and U.S. Patent Application Publication No. 2005/0064474. Each fusion protein is then tested for the affinity with which it binds to its target sequence, using an ELISA assay as described, for example, by Bartsevich et al. (2003) *Stem Cells* 21:632-637. Proteins having target sequence binding affinities which exceed a predetermined threshold value are subjected to further testing in a cell-based reporter assay.

Optionally, the binding specificity of one or more fusion proteins as described above can be assessed and, if necessary, improved, using methods described in U.S. Pat. No. 6,794,136.

Cell-based testing is conducted as described, for example, in Urnov et al. (2005) Nature 435:646-651 and U.S. Patent Application Publication No. 2005/0064474. Briefly, a target sequence pair, identified as described above, is inserted into a defective chromosomal green fluorescent protein (GFP) gene, under the transcriptional control of a doxycycline-inducible promoter, in an appropriate cell line. Cells are transfected with nucleic acids encoding two zinc finger/FokI fusion proteins (each of which binds to one of the target sequences) and with a nucleic acid containing sequences that, if they serve as template for homology-directed repair of the defective chromosomal GFP gene, will reconstitute a functional GFP gene. Cells in which homology-directed repair has occurred can be identified and quantified by fluorescence-activated cell sorting, following induction with doxycycline.

Example 10

Design and Generation of Donor DNA Vector for Monocots

The donor DNA construct includes coding sequence (CDS) for the selected gene and genomic sequence upstream and/or downstream of the CDS. CDS and/or genomic sequences are obtained from the National Center for Biotechnology Information (NCBI) database and/or the Plant Genome Database. "Contig" matches between partial sequences and known sequences can be used to confirm that the sequences are derived from the same loci in the selected monocot genome. To avoid the zinc finger nuclease binding sequence being repetitively cleaved subsequent to recombination, two single nucleotide mutations, which do not cause a change in the encoded amino acid sequence, may also be made within the zinc finger nuclease (ZFN) binding sequence in the donor DNA. One or both of the mutations may create a restriction enzyme site, which facilitates downstream molecular characterization.

To construct the donor DNA vector, a DNA fragment, which covers some of the CDS and downstream sequence, is PCR amplified from the selected monocot's genomic DNA using suitable primers. Restriction sites (e.g., SadI and BamHI sites) are preferably added to the 5' and 3' end of the PCR fragments, respectively. The PCR product is cloned into pCR Blunt II TOPO vector (Invitrogen, Carlsbad, Calif.).

Figure 44:
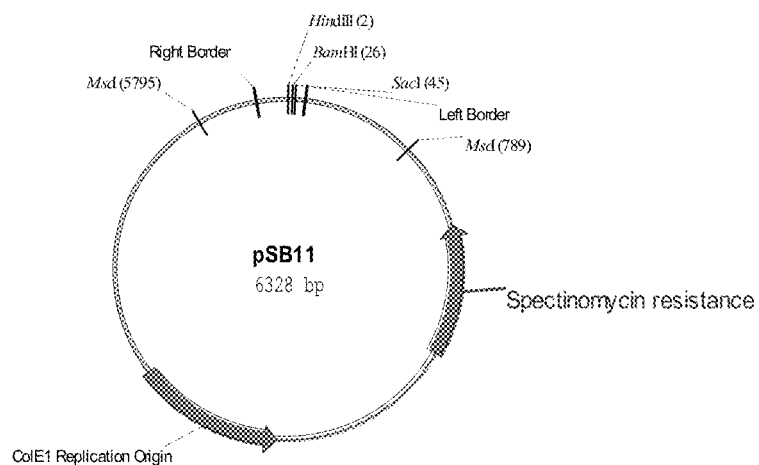
FIG. 44 is a schematic representation of plasmid pSB11.
Figure 45:
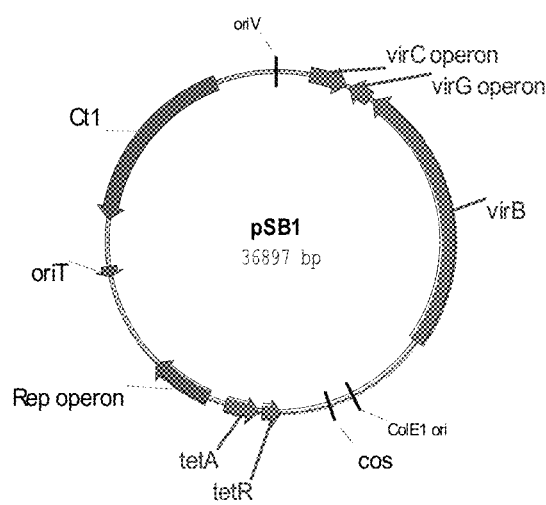
FIG. 45 is a schematic representation of plasmid pSB1.

A mutation at the desired location may be introduced by replacing one or more selected nucleotides using the QuickChange® site-directed mutagenesis kit (Stratagene, La Jolla, Calif.). As noted above, additional single silent mutations (e.g., 2, 3 or more single mutations) can also introduced in the zinc finger-FokI binding sequence in a similar way using the QuickChange® site-directed mutagenesis kit (Stratagene, La Jolla, Calif.). The PCR fragment with the substitution mutation and additional silent single mutations is isolated from the pCR Blunt II TOPO vector by appropriate digestion and cloned into pSB11 (FIG. 44) at the same sites. The resultant plasmid DNA is then transformed into an *Agrobacterium* strain that hosts pSB1 plasmid (FIG. 45) to form a super-binary donor vector for plant cell transformation through homologous recombination.

Example 11

Figure 46:
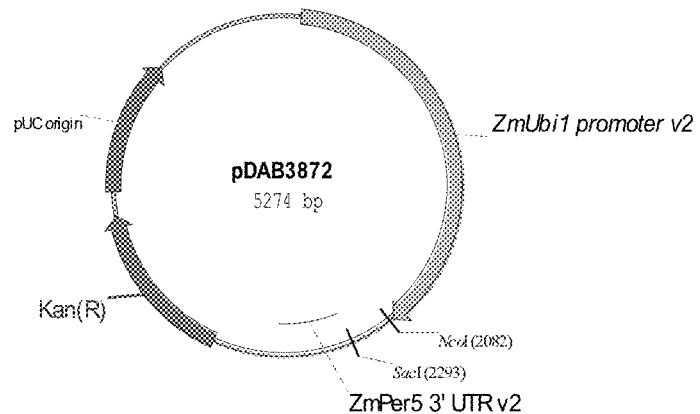
FIG. 46 is a schematic representation of the plasmid pDAB3872.
Figure 47:
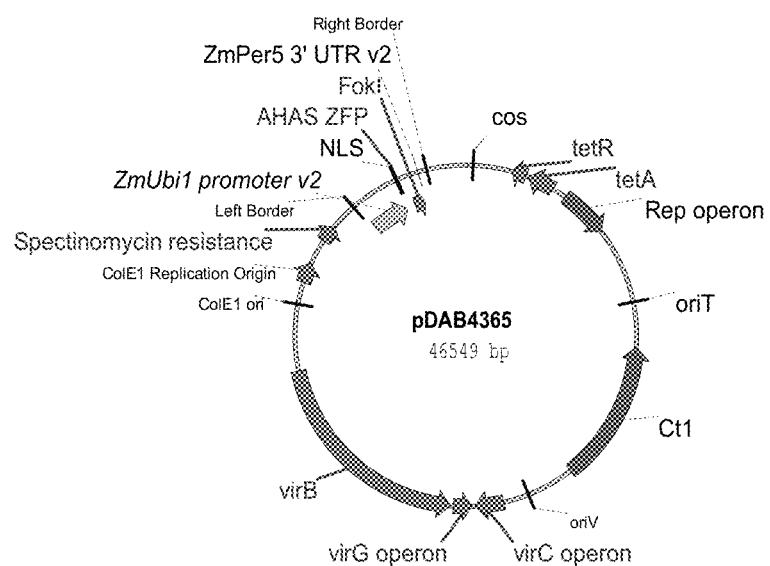
FIG. 47 is a schematic representation of plasmid pDAB4365.

Design and Generation of a Monocot Zinc Finger-FokI Fusion Protein Gene Vector for Transformation The zinc finger-FokI fusion protein gene is driven by a suitable monocot promoter (e.g., *Z. mays* ubi1 promoter (Quail et al., U.S. Pat. No. 5,614,399)). The cassette may also include *Z. mays* peroxidase-5 (per5) 3' UTR (Ainley et al., WO9856921). To make this vector, the zinc finger-FokI fusion protein gene is isolated from its original source vector by NcoI/SacI digestion and cloned into pDAB3872 (FIG. 46) at the same sites. The expression cassette including *Z. mays* ubi-1 promoter, the zinc finger-FokI fusion protein gene and *Z. mays* per-5 3' UTR, is isolated from the intermediate vector made above by HindIII/MscI digestion and inserted into pSB11 at HindIII/PmeI site. The resultant plasmid is then transformed into an *Agrobacterium* strain that hosts pSB1 plasmid to form the super-binary vector, pDAB4365 through homologous recombination (FIG. 47). pDAB4365 is the super-binary version of the zinc finger-FokI fusion protein gene expression vector for plant cell transformation.

Example 12

Transformation of Maize Cells with Zinc Finger Nuclease Genes and Donor DNA and Generation of Cell Cultures Seed of the 'High II' $F_1$ cross (Armstrong, et al., 1991, Maize Genet. Coop. News Lett. 65:92-93) can be planted directly into 5 gallon-pots containing a commercial soil mix (Conrad Fafard, Inc., Springfield; Soil Mix #3). The plants are grown in the greenhouse with a 16-hour photoperiod supplemented by a combination of high pressure sodium and metal halide lamps resulting in approximately 1,500 ft-candles of illumination. The day and night temperature is maintained at 27/20±2° C. The plants are watered as needed with the standard fertilizer tank mix.

For obtaining immature embryos, controlled pollination (sibs or selfs) can be performed. Plants at anthesis are prepared for pollination by cutting back silks one day prior to pollination, thereby producing a full brush of silks for maximum fertilization and seed set. On the day of pollination, actively shedding tassels are bagged, and fresh pollen collected and applied carefully onto the silks. When the developing embryos reach 1.0-1.2 mm size (9-10 days after pollination), the ear can be excised and surface sterilized. Briefly, ears are subjected to immersions in 70% ethanol for 2-5 minutes and 20% commercial bleach (0.1% sodium hypochlorite) for 30-45 minutes followed by 3 rinses in sterile, distilled water. Following sterilization, immature embryos can be isolated.

Two different *Agrobacterium* strains are used for transformation. The first harbors the zinc finger nuclease gene construct as described in Examples 9-11 and the second harbors the donor DNA sequence comprising the substitution mutation. The 'Super Binary' vector system from Japan Tobacco described in U.S. Pat. No. 5,591,616 can be used.

To prepare the *Agrobacterium* suspensions, 1-2 loops of bacteria from a streak plate (containing 5 g/L Yeast extract, 10 g/L Bacto-Peptone, 5 g/L sodium chloride, 50 mg/L spectinomycin, 10 mg/L tetracycline and 15 g/L Bacto Agar) are placed into 5 mL of 'infiltration' medium. The 'infiltration' medium consists of LS basal salts (Linsmaier et al., 1965, Physiol. Plant.), N6 vitamins (Chu et al., 1975, Sci. Sinica 18:659-668), 1.5 mg/L 2,4-D, 68.5 g/L sucrose, 36 g/L glucose, 6 mM proline adjusted to pH 5.2 prior to filter sterilization. The mixture is vortexed until a uniform suspension is achieved. The bacterial concentration can be determined using a Klett-Summerson Photoelectric Colorimeter by reading the density of the solution. The solution is adjusted to a concentration of Klett 200 (~1×10$^9$ cfu/mL) and acetosyringone is added to achieve a final concentration of 100 µM.

The immature embryos are isolated directly into a microfuge tube containing 2 mL of 'infiltration' medium. Each tube, containing ~100 embryos, is vortexed for 3-5 sec. The medium is removed and replaced with fresh liquid medium of the same composition and the vortex repeated. The liquid medium is again removed and replaced with 1 mL of *Agrobacterium* solution (800 µL of the zinc finger nuclease strain and 200 µL of the donor DNA strain) at the Klett 200 concentration. The *Agrobacterium* and embryo mixture is vortexed for 30 sec. Following 5 minutes of incubation at room temperature, the embryos can be transferred and placed embryo axis down on 'co-cultivation' medium containing for 5 days in the dark at 25° C. The 'co-cultivation' medium consisted of LS basal salts (Linsmaier et al., 1965, Physiol. Plant.), N6 vitamins (Chu et al., 1975, Sci. Sinica 18:659-668), 1.5 mg/L 2,4-D, 30 g/L sucrose, 6 mM proline, 0.85 mg/L silver nitrate, 100 µM acetosyringone, 3 g/L GELRITE® adjusted to pH 5.8 prior to filter sterilization.

Example 13

Selection of Homologous Recombinants

After co-cultivation with a 5:1 mixture of the two *Agrobacterium* strains harboring the zinc finger nuclease gene cassette and donor DNA, respectively, embryos are moved to 'callus' medium which may include components that stop further growth of the *Agrobacterium* (e.g., 250 mg/L Cefotaxime and/or 500 nM Pursuit®). The 'callusing' medium consisted of LS basal salts (Linsmaier et al., 1965, Physiol. Plant.), N6 vitamins (Chu et al., 1975, Sci. Sinica 18:659-668), 1.5 mg/L 2,4-D, 0.5 g/L MES, 30 g/L sucrose, 6 mM proline, 1 mg/L silver nitrate, 8 g/L TC agar (PhytoTechnology Laboratories, Shawnee Mission, Kans.) adjusted to pH 5.8 before autoclaving. Throughout the selection phase, the embryos are cultured in the dark at 28° C.

For plant regeneration, callus cultures are transferred to 'induction' medium and incubated at 27° C. with a 16/8 light/dark photoperiod in low light (13 µE/m$^2$/s) for one week followed by one week in high light (40 µE/m$^2$/s) provided by cool white fluorescent lamps. The 'induction' medium is composed of MS basal salts and vitamins (Murashige et al., 1962, Physiol. Plant. 15:473-497), 30 g/L sucrose, 5 mg/L 6-benzylaminopurine, 0.025 mg/L 2, 4-D, 2.5 g/L GELRITE® with pH adjusted to 5.7 before autoclaving. Following this two-week induction period, the callus is transferred to 'regeneration' medium and incubated in high light (40 µE/m$^2$/s) at 27° C. The 'regeneration' medium is identical to the 'induction' medium except that it lacks hormones. The callus can be sub-cultured to fresh 'regeneration' medium every two weeks until shoots appear.

When plantlets reach approximately 3-5 cm in length, they are transferred to 150×25 mm culture tubes containing SH basal salts and vitamins (Schenk et al., 1972, Can. J. Bot. 50:199-204), 10 g/L sucrose, 1 g/L myo-inositol and 2.5 g/L GELRITE® with pH adjusted to 5.8 before autoclaving. Once shoots reach the top of the of the tube, plantlets are transferred to 10 cm pots containing approximately 0.25 kg of commercial soil mix (Conrad Fafard, Inc., Springfield; Soil Mix #3), moistened thoroughly, and covered with clear plastic cups for 2-4 days. At the 3-5 leaf stage, plants are transplanted to 5-gallon pots and grown to maturity.

Additional information related to targeted cleavage, targeted recombination and targeted integration can be found in United States Patent Application publications US-2003-0232410; US-2005-0026157; US-2005-0064474; US-2005-0208489 and US-2007-0134796, the disclosures of which are incorporated by reference in their entireties for all purposes.

All patents, patent applications and publications mentioned herein are hereby incorporated by reference, in their entireties, for all purposes.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. A method for introducing an exogenous sequence into the chromosomal DNA of a plant cell, the method comprising the steps of:
   (a) contacting the cell with a donor DNA vector comprising an exogenous sequence encoding a protein, the exogenous sequence flanked by first and second sequences identical or homologous and non-identical to the chromosomal DNA of the plant cell; and
   (b) transforming the cell with one or more polynucleotides encoding first and second zinc finger nucleases in the cell, each zinc finger nuclease comprising a 3-, 4-, 5- or 6-finger zinc finger domain that binds to a target site in the chromosomal DNA and a cleavage domain and further wherein the first and second zinc finger nucleases dimerize to cleave the chromosomal DNA between and at a location from 0.1 to 3 kilobase pairs from the edges of the chromosomal DNA sequences having homology to the first and/or second sequences;
   such that cleavage of chromosomal DNA in step (b) stimulates incorporation of the exogenous DNA sequence into the genome by homologous recombination of the first and second sequences and chromosomal DNA.

2. The method of claim 1, wherein the cleavage domain comprises the cleavage domain of a Type IIS restriction endonuclease.

3. The method of claim 1, wherein the polynucleotides encoding the first and second zinc finger nucleases are stably integrated into the genome of the plant cell.

4. The method of claim 1, wherein the protein is a selectable marker.

5. The method of claim 4, wherein the selectable marker is selected from the group consisting of green fluorescent protein (GFP), β-glucuronidase (GUS), phosphinothricin N-acetyl transferase (PAT, BAR), neomycin phosphotransferase, β-lactamase, catechol dioxygenase, α-amylase, tyrosinase, β-galactosidase, luciferase, aequorin, EPSP synthase, nitrilase, acetolactate synthase (ALS), dihydrofolate reductase (DHFR), dalapon dehalogenase and anthranilate synthase.

6. The method of claim 1, wherein the exogenous sequence further comprises one or more regulatory sequences.

* * * * *

SEQUENCE LISTING

```
<160> NUMBER OF SEQ ID NOS: 4

<210> SEQ ID NO 1
<211> LENGTH: 30
<212> TYPE: DNA
<213> ORGANISM: Artificial Sequence
<220> FEATURE:
<223> OTHER INFORMATION: Zinc finger nuclease IL-1 recognition sequence

<400> SEQUENCE: 1
attatccgag tttaatagaa ctcggataat                                        30

<210> SEQ ID NO 2
<211> LENGTH: 30
<212> TYPE: DNA
<213> ORGANISM: Artificial Sequence
<220> FEATURE:
<223> OTHER INFORMATION: Zinc finger nuclease IL-1 recognition sequence
```

```
<400> SEQUENCE: 2
attatccgag ttctattaaa ctcggataat                                    30

<210> SEQ ID NO 3
<211> LENGTH: 30
<212> TYPE: DNA
<213> ORGANISM: Artificial Sequence
<220> FEATURE:
<223> OTHER INFORMATION: Zinc finger nuclease Scd27 recognition sequence

<400> SEQUENCE: 3
cgagttcttg tacaccagta caagaactcg                                    30

<210> SEQ ID NO 4
<211> LENGTH: 30
<212> TYPE: DNA
<213> ORGANISM: Artificial Sequence
<220> FEATURE:
<223> OTHER INFORMATION: Zinc finger nuclease Scd27 recognition sequence

<400> SEQUENCE: 4
cgagttcttg tactggtgta caagaactcg                                    30
```